US010208351B2

(12) United States Patent
Trabucchi et al.

(10) Patent No.: US 10,208,351 B2
(45) Date of Patent: Feb. 19, 2019

(54) RNY-DERIVED SMALL RNAS AS BIOMARKERS FOR ATHEROSCLEROSIS-RELATED DISORDERS

(71) Applicants: INSTITUT NATIONAL DE LA SANTE ET DE LA RECHERCHE MEDICALE (INSERM), Paris (FR); UNIVERSITE PAUL SABATIER TOULOUSE III, Toulouse (FR); UNIVERSITE DE NICE SOPHIA ANTIPOLIS, Nice (FR)

(72) Inventors: Michele Trabucchi, Nice (FR); Laurent Martinez, Toulouse (FR); Emanuela Repetto, Nice (FR)

(73) Assignees: INSTITUT NATIONAL DE LA SANTE ET DE LA RECHERCHE MEDICALE (INSERM), Paris (FR); UNIVERSITE PAUL SABATIER TOULOUSE III, Toulouse (FR); UNIVERSITE DE NICE SOPHIA ANTIPOLIS, Nice (FR)

( * ) Notice: Subject to any disclaimer, the term of this patent is extended or adjusted under 35 U.S.C. 154(b) by 0 days.

(21) Appl. No.: 15/030,275

(22) PCT Filed: Oct. 20, 2014

(86) PCT No.: PCT/EP2014/072451
§ 371 (c)(1),
(2) Date: Apr. 18, 2016

(87) PCT Pub. No.: WO2015/055857
PCT Pub. Date: Apr. 23, 2015

(65) Prior Publication Data
US 2016/0237500 A1  Aug. 18, 2016

(30) Foreign Application Priority Data
Oct. 18, 2013 (EP) .................................... 13306439

(51) Int. Cl.
*A61K 48/00* (2006.01)
*C12Q 1/6883* (2018.01)
*A61K 38/17* (2006.01)
*A61K 38/46* (2006.01)
*C12N 15/113* (2010.01)
*A61K 47/54* (2017.01)

(52) U.S. Cl.
CPC ........ *C12Q 1/6883* (2013.01); *A61K 38/1709* (2013.01); *A61K 38/465* (2013.01); *A61K 47/549* (2017.08); *C12N 15/113* (2013.01); *C12N 2310/14* (2013.01); *C12N 2310/3513* (2013.01); *C12N 2320/30* (2013.01); *C12Q 2600/118* (2013.01); *C12Q 2600/136* (2013.01); *C12Q 2600/178* (2013.01); *C12Y 301/26* (2013.01)

(58) Field of Classification Search
CPC ...................................................... A61K 48/00
See application file for complete search history.

(56) References Cited

FOREIGN PATENT DOCUMENTS

| WO | WO-00/53173 | 9/2000 |
| WO | WO-2005/024061 | 3/2005 |

OTHER PUBLICATIONS

Yamanashi et al. ("Bile Acid as Therapeutic Agents." Bile Acids in Gastroenterology. Springer Japan, 2017. 61-90.).*
International Search Report and Written Opinion of the International Searching Authority for International Application No. PCT/EP2014/072451, dated Feb. 3, 2015, European Patent Office, Rijswijk, NL.
Claudio Iaconetti et al: "Non-Coding RNAs: The "Dark Matter" of Cardiovascular Pathophysiology", International Journal of Molecular Sciences, vol. 14, No. 10, Jan. 1, 2013 (Jan. 1, 2013), pp. 19987-20018, XP055100290, DOI: 10.3390/ijms141019987, pp. 19990-19991, item 3.
M. U. Kaikkonen et al: "Non-coding RNAs as regulators of gene expression and epigenetics", Cardiovascular Research, vol. 90, No. 3, Jun. 1, 2011 (Jun. 1, 2011), pp. 430-440, XP055100292, ISSN: 0008-6363, DOI: 10.1093/cvr/cvr097, item 2.2-2.4; p. 432.
Manel Esteller: "Non-coding RNAs in human disease", Nature Reviews Genetics, vol. 12, No. 12, Nov. 18, 2011 (Nov. 18, 2011), p. 861-874, XP055100295, ISSN: 1471-0056, DOI: 10.1038/nrg3074, p. 863, figure 1.

* cited by examiner

*Primary Examiner* — Kimberly Chong
(74) *Attorney, Agent, or Firm* — B. Aaron Schulman, Esq.; Stites & Harbison, PLLC

(57) ABSTRACT

The present invention concerns an in vitro method of diagnosis or prognosis of an atherosclerosis-related disorder by detecting a small Y RNA (s-RNY), as well as the use of an inhibitor of s-RNY as a medicament against atherosclerosis-related disorders. The invention also concerns a method for screening for a compound suitable for the treatment of an atherosclerosis-related disorder.

6 Claims, 23 Drawing Sheets
Specification includes a Sequence Listing.

A.

B.

A.

B.

C.

A.

B.

| | |
|---|---|
| Mouse | AAGGCGCAUCUGCGUACACACAGGUGAGAAGCUU |
| Rat | AAGGCGCAUCUGAGGACGCACACAGGUGAGAAGCUU |
| Xenopus | AAAGCCCAUCUCAGAACCCACACAGGUGAGAAGCUU |
| Human | GCUUACUCUCGCCCCCUCCCUGCAGGUGAGAAGCCCU |
| | ** * ************ * |

C.

A.

B.

SEQUENCE LISTING

<160> NUMBER OF SEQ ID NOS: 63

<210> SEQ ID NO 1
<211> LENGTH: 113
<212> TYPE: DNA
<213> ORGANISM: Homo sapiens

```
<400> SEQUENCE: 1
ggctggtccg aaggtagtga gttatctcaa ttgattgttc acagtcagtt acagatcgaa      60
ctccttgttc tactctttcc cccttctca ctactgcact tgactagtct ttt             113

<210> SEQ ID NO 2
<211> LENGTH: 102
<212> TYPE: DNA
<213> ORGANISM: Homo sapiens

<400> SEQUENCE: 2
ggctggtccg agtgcagtgg tgtttacaac taattgatca caaccagtta cagatttctt      60
tgttccttct ccactcccac tgcttcactt gactagcctt tt                        102

<210> SEQ ID NO 3
<211> LENGTH: 96
<212> TYPE: DNA
<213> ORGANISM: Homo sapiens

<400> SEQUENCE: 3
ggctggtccg atggtagtgg gttatcagaa cttattaaca ttagtgtcac taaagttggt      60
atacaacccc ccactgctaa atttgactgg cttttt                                96

<210> SEQ ID NO 4
<211> LENGTH: 84
<212> TYPE: DNA
<213> ORGANISM: Homo sapiens

<400> SEQUENCE: 4
agttggtccg agtgttgtgg gttattgtta agttgattta acattgtctc cccccacaac      60
cgcgcttgac tagcttgctg tttt                                             84

<210> SEQ ID NO 5
<211> LENGTH: 111
<212> TYPE: DNA
<213> ORGANISM: Mus musculus

<400> SEQUENCE: 5
ggctggtccg aaggtagtga gttatctcaa ttgattgttc acagtcagtt acagattgaa      60
ctcctgttct acactttccc cccttctcac tactgcactt gactagtctt t              111

<210> SEQ ID NO 6
<211> LENGTH: 101
<212> TYPE: DNA
<213> ORGANISM: Mus musculus

<400> SEQUENCE: 6
ggttggtccg agagtagtgg tgtttacaac taattgatca caaccagtta cagatttctt      60
tgttccttct ccgctcccac tgcttcactt gaccagcctt t                         101

<210> SEQ ID NO 7
<211> LENGTH: 31
<212> TYPE: RNA
<213> ORGANISM: Homo sapiens

<400> SEQUENCE: 7
ggcugguccg aagguaguga guuaucucaa u                                     31

<210> SEQ ID NO 8
<211> LENGTH: 28
```

<212> TYPE: RNA
<213> ORGANISM: Homo sapiens

<400> SEQUENCE: 8
cuucucacua cugcacuuga cuagucuu                                      28

<210> SEQ ID NO 9
<211> LENGTH: 31
<212> TYPE: RNA
<213> ORGANISM: Homo sapiens

<400> SEQUENCE: 9
ggcugguccg agugcagugg uguuuacaac u                                  31

<210> SEQ ID NO 10
<211> LENGTH: 28
<212> TYPE: RNA
<213> ORGANISM: Homo sapiens

<400> SEQUENCE: 10
acucccacug cuucacuuga cuagccuu                                      28

<210> SEQ ID NO 11
<211> LENGTH: 31
<212> TYPE: RNA
<213> ORGANISM: Homo sapiens

<400> SEQUENCE: 11
ggcgguccga ugguaguggg uuaucagaac u                                  31

<210> SEQ ID NO 12
<211> LENGTH: 28
<212> TYPE: RNA
<213> ORGANISM: Homo sapiens

<400> SEQUENCE: 12 acccccacu gcuaaauuug acuggcuu                                       28

<210> SEQ ID NO 13
<211> LENGTH: 26
<212> TYPE: RNA
<213> ORGANISM: Homo sapiens

<400> SEQUENCE: 13
cccccacaac cgcgcuugac uagcuu                                        26

<210> SEQ ID NO 14
<211> LENGTH: 31
<212> TYPE: RNA
<213> ORGANISM: Mus musculus

<400> SEQUENCE: 14
ggcugguccg aagguaguga guuaucucaa u                                  31

<210> SEQ ID NO 15
<211> LENGTH: 28
<212> TYPE: RNA
<213> ORGANISM: Mus musculus

<400> SEQUENCE: 15
cuucucacua cugcacuuga cuagucuu                                      28

<210> SEQ ID NO 16

<211> LENGTH: 24
<212> TYPE: RNA
<213> ORGANISM: Mus musculus

<400> SEQUENCE: 16
gguugguccg agaguagugg uguu                                           24

<210> SEQ ID NO 17
<211> LENGTH: 28
<212> TYPE: RNA
<213> ORGANISM: Mus musculus

<400> SEQUENCE: 17
cuucucacua cugcacuuga cuagucuu                                       28

<210> SEQ ID NO 18
<211> LENGTH: 859
<212> TYPE: PRT
<213> ORGANISM: Homo sapiens

<400> SEQUENCE: 18

```
Met Tyr Ser Gly Ala Gly Pro Ala Leu Ala Pro Pro Ala Pro Pro Pro
1               5                   10                  15

Pro Ile Gln Gly Tyr Ala Phe Lys Pro Pro Arg Pro Asp Phe Gly
            20                  25                  30

Thr Ser Gly Arg Thr Ile Lys Leu Gln Ala Asn Phe Phe Glu Met Asp
        35                  40                  45

Ile Pro Lys Ile Asp Ile Tyr His Tyr Glu Leu Asp Ile Lys Pro Glu
    50                  55                  60

Lys Cys Pro Arg Arg Val Asn Arg Glu Ile Val Glu His Met Val Gln
65                  70                  75                  80

His Phe Lys Thr Gln Ile Phe Gly Asp Arg Lys Pro Val Phe Asp Gly
                85                  90                  95

Arg Lys Asn Leu Tyr Thr Ala Met Pro Leu Pro Ile Gly Arg Asp Lys
            100                 105                 110

Val Glu Leu Glu Val Thr Leu Pro Gly Glu Gly Lys Asp Arg Ile Phe
        115                 120                 125

Lys Val Ser Ile Lys Trp Val Ser Cys Val Ser Leu Gln Ala Leu His
    130                 135                 140

Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                165                 170                 175

Val Gly Arg Ser Phe Phe Thr Ala Ser Glu Gly Cys Ser Asn Pro Leu
            180                 185                 190

Gly Gly Gly Arg Glu Val Trp Phe Gly Phe His Gln Ser Val Arg Pro
        195                 200                 205

Ser Leu Trp Lys Met Met Leu Asn Ile Asp Val Ser Ala Thr Ala Phe
    210                 215                 220

Tyr Lys Ala Gln Pro Val Ile Glu Phe Val Cys Glu Val Leu Asp Phe
225                 230                 235                 240

Lys Ser Ile Glu Glu Gln Gln Lys Pro Leu Thr Asp Ser Gln Arg Val
                245                 250                 255

Lys Phe Thr Lys Glu Ile Lys Gly Leu Lys Val Glu Ile Thr His Cys
            260                 265                 270

Gly Gln Met Lys Arg Lys Tyr Arg Val Cys Asn Val Thr Arg Arg Pro
        275                 280                 285
```

```
Ala Ser His Gln Thr Phe Pro Leu Gln Gln Glu Ser Gly Gln Thr Val
    290                 295                 300
Glu Cys Thr Val Ala Gln Tyr Phe Lys Asp Arg His Lys Leu Val Leu
305                 310                 315                 320
Arg Tyr Pro His Leu Pro Cys Leu Gln Val Gly Gln Glu Gln Lys His
                325                 330                 335
Thr Tyr Leu Pro Leu Glu Val Cys Asn Ile Val Ala Gly Gln Arg Cys
                340                 345                 350
Ile Lys Lys Leu Thr Asp Asn Gln Thr Ser Thr Met Ile Arg Ala Thr
            355                 360                 365
Ala Arg Ser Ala Pro Asp Arg Gln Glu Glu Ile Ser Lys Leu Met Arg
    370                 375                 380
Ser Ala Ser Phe Asn Thr Asp Pro Tyr Val Arg Glu Phe Gly Ile Met
385                 390                 395                 400
Val Lys Asp Glu Met Thr Asp Val Thr Gly Arg Val Leu Gln Pro Pro
                405                 410                 415
Ser Ile Leu Tyr Gly Gly Arg Asn Lys Ala Ile Ala Thr Pro Val Gln
                420                 425                 430
Gly Val Trp Asp Met Arg Asn Lys Gln Phe His Thr Gly Ile Glu Ile
            435                 440                 445
Lys Val Trp Ala Ile Ala Cys Phe Ala Pro Gln Arg Gln Cys Thr Glu
    450                 455                 460
Val His Leu Lys Ser Phe Thr Glu Gln Leu Arg Lys Ile Ser Arg Asp
465                 470                 475                 480
Ala Gly Met Pro Ile Gln Gly Gln Pro Cys Phe Cys Lys Tyr Ala Gln
                485                 490                 495
Gly Ala Asp Ser Val Glu Pro Met Phe Arg His Leu Lys Asn Thr Tyr
                500                 505                 510
Ala Gly Leu Gln Leu Val Val Ile Leu Pro Gly Lys Thr Pro Val
            515                 520                 525
Tyr Ala Glu Val Lys Arg Val Gly Asp Thr Val Leu Gly Met Ala Thr
    530                 535                 540
Gln Cys Val Gln Met Lys Asn Val Gln Arg Thr Thr Pro Gln Thr Leu
545                 550                 555                 560
Ser Asn Leu Cys Leu Lys Ile Asn Val Lys Leu Gly Gly Val Asn Asn
                565                 570                 575
Ile Leu Leu Pro Gln Gly Arg Pro Pro Val Phe Gln Gln Pro Val Ile
                580                 585                 590
Phe Leu Gly Ala Asp Val Thr His Pro Pro Ala Gly Asp Gly Lys Lys
            595                 600                 605
Pro Ser Ile Ala Ala Val Val Gly Ser Met Asp Ala His Pro Asn Arg
    610                 615                 620
Tyr Cys Ala Thr Val Arg Val Gln Gln His Arg Gln Glu Ile Ile Gln
625                 630                 635                 640
Asp Leu Ala Ala Met Val Arg Glu Leu Leu Ile Gln Phe Tyr Lys Ser
                645                 650                 655
Thr Arg Phe Lys Pro Thr Arg Ile Ile Phe Tyr Arg Asp Gly Val Ser
                660                 665                 670
Glu Gly Gln Phe Gln Gln Val Leu His His Glu Leu Leu Ala Ile Arg
            675                 680                 685
Glu Ala Cys Ile Lys Leu Glu Lys Asp Tyr Gln Pro Gly Ile Thr Phe
    690                 695                 700
```

```
Ile Val Val Gln Lys Arg His His Thr Arg Leu Phe Cys Thr Asp Lys
705                 710                 715                 720

Asn Glu Arg Val Gly Lys Ser Gly Asn Ile Pro Ala Gly Thr Thr Val
            725                 730                 735

Asp Thr Lys Ile Thr His Pro Thr Glu Phe Asp Phe Tyr Leu Cys Ser
        740                 745                 750

His Ala Gly Ile Gln Gly Thr Ser Arg Pro Ser His Tyr His Val Leu
            755                 760                 765

Trp Asp Asp Asn Arg Phe Ser Ser Asp Glu Leu Gln Ile Leu Thr Tyr
        770                 775                 780

Gln Leu Cys His Thr Tyr Val Arg Cys Thr Arg Ser Val Ser Ile Pro
785                 790                 795                 800

Ala Pro Ala Tyr Tyr Ala His Leu Val Ala Phe Arg Ala Arg Tyr His
            805                 810                 815

Leu Val Asp Lys Glu His Asp Ser Ala Glu Gly Ser His Thr Ser Gly
        820                 825                 830

Gln Ser Asn Gly Arg Asp His Gln Ala Leu Ala Lys Ala Val Gln Val
            835                 840                 845

His Gln Asp Thr Leu Arg Thr Met Tyr Phe Ala
        850                 855

<210> SEQ ID NO 19
<211> LENGTH: 320
<212> TYPE: PRT
<213> ORGANISM: Homo sapiens

<400> SEQUENCE: 19

Met Ser Lys Ser Glu Ser Pro Lys Glu Pro Glu Gln Leu Arg Lys Leu
1               5                   10                  15

Phe Ile Gly Gly Leu Ser Phe Glu Thr Thr Asp Glu Ser Leu Arg Ser
            20                  25                  30

His Phe Glu Gln Trp Gly Thr Leu Thr Asp Cys Val Val Met Arg Asp
        35                  40                  45

Pro Asn Thr Lys Arg Ser Arg Gly Phe Gly Phe Val Thr Tyr Ala Thr
50                  55                  60

Val Glu Glu Val Asp Ala Ala Met Asn Ala Arg Pro His Lys Val Asp
65                  70                  75                  80

Gly Arg Val Val Glu Pro Lys Arg Ala Val Ser Arg Glu Asp Ser Gln
            85                  90                  95

Arg Pro Gly Ala His Leu Thr Val Lys Lys Ile Phe Val Gly Gly Ile
        100                 105                 110

Lys Glu Asp Thr Glu Glu His His Leu Arg Asp Tyr Phe Glu Gln Tyr
    115                 120                 125

Gly Lys Ile Glu Val Ile Glu Ile Met Thr Asp Arg Gly Ser Gly Lys
    130                 135                 140

Lys Arg Gly Phe Ala Phe Val Thr Phe Asp Asp His Asp Ser Val Asp
145                 150                 155                 160

Lys Ile Val Ile Gln Lys Tyr His Thr Val Asn Gly His Asn Cys Glu
            165                 170                 175

Val Arg Lys Ala Leu Ser Lys Gln Glu Met Ala Ser Ala Ser Ser Ser
        180                 185                 190

Gln Arg Gly Arg Ser Gly Ser Gly Asn Phe Gly Gly Gly Arg Gly Gly
    195                 200                 205

Gly Phe Gly Gly Asn Asp Asn Phe Gly Arg Gly Gly Asn Phe Ser Gly
    210                 215                 220
```

Arg Gly Gly Phe Gly Gly Ser Arg Gly Gly Gly Tyr Gly Gly Ser
225                 230                 235                 240

Gly Asp Gly Tyr Asn Gly Phe Gly Asn Asp Gly Ser Asn Phe Gly Gly
            245                 250                 255

Gly Gly Ser Tyr Asn Asp Phe Gly Asn Tyr Asn Asn Gln Ser Ser Asn
            260                 265                 270

Phe Gly Pro Met Lys Gly Gly Asn Phe Gly Gly Arg Ser Ser Gly Pro
            275                 280                 285

Tyr Gly Gly Gly Gln Tyr Phe Ala Lys Pro Arg Asn Gln Gly Gly
290                 295                 300

Tyr Gly Gly Ser Ser Ser Ser Ser Tyr Gly Ser Gly Arg Arg Phe
305                 310                 315                 320

<210> SEQ ID NO 20
<211> LENGTH: 538
<212> TYPE: PRT
<213> ORGANISM: Homo sapiens

<400> SEQUENCE: 20

Met Glu Glu Ser Val Asn Gln Met Gln Pro Leu Asn Glu Lys Gln Ile
1               5                   10                  15

Ala Asn Ser Gln Asp Gly Tyr Val Trp Gln Val Thr Asp Met Asn Arg
            20                  25                  30

Leu His Arg Phe Leu Cys Phe Gly Ser Glu Gly Gly Thr Tyr Tyr Ile
        35                  40                  45

Lys Glu Gln Lys Leu Gly Leu Glu Asn Ala Glu Ala Leu Ile Arg Leu
    50                  55                  60

Ile Glu Asp Gly Arg Gly Cys Glu Val Ile Gln Glu Ile Lys Ser Phe
65                  70                  75                  80

Ser Gln Glu Gly Arg Thr Thr Lys Gln Glu Pro Met Leu Phe Ala Leu
                85                  90                  95

Ala Ile Cys Ser Gln Cys Ser Asp Ile Ser Thr Lys Gln Ala Ala Phe
            100                 105                 110

Lys Ala Val Ser Glu Val Cys Arg Ile Pro Thr His Leu Phe Thr Phe
        115                 120                 125

Ile Gln Phe Lys Lys Asp Leu Lys Glu Ser Met Lys Cys Gly Met Trp
130                 135                 140

Gly Arg Ala Leu Arg Lys Ala Ile Ala Asp Trp Tyr Asn Glu Lys Gly
145                 150                 155                 160

Gly Met Ala Leu Ala Leu Ala Val Thr Lys Tyr Lys Gln Arg Asn Gly
                165                 170                 175

Trp Ser His Lys Asp Leu Leu Arg Leu Ser His Leu Lys Pro Ser Ser
            180                 185                 190

Glu Gly Leu Ala Ile Val Thr Lys Tyr Ile Thr Lys Gly Trp Lys Glu
        195                 200                 205

Val His Glu Leu Tyr Lys Glu Lys Ala Leu Ser Val Glu Thr Glu Lys
    210                 215                 220

Leu Leu Lys Tyr Leu Glu Ala Val Glu Lys Val Lys Arg Thr Arg Asp
225                 230                 235                 240

Glu Leu Glu Val Ile His Leu Ile Glu Glu His Arg Leu Val Arg Glu
                245                 250                 255

His Leu Leu Thr Asn His Leu Lys Ser Lys Glu Val Trp Lys Ala Leu
            260                 265                 270

Leu Gln Glu Met Pro Leu Thr Ala Leu Leu Arg Asn Leu Gly Lys Met

```
                  275                 280                 285
        Thr Ala Asn Ser Val Leu Glu Pro Gly Asn Ser Glu Val Ser Leu Val
            290                 295                 300
        Cys Glu Lys Leu Cys Asn Glu Lys Leu Leu Lys Lys Ala Arg Ile His
        305                 310                 315                 320
        Pro Phe His Ile Leu Ile Ala Leu Glu Thr Tyr Lys Thr Gly His Gly
                            325                 330                 335
        Leu Arg Gly Lys Leu Lys Trp Arg Pro Asp Glu Glu Ile Leu Lys Ala
                        340                 345                 350
        Leu Asp Ala Ala Phe Tyr Lys Thr Phe Lys Thr Val Glu Pro Thr Gly
                    355                 360                 365
        Lys Arg Phe Leu Leu Ala Val Asp Val Ser Ala Ser Met Asn Gln Arg
                370                 375                 380
        Val Leu Gly Ser Ile Leu Asn Ala Ser Thr Val Ala Ala Ala Met Cys
        385                 390                 395                 400
        Met Val Val Thr Arg Thr Glu Lys Asp Ser Tyr Val Val Ala Phe Ser
                            405                 410                 415
        Asp Glu Met Val Pro Cys Pro Val Thr Thr Asp Met Thr Leu Gln Gln
                        420                 425                 430
        Val Leu Met Ala Met Ser Gln Ile Pro Ala Gly Gly Thr Asp Cys Ser
                    435                 440                 445
        Leu Pro Met Ile Trp Ala Gln Lys Thr Asn Thr Pro Ala Asp Val Phe
                450                 455                 460
        Ile Val Phe Thr Asp Asn Glu Thr Phe Ala Gly Gly Val His Pro Ala
        465                 470                 475                 480
        Ile Ala Leu Arg Glu Tyr Arg Lys Lys Met Asp Ile Pro Ala Lys Leu
                            485                 490                 495
        Ile Val Cys Gly Met Thr Ser Asn Gly Phe Thr Ile Ala Asp Pro Asp
                        500                 505                 510
        Asp Arg Gly Met Leu Asp Met Cys Gly Phe Asp Thr Gly Ala Leu Asp
                    515                 520                 525
        Val Ile Arg Asn Phe Thr Leu Asp Met Ile
                530                 535

<210> SEQ ID NO 21
<211> LENGTH: 408
<212> TYPE: PRT
<213> ORGANISM: Homo sapiens

<400> SEQUENCE: 21

Met Ala Glu Asn Gly Asp Asn Glu Lys Met Ala Ala Leu Glu Ala Lys
        1               5                   10                  15
        Ile Cys His Gln Ile Glu Tyr Tyr Phe Gly Asp Phe Asn Leu Pro Arg
                            20                  25                  30
        Asp Lys Phe Leu Lys Glu Gln Ile Lys Leu Asp Glu Gly Trp Val Pro
                        35                  40                  45
        Leu Glu Ile Met Ile Lys Phe Asn Arg Leu Asn Arg Leu Thr Thr Asp
                    50                  55                  60
        Phe Asn Val Ile Val Glu Ala Leu Ser Lys Ser Lys Ala Glu Leu Met
        65                  70                  75                  80
        Glu Ile Ser Glu Asp Lys Thr Lys Ile Arg Arg Ser Pro Ser Lys Pro
                            85                  90                  95
        Leu Pro Glu Val Thr Asp Glu Tyr Lys Asn Asp Val Lys Asn Arg Ser
                        100                 105                 110
```

Val Tyr Ile Lys Gly Phe Pro Thr Asp Ala Thr Leu Asp Asp Ile Lys
115                 120                 125

Glu Trp Leu Glu Asp Lys Gly Gln Val Leu Asn Ile Gln Met Arg Arg
130                 135                 140

Thr Leu His Lys Ala Phe Lys Gly Ser Ile Phe Val Val Phe Asp Ser
145                 150                 155                 160

Ile Glu Ser Ala Lys Lys Phe Val Glu Thr Pro Gly Gln Lys Tyr Lys
                165                 170                 175

Glu Thr Asp Leu Leu Ile Leu Phe Lys Asp Asp Tyr Phe Ala Lys Lys
                180                 185                 190

Asn Glu Glu Arg Lys Gln Asn Lys Val Glu Ala Lys Leu Arg Ala Lys
                195                 200                 205

Gln Glu Gln Glu Ala Lys Gln Lys Leu Glu Glu Asp Ala Glu Met Lys
210                 215                 220

Ser Leu Glu Glu Lys Ile Gly Cys Leu Leu Lys Phe Ser Gly Asp Leu
225                 230                 235                 240

Asp Asp Gln Thr Cys Arg Glu Asp Leu His Ile Leu Phe Ser Asn His
                245                 250                 255

Gly Glu Ile Lys Trp Ile Asp Phe Val Arg Gly Ala Lys Glu Gly Ile
                260                 265                 270

Ile Leu Phe Lys Glu Lys Ala Lys Glu Ala Leu Gly Lys Ala Lys Asp
                275                 280                 285

Ala Asn Asn Gly Asn Leu Gln Leu Arg Asn Lys Glu Val Thr Trp Glu
290                 295                 300

Val Leu Glu Gly Glu Val Glu Lys Glu Ala Leu Lys Lys Ile Ile Glu
305                 310                 315                 320

Asp Gln Gln Glu Ser Leu Asn Lys Trp Lys Ser Lys Gly Arg Arg Phe
                325                 330                 335

Lys Gly Lys Gly Lys Gly Asn Lys Ala Ala Gln Pro Gly Ser Gly Lys
                340                 345                 350

Gly Lys Val Gln Phe Gln Gly Lys Lys Thr Lys Phe Ala Ser Asp Asp
                355                 360                 365

Glu His Asp Glu His Asp Glu Asn Gly Ala Thr Gly Pro Val Lys Arg
370                 375                 380

Ala Arg Glu Glu Thr Asp Lys Glu Glu Pro Ala Ser Lys Gln Gln Lys
385                 390                 395                 400

Thr Glu Asn Gly Ala Gly Asp Gln
                405

<210> SEQ ID NO 22
<211> LENGTH: 19
<212> TYPE: RNA
<213> ORGANISM: Artificial Sequence
<220> FEATURE:
<223> OTHER INFORMATION: siRNA

<400> SEQUENCE: 22
guuguauugu uuagcgauu                                                  19

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23

```
gcacuagcca ucucuugcuu c                                              21

<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
uuuauucaua gccguuaaa                                                 19

<210> SEQ ID NO 25
<211> LENGTH: 19
<212> TYPE: RNA
<213> ORGANISM: Artificial Sequence
<220> FEATURE:
<223> OTHER INFORMATION: siRNA

<400> SEQUENCE: 25
uuccuuuaaa ucuuccacc                                                 19

<210> SEQ ID NO 26
<211> LENGTH: 30
<212> TYPE: RNA
<213> ORGANISM: Artificial Sequence
<220> FEATURE:
<223> OTHER INFORMATION: siRNA

<400> SEQUENCE: 26
uugagauaac ucacuaccuu cggaccagcc                                     30

<210> SEQ ID NO 27
<211> LENGTH: 28
<212> TYPE: RNA
<213> ORGANISM: Artificial Sequence
<220> FEATURE:
<223> OTHER INFORMATION: siRNA

<400> SEQUENCE: 27
aagacuaguc aagugcagua gugagaag                                       28

<210> SEQ ID NO 28
<211> LENGTH: 26
<212> TYPE: RNA
<213> ORGANISM: Artificial Sequence
<220> FEATURE:
<223> OTHER INFORMATION: siRNA

<400> SEQUENCE: 28
uaaacaccac uacucucgga ccaacc                                         26

<210> SEQ ID NO 29
<211> LENGTH: 380
<212> TYPE: PRT
<213> ORGANISM: Homo sapiens

<400> SEQUENCE: 29

Met Met Phe Ser Gly Phe Asn Ala Asp Tyr Glu Ala Ser Ser Ser Arg
  1               5                  10                  15

Cys Ser Ser Ala Ser Pro Ala Gly Asp Ser Leu Ser Tyr Tyr His Ser
             20                  25                  30

Pro Ala Asp Ser Phe Ser Ser Met Gly Ser Pro Val Asn Ala Gln Asp
         35                  40                  45
```

-continued

Phe Cys Thr Asp Leu Ala Val Ser Ser Ala Asn Phe Ile Pro Thr Val
    50                  55                  60

Thr Ala Ile Ser Thr Ser Pro Asp Leu Gln Trp Leu Val Gln Pro Ala
65                  70                  75                  80

Leu Val Ser Ser Val Ala Pro Ser Gln Thr Arg Ala Pro His Pro Phe
                85                  90                  95

Gly Val Pro Ala Pro Ser Ala Gly Ala Tyr Ser Arg Ala Gly Val Val
            100                 105                 110

Lys Thr Met Thr Gly Gly Arg Ala Gln Ser Ile Gly Arg Gly Lys
        115                 120                 125

Val Glu Gln Leu Ser Pro Glu Glu Glu Lys Arg Arg Ile Arg Arg
130                 135                 140

Glu Arg Asn Lys Met Ala Ala Lys Cys Arg Asn Arg Arg Arg Glu
145                 150                 155                 160

Leu Thr Asp Thr Leu Gln Ala Glu Thr Asp Gln Leu Glu Asp Glu Lys
                165                 170                 175

Ser Ala Leu Gln Thr Glu Ile Ala Asn Leu Leu Lys Glu Lys Glu Lys
            180                 185                 190

Leu Glu Phe Ile Leu Ala Ala His Arg Pro Ala Cys Lys Ile Pro Asp
        195                 200                 205

Asp Leu Gly Phe Pro Glu Glu Met Ser Val Ala Ser Leu Asp Leu Thr
    210                 215                 220

Gly Gly Leu Pro Glu Val Ala Thr Pro Glu Ser Glu Glu Ala Phe Thr
225                 230                 235                 240

Leu Pro Leu Leu Asn Asp Pro Glu Pro Lys Pro Ser Val Glu Pro Val
                245                 250                 255

Lys Ser Ile Ser Ser Met Glu Leu Lys Thr Glu Pro Phe Asp Asp Phe
            260                 265                 270

Leu Phe Pro Ala Ser Ser Arg Pro Ser Gly Ser Glu Thr Ala Arg Ser
        275                 280                 285

Val Pro Asp Met Asp Leu Ser Gly Ser Phe Tyr Ala Ala Asp Trp Glu
    290                 295                 300

Pro Leu His Ser Gly Ser Leu Gly Met Gly Pro Met Ala Thr Glu Leu
305                 310                 315                 320

Glu Pro Leu Cys Thr Pro Val Val Thr Cys Thr Pro Ser Cys Thr Ala
                325                 330                 335

Tyr Thr Ser Ser Phe Val Phe Thr Tyr Pro Glu Ala Asp Ser Phe Pro
            340                 345                 350

Ser Cys Ala Ala Ala His Arg Lys Gly Ser Ser Ser Asn Glu Pro Ser
        355                 360                 365

Ser Asp Ser Leu Ser Ser Pro Thr Leu Leu Ala Leu
    370                 375                 380

<210> SEQ ID NO 30
<211> LENGTH: 355
<212> TYPE: PRT
<213> ORGANISM: Homo sapiens

<400> SEQUENCE: 30

Met Ala Leu Ser Glu Pro Ile Leu Pro Ser Phe Ser Thr Phe Ala Ser
1               5                   10                  15

Pro Cys Arg Glu Arg Gly Leu Gln Glu Arg Trp Pro Arg Ala Glu Pro
            20                  25                  30

Glu Ser Gly Gly Thr Asp Asp Asp Leu Asn Ser Val Leu Asp Phe Ile
        35                  40                  45

```
Leu Ser Met Gly Leu Asp Gly Leu Gly Ala Glu Ala Ala Pro Glu Pro
             50                  55                  60

Pro Pro Pro Pro Pro Pro Ala Phe Tyr Tyr Pro Glu Pro Gly Ala
 65                  70                  75                  80

Pro Pro Pro Tyr Ser Ala Pro Ala Gly Gly Leu Val Ser Glu Leu Leu
                 85                  90                  95

Arg Pro Glu Leu Asp Ala Pro Leu Gly Pro Ala Leu His Gly Arg Phe
                100                 105                 110

Leu Leu Ala Pro Pro Gly Arg Leu Val Lys Ala Glu Pro Pro Glu Ala
            115                 120                 125

Asp Gly Gly Gly Gly Tyr Gly Cys Ala Pro Gly Leu Thr Arg Gly Pro
            130                 135                 140

Arg Gly Leu Lys Arg Glu Gly Ala Pro Gly Pro Ala Ala Ser Cys Met
145                 150                 155                 160

Arg Gly Pro Gly Gly Arg Pro Pro Pro Asp Thr Pro Pro Leu
                165                 170                 175

Ser Pro Asp Gly Pro Ala Arg Leu Pro Ala Pro Gly Pro Arg Ala Ser
            180                 185                 190

Phe Pro Pro Pro Phe Gly Gly Pro Gly Phe Gly Ala Pro Gly Pro Gly
            195                 200                 205

Leu His Tyr Ala Pro Pro Ala Pro Pro Ala Phe Gly Leu Phe Asp Asp
        210                 215                 220

Ala Ala Ala Ala Ala Ala Leu Gly Leu Ala Pro Pro Ala Ala Arg
225                 230                 235                 240

Gly Leu Leu Thr Pro Pro Ala Ser Pro Leu Glu Leu Leu Glu Ala Lys
                245                 250                 255

Pro Lys Arg Gly Arg Arg Ser Trp Pro Arg Lys Arg Thr Ala Thr His
            260                 265                 270

Thr Cys Ser Tyr Ala Gly Cys Gly Lys Thr Tyr Thr Lys Ser Ser His
            275                 280                 285

Leu Lys Ala His Leu Arg Thr His Thr Gly Glu Lys Pro Tyr His Cys
        290                 295                 300

Asn Trp Asp Gly Cys Gly Trp Lys Phe Ala Arg Ser Asp Glu Leu Thr
305                 310                 315                 320

Arg His Tyr Arg Lys His Thr Gly His Arg Pro Phe Gln Cys His Leu
                325                 330                 335

Cys Asp Arg Ala Phe Ser Arg Ser Asp His Leu Ala Leu His Met Lys
            340                 345                 350

Arg His Met
        355

<210> SEQ ID NO 31
<211> LENGTH: 887
<212> TYPE: PRT
<213> ORGANISM: Homo sapiens

<400> SEQUENCE: 31

Met Met Asn Arg Phe Arg Lys Trp Leu Tyr Lys Pro Lys Arg Ser Asp
  1               5                  10                  15

Pro Gln Leu Leu Ala Arg Phe Tyr Tyr Ala Asp Glu Glu Leu Asn Gln
             20                  25                  30

Val Ala Ala Glu Leu Asp Ser Leu Asp Gly Arg Lys Asp Pro Gln Arg
         35                  40                  45

Cys Thr Leu Leu Val Ser Gln Phe Arg Ser Cys Gln Asp Asn Val Leu
```

-continued

```
                  50                  55                  60
Asn Ile Ile Asn Gln Ile Met Asp Glu Cys Ile Pro Gln Asp Arg Ala
 65                  70                  75                  80

Pro Arg Asp Phe Cys Val Lys Phe Pro Glu Glu Ile Arg His Asp Asn
                 85                  90                  95

Leu Ala Gly Gln Leu Trp Phe Gly Ala Glu Cys Leu Ala Ala Gly Ser
                100                 105                 110

Ile Ile Met Asn Arg Glu Leu Glu Ser Met Ala Met Arg Pro Leu Ala
                115                 120                 125

Lys Glu Leu Thr Arg Ser Leu Glu Asp Val Arg Gly Ala Leu Arg Asp
    130                 135                 140

Gln Ala Leu Arg Asp Leu Asn Thr Tyr Thr Glu Lys Met Arg Glu Ala
145                 150                 155                 160

Leu Arg His Phe Asp Val Leu Phe Ala Glu Phe Glu Leu Ser Tyr Val
                165                 170                 175

Ser Ala Met Val Pro Val Lys Ser Pro Arg Glu Tyr Tyr Val Gln Gln
                180                 185                 190

Glu Val Ile Val Leu Phe Cys Glu Thr Val Glu Arg Ala Leu Asp Phe
    195                 200                 205

Gly Tyr Leu Thr Gln Asp Met Ile Asp Asp Tyr Glu Pro Ala Leu Met
    210                 215                 220

Phe Ser Ile Pro Arg Leu Ala Ile Val Cys Gly Leu Val Val Tyr Ala
225                 230                 235                 240

Asp Gly Pro Leu Asn Leu Asp Arg Lys Val Glu Asp Met Ser Glu Leu
                245                 250                 255

Phe Arg Pro Phe His Thr Leu Leu Arg Lys Ile Arg Asp Leu Leu Gln
                260                 265                 270

Thr Leu Thr Glu Glu Leu His Thr Leu Glu Arg Asn Leu Cys Ile
                275                 280                 285

Ser Gln Asp Val Glu Phe Pro Ile Arg Ala Asp Val Gln Gly Pro Ala
    290                 295                 300

Ala Leu Ala Pro Ala Leu Ser Ala Pro Leu Pro Glu Gly Pro Leu
305                 310                 315                 320

Ser Ala Lys Ala Lys Asp Pro Asp Ala Glu Leu Ala Cys Ser Met Gln
                325                 330                 335

Tyr Asp Asp Gln Glu Leu Glu Gln Leu Ser Arg Met Val His Arg Ala
                340                 345                 350

Gly Asp Glu Met Ser Ser Leu Leu Ser Pro Ile Ala Cys Gln Ser
                355                 360                 365

Pro Ala His Arg Pro Gly Ala Glu Gly Ser Pro Gly Gly Glu Ala Ser
    370                 375                 380

Pro Gly Arg Pro Arg Leu Arg Ser Gly Ser Asp Glu Glu Arg Val
385                 390                 395                 400

Phe Phe Met Asp Asp Val Glu Gly Thr Ala Glu Ala Leu Ala Arg Pro
                405                 410                 415

Glu Ser Pro Ala Gly Pro Phe Gly Trp Ala Gly Ser Thr Trp Ala Asp
                420                 425                 430

Pro Gln Glu Lys Gly Gln Gly Gly Pro Gly Ala Ala Gly Ile Ser
                435                 440                 445

Leu Pro Ala Ser Glu Lys Glu Glu Asp Leu Ser Asn Asn Asn Leu Glu
    450                 455                 460

Ala Glu Gly Thr Asp Gly Ala Ser Leu Ala Gly Thr Ser Ser Cys Ser
465                 470                 475                 480
```

```
Cys Leu Asp Ser Arg Leu His Leu Asp Gly Trp Glu Val Gly Ala Asp
            485                 490                 495

Asp Ala Glu Thr Ala Glu Met Ile Ala His Arg Thr Gly Gly Met Lys
        500                 505                 510

Leu Ser Ala Thr Val Ile Phe Asn Pro Lys Ser Pro Thr Ser Leu Asp
        515                 520                 525

Ser Ala Val Ala Thr Gln Glu Ala Ala Ser Glu Pro Val Ala Glu Gly
    530                 535                 540

Met Asp Gly Gly Pro His Lys Leu Ser Thr Gly Ala Thr Asn Cys Leu
545                 550                 555                 560

Leu His Ser Cys Val Cys Cys Gly Ser Cys Gly Asp Ser Arg Glu Asp
                565                 570                 575

Val Val Glu Arg Leu Arg Glu Lys Cys Ser Pro Gly Gly Val Ile Gly
            580                 585                 590

Ala Ser Tyr Ala Ala Gly Leu Ala Lys Ala Ser Asp Arg Ala Pro Glu
        595                 600                 605

Arg Gln Glu Glu Ala Pro Pro Ser Glu Asp Ala Ser Asn Gly Arg
        610                 615                 620

Glu Pro Lys Ala Pro Thr Ser Asp Lys Cys Leu Pro His Thr Ser Gly
625                 630                 635                 640

Ser Gln Val Asp Thr Ala Ser Gly Leu Gln Gly Glu Ala Gly Val Ala
                645                 650                 655

Gly Gln Gln Glu Pro Glu Ala Arg Glu Leu His Ala Gly Ser Pro Pro
            660                 665                 670

Ala His Glu Ala Pro Gln Ala Leu Ser Gly Ser Ser Ser Thr Ala
        675                 680                 685

Gly Ser Cys Ser Ser Asp Lys Met Gly Pro Glu Ala Ala Pro Ala Ala
690                 695                 700

Thr His Ala Ala Pro Gln Ala Thr Arg Glu Lys Ile Arg Ser Arg Phe
705                 710                 715                 720

His Gly Ser His Asp Leu Ile His Arg Leu Phe Val Cys Ile Ser Gly
                725                 730                 735

Val Ala Asp Gln Leu Gln Thr Asn Tyr Ala Ser Asp Leu Arg Ser Ile
            740                 745                 750

Leu Lys Thr Leu Phe Glu Val Met Ala Thr Lys Pro Glu Thr Asp Asp
        755                 760                 765

Lys Glu Lys Leu Arg Lys Val Thr Gln Thr Leu Arg Ser Ala Ala Leu
770                 775                 780

Glu Asp Cys Ala Leu Cys Gln Glu Thr Leu Ser Ser Ser Glu Leu Ala
785                 790                 795                 800

Ala Lys Thr Arg Asp Gly Asp Phe Glu Asp Pro Pro Glu Trp Val Pro
            805                 810                 815

Asp Glu Ala Cys Gly Phe Cys Thr Ala Cys Lys Ala Pro Phe Thr Val
        820                 825                 830

Ile Arg Arg Lys His His Cys Arg Ser Cys Gly Lys Ile Phe Cys Ser
        835                 840                 845

Arg Cys Ser Ser His Ser Ala Pro Leu Pro Arg Tyr Gly Gln Val Lys
    850                 855                 860

Pro Val Arg Val Cys Thr His Cys Tyr Met Phe His Val Thr Pro Phe
865                 870                 875                 880

Tyr Ser Asp Lys Ala Gly Leu
            885
```

<210> SEQ ID NO 32
<211> LENGTH: 855
<212> TYPE: PRT
<213> ORGANISM: Homo sapiens

<400> SEQUENCE: 32

Met Ser Glu Ala Arg Arg Asp Ser Thr Ser Ser Leu Gln Arg Lys Lys
1               5                   10                  15

Pro Pro Trp Leu Lys Leu Asp Ile Pro Ser Ala Val Pro Leu Thr Ala
            20                  25                  30

Glu Glu Pro Ser Phe Leu Gln Pro Leu Arg Arg Gln Ala Phe Leu Arg
        35                  40                  45

Ser Val Ser Met Pro Ala Glu Thr Ala His Ile Ser Ser Pro His His
    50                  55                  60

Glu Leu Arg Arg Pro Val Leu Gln Arg Gln Thr Ser Ile Thr Gln Thr
65                  70                  75                  80

Ile Arg Arg Gly Thr Ala Asp Trp Phe Gly Val Ser Lys Asp Ser Asp
                85                  90                  95

Ser Thr Gln Lys Trp Gln Arg Lys Ser Ile Arg His Cys Ser Gln Arg
            100                 105                 110

Tyr Gly Lys Leu Lys Pro Gln Val Leu Arg Glu Leu Asp Leu Pro Ser
        115                 120                 125

Gln Asp Asn Val Ser Leu Thr Ser Thr Glu Thr Pro Pro Pro Leu Tyr
    130                 135                 140

Val Gly Pro Cys Gln Leu Gly Met Gln Lys Ile Ile Asp Pro Leu Ala
145                 150                 155                 160

Arg Gly Arg Ala Phe Arg Val Ala Asp Asp Thr Ala Glu Gly Leu Ser
                165                 170                 175

Ala Pro His Thr Pro Val Thr Pro Gly Ala Ala Ser Leu Cys Ser Phe
            180                 185                 190

Ser Ser Ser Arg Ser Gly Phe His Arg Leu Pro Arg Arg Arg Lys Arg
        195                 200                 205

Glu Ser Val Ala Lys Met Ser Phe Arg Ala Ala Ala Leu Met Lys
    210                 215                 220

Gly Arg Ser Val Arg Asp Gly Thr Phe Arg Arg Ala Gln Arg Ser
225                 230                 235                 240

Phe Thr Pro Ala Ser Phe Leu Glu Glu Asp Thr Thr Asp Phe Pro Asp
                245                 250                 255

Glu Leu Asp Thr Ser Phe Phe Ala Arg Glu Gly Ile Leu His Glu Glu
            260                 265                 270

Leu Ser Thr Tyr Pro Asp Glu Val Phe Glu Ser Pro Ser Glu Ala Ala
        275                 280                 285

Leu Lys Asp Trp Glu Lys Ala Pro Glu Gln Ala Asp Leu Thr Gly Gly
    290                 295                 300

Ala Leu Asp Arg Ser Glu Leu Glu Arg Ser His Leu Met Leu Pro Leu
305                 310                 315                 320

Glu Arg Gly Trp Arg Lys Gln Lys Glu Gly Ala Ala Ala Pro Gln Pro
                325                 330                 335

Lys Val Arg Leu Arg Gln Glu Val Val Ser Thr Ala Gly Pro Arg Arg
            340                 345                 350

Gly Gln Arg Ile Ala Val Pro Val Arg Lys Leu Phe Ala Arg Glu Lys
        355                 360                 365

Arg Pro Tyr Gly Leu Gly Met Val Gly Arg Leu Thr Asn Arg Thr Tyr
    370                 375                 380

```
Arg Lys Arg Ile Asp Ser Phe Val Lys Arg Gln Ile Glu Asp Met Asp
385                 390                 395                 400

Asp His Arg Pro Phe Thr Tyr Trp Leu Thr Phe Val His Ser Leu
            405                 410                 415

Val Thr Ile Leu Ala Val Cys Ile Tyr Gly Ile Ala Pro Val Gly Phe
        420                 425                 430

Ser Gln His Glu Thr Val Asp Ser Val Leu Arg Asn Arg Gly Val Tyr
            435                 440                 445

Glu Asn Val Lys Tyr Val Gln Gln Glu Asn Phe Trp Ile Gly Pro Ser
            450                 455                 460

Ser Glu Ala Leu Ile His Leu Gly Ala Lys Phe Ser Pro Cys Met Arg
465                 470                 475                 480

Gln Asp Pro Gln Val His Ser Phe Ile Arg Ser Ala Arg Glu Arg Glu
                485                 490                 495

Lys His Ser Ala Cys Cys Val Arg Asn Asp Arg Ser Gly Cys Val Gln
                500                 505                 510

Thr Ser Glu Glu Glu Cys Ser Ser Thr Leu Ala Val Trp Val Lys Trp
            515                 520                 525

Pro Ile His Pro Ser Ala Pro Glu Leu Ala Gly His Lys Arg Gln Phe
        530                 535                 540

Gly Ser Val Cys His Gln Asp Pro Arg Val Cys Asp Glu Pro Ser Ser
545                 550                 555                 560

Glu Asp Pro His Glu Trp Pro Glu Asp Ile Thr Lys Trp Pro Ile Cys
                565                 570                 575

Thr Lys Asn Ser Ala Gly Asn His Thr Asn His Pro His Met Asp Cys
            580                 585                 590

Val Ile Thr Gly Arg Pro Cys Cys Ile Gly Thr Lys Gly Arg Cys Glu
            595                 600                 605

Ile Thr Ser Arg Glu Tyr Cys Asp Phe Met Arg Gly Tyr Phe His Glu
        610                 615                 620

Glu Ala Thr Leu Cys Ser Gln Val His Cys Met Asp Asp Val Cys Gly
625                 630                 635                 640

Leu Leu Pro Phe Leu Asn Pro Glu Val Pro Asp Gln Phe Tyr Arg Leu
                645                 650                 655

Trp Leu Ser Leu Phe Leu His Ala Gly Ile Leu His Cys Leu Val Ser
            660                 665                 670

Ile Cys Phe Gln Met Thr Val Leu Arg Asp Leu Glu Lys Leu Ala Gly
        675                 680                 685

Trp His Arg Ile Ala Ile Ile Tyr Leu Leu Ser Gly Val Thr Gly Asn
            690                 695                 700

Leu Ala Ser Ala Ile Phe Leu Pro Tyr Arg Ala Glu Val Gly Pro Ala
705                 710                 715                 720

Gly Ser Gln Phe Gly Ile Leu Ala Cys Leu Phe Val Glu Leu Phe Gln
                725                 730                 735

Ser Trp Gln Ile Leu Ala Arg Pro Trp Arg Ala Phe Phe Lys Leu Leu
            740                 745                 750

Ala Val Val Leu Phe Leu Phe Thr Phe Gly Leu Leu Pro Trp Ile Asp
                755                 760                 765

Asn Phe Ala His Ile Ser Gly Phe Ile Ser Gly Leu Phe Leu Ser Phe
            770                 775                 780

Ala Phe Leu Pro Tyr Ile Ser Phe Gly Lys Phe Asp Leu Tyr Arg Lys
785                 790                 795                 800
```

```
Arg Cys Gln Ile Ile Ile Phe Gln Val Val Phe Leu Gly Leu Leu Ala
                805                 810                 815

Gly Leu Val Val Leu Phe Tyr Val Tyr Pro Val Arg Cys Glu Trp Cys
            820                 825                 830

Glu Phe Leu Thr Cys Ile Pro Phe Thr Asp Lys Phe Cys Glu Lys Tyr
            835                 840                 845

Glu Leu Asp Ala Gln Leu His
            850                 855

<210> SEQ ID NO 33
<211> LENGTH: 822
<212> TYPE: PRT
<213> ORGANISM: Homo sapiens

<400> SEQUENCE: 33

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320
```

-continued

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Tyr Cys Thr Gly Ala
370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
            645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Arg Asp Cys
            725                 730                 735

```
Trp His Ala Val Pro Ser Gln Arg Pro Thr Phe Lys Gln Leu Val Glu
                740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
        770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820

<210> SEQ ID NO 34
<211> LENGTH: 417
<212> TYPE: PRT
<213> ORGANISM: Homo sapiens

<400> SEQUENCE: 34

Met Arg Phe Ala Trp Thr Val Leu Leu Leu Gly Pro Leu Gln Leu Cys
1               5                   10                  15

Ala Leu Val His Cys Ala Pro Pro Ala Gly Gln Gln Gln Pro Pro
                20                  25                  30

Arg Glu Pro Pro Ala Ala Pro Gly Ala Trp Arg Gln Gln Ile Gln Trp
            35                  40                  45

Glu Asn Asn Gly Gln Val Phe Ser Leu Leu Ser Leu Gly Ser Gln Tyr
        50                  55                  60

Gln Pro Gln Arg Arg Arg Asp Pro Gly Ala Ala Val Pro Gly Ala Ala
65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
            100                 105                 110

Thr Ala Gly Arg Pro Arg Pro Thr Ala Arg His Trp Phe Gln Ala Gly
        115                 120                 125

Tyr Ser Thr Ser Arg Ala Arg Glu Ala Gly Ala Ser Arg Ala Glu Asn
130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Pro Tyr Asn Pro Tyr Lys
                165                 170                 175

Tyr Ser Asp Asp Asn Pro Tyr Tyr Asn Tyr Tyr Asp Thr Tyr Glu Arg
            180                 185                 190

Pro Arg Pro Gly Gly Arg Tyr Arg Pro Gly Tyr Gly Thr Gly Tyr Phe
        195                 200                 205

Gln Tyr Gly Leu Pro Asp Leu Val Ala Asp Pro Tyr Tyr Ile Gln Ala
    210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
            260                 265                 270

Gly Thr Ser Asp Phe Leu Pro Ser Arg Pro Arg Tyr Ser Trp Glu Trp
        275                 280                 285
```

His Ser Cys His Gln His Tyr His Ser Met Asp Glu Phe Ser His Tyr
    290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
                340                 345                 350

Asp Thr Tyr Gly Ala Asp Ile Asp Cys Gln Trp Ile Asp Ile Thr Asp
                355                 360                 365

Val Lys Pro Gly Asn Tyr Ile Leu Lys Val Ser Val Asn Pro Ser Tyr
    370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 35
<211> LENGTH: 598
<212> TYPE: PRT
<213> ORGANISM: Homo sapiens

<400> SEQUENCE: 35

Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
                20                  25                  30

Pro Thr Met Asp Leu Ala Ser Pro Glu Ala Ala Pro Ala Ala Pro Thr
            35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
            115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
    195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
            245                 250                 255

Ser Gly Ala Pro Gly Gly Ser Glu Gly Arg Cys Ala Val Cys Gly Asp
        260                 265                 270

Asn Ala Ser Cys Gln His Tyr Gly Val Arg Thr Cys Glu Gly Cys Lys
            275                 280                 285

Gly Phe Phe Lys Arg Thr Val Gln Lys Asn Ala Lys Tyr Ile Cys Leu
    290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
        355                 360                 365

Val Arg Ala His Leu Asp Ser Gly Pro Ser Thr Ala Lys Leu Asp Tyr
    370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
            420                 425                 430

Ala Asp Gln Asp Leu Leu Leu Glu Ser Ala Phe Leu Glu Leu Phe Ile
        435                 440                 445

Leu Arg Leu Ala Tyr Arg Ser Lys Pro Gly Glu Gly Lys Leu Ile Phe
    450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
        515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
            580                 585                 590

Met Asp Thr Leu Pro Phe
        595

<210> SEQ ID NO 36
<211> LENGTH: 50
<212> TYPE: DNA
<213> ORGANISM: Artificial sequence
<220> FEATURE:
<223> OTHER INFORMATION: Primer

<400> SEQUENCE: 36
gtcgtatcca gtgcagggtc cgaggtattc gcactggata cgacattgag        50

<210> SEQ ID NO 37
<211> LENGTH: 50
<212> TYPE: DNA
<213> ORGANISM: Artificial sequence
<220> FEATURE:
<223> OTHER INFORMATION: Primer

<400> SEQUENCE: 37
gtcgtatcca gtgcagggtc cgaggtattc gcactggata cgacaacacc        50

<210> SEQ ID NO 38
<211> LENGTH: 50
<212> TYPE: DNA
<213> ORGANISM: Artificial sequence
<220> FEATURE:
<223> OTHER INFORMATION: Primer

<400> SEQUENCE: 38
gtcgtatcca gtgcagggtc cgaggtattc gcactggata cgacagttgt        50

<210> SEQ ID NO 39
<211> LENGTH: 50
<212> TYPE: DNA
<213> ORGANISM: Artificial sequence
<220> FEATURE:
<223> OTHER INFORMATION: Primer

<400> SEQUENCE: 39
gtcgtatcca gtgcagggtc cgaggtattc gcactggata cgacagttct        50

<210> SEQ ID NO 40
<211> LENGTH: 16
<212> TYPE: DNA
<213> ORGANISM: Artificial sequence
<220> FEATURE:
<223> OTHER INFORMATION: Primer

<400> SEQUENCE: 40
gtgcagggtc cgaggt        16

<210> SEQ ID NO 41
<211> LENGTH: 19
<212> TYPE: DNA
<213> ORGANISM: Artificial sequence
<220> FEATURE:
<223> OTHER INFORMATION: Primer

<400> SEQUENCE: 41
tggtccgaag gtagtgagt        19

<210> SEQ ID NO 42
<211> LENGTH: 19
<212> TYPE: DNA
<213> ORGANISM: Artificial sequence
<220> FEATURE:
<223> OTHER INFORMATION: Primer

<400> SEQUENCE: 42
ttggtccgag agtagtggt        19

<210> SEQ ID NO 43
<211> LENGTH: 20
<212> TYPE: DNA

<213> ORGANISM: Artificial sequence
<220> FEATURE:
<223> OTHER INFORMATION: Primer

<400> SEQUENCE: 43
tccgagtgca gtggtgttta                                                    20

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
ggtccgatgg tagtgggtta t                                                  21

<210> SEQ ID NO 45
<211> LENGTH: 72
<212> TYPE: DNA
<213> ORGANISM: Artificial sequence
<220> FEATURE:
<223> OTHER INFORMATION: Primer

<400> SEQUENCE: 45
aaggcgcatc tgcgtacaca cacaggtgag aagcctaagg cgcatctgcg tacacacaca        60
ggtgagaagc ct                                                            72

<210> SEQ ID NO 46
<211> LENGTH: 72
<212> TYPE: DNA
<213> ORGANISM: Artificial sequence
<220> FEATURE:
<223> OTHER INFORMATION: Primer

<400> SEQUENCE: 46
aaggcgcatc tgcgtacaca cacagagtga ggacctaagg cgcatctgcg tacacacaca        60
gagtgaggac ct                                                            72

<210> SEQ ID NO 47
<211> LENGTH: 19
<212> TYPE: DNA
<213> ORGANISM: Artificial sequence
<220> FEATURE:
<223> OTHER INFORMATION: Primer

<400> SEQUENCE: 47
actcactacc ttcggacca                                                     19

<210> SEQ ID NO 48
<211> LENGTH: 19
<212> TYPE: DNA
<213> ORGANISM: Artificial sequence
<220> FEATURE:
<223> OTHER INFORMATION: Primer

<400> SEQUENCE: 48
agtcaagtgc agtagtgag                                                     19

<210> SEQ ID NO 49
<211> LENGTH: 19
<212> TYPE: DNA
<213> ORGANISM: Artificial sequence
<220> FEATURE:
<223> OTHER INFORMATION: Primer

```
<400> SEQUENCE: 49
ttcaatctgt aactgactg                                                    19

<210> SEQ ID NO 50
<211> LENGTH: 19
<212> TYPE: DNA
<213> ORGANISM: Artificial sequence
<220> FEATURE:
<223> OTHER INFORMATION: Primer

<400> SEQUENCE: 50
accactactc tcggaccaa                                                    19

<210> SEQ ID NO 51
<211> LENGTH: 19
<212> TYPE: DNA
<213> ORGANISM: Artificial sequence
<220> FEATURE:
<223> OTHER INFORMATION: Primer

<400> SEQUENCE: 51
ctggtcaagt gaagcagtg                                                    19

<210> SEQ ID NO 52
<211> LENGTH: 19
<212> TYPE: DNA
<213> ORGANISM: Artificial sequence
<220> FEATURE:
<223> OTHER INFORMATION: Primer

<400> SEQUENCE: 52
cccactacca tcggaccag                                                    19

<210> SEQ ID NO 53
<211> LENGTH: 38
<212> TYPE: DNA
<213> ORGANISM: Artificial sequence
<220> FEATURE:
<223> OTHER INFORMATION: Primer

<400> SEQUENCE: 53
cgttccaatt ttagtatatg tgctgccgaa gcgagcac                               38

<210> SEQ ID NO 54
<211> LENGTH: 32
<212> TYPE: RNA
<213> ORGANISM: Artificial Sequence
<220> FEATURE:
<223> OTHER INFORMATION: siRNA

<400> SEQUENCE: 54
aguucugaua acccacuacc aucggaccag cc                                     32

<210> SEQ ID NO 55
<211> LENGTH: 21
<212> TYPE: RNA
<213> ORGANISM: Artificial Sequence
<220> FEATURE:
<223> OTHER INFORMATION: siRNA

<400> SEQUENCE: 55
uucagcucga uggauauggu g                                                 21
```

```
<210> SEQ ID NO 56
<211> LENGTH: 19
<212> TYPE: RNA
<213> ORGANISM: Artificial Sequence
<220> FEATURE:
<223> OTHER INFORMATION: siRNA

<400> SEQUENCE: 56
cagucaguua cagauugaa                                                  19

<210> SEQ ID NO 57
<211> LENGTH: 19
<212> TYPE: RNA
<213> ORGANISM: Artificial Sequence
<220> FEATURE:
<223> OTHER INFORMATION: siRNA

<400> SEQUENCE: 57
caaccaguua cagauuucu                                                  19

<210> SEQ ID NO 58
<211> LENGTH: 24
<212> TYPE: RNA
<213> ORGANISM: Artificial Sequence
<220> FEATURE:
<223> OTHER INFORMATION: siRNA

<400> SEQUENCE: 58
cuucucacua cugcacuuga cuag                                            24

<210> SEQ ID NO 59
<211> LENGTH: 33
<212> TYPE: RNA
<213> ORGANISM: Artificial Sequence
<220> FEATURE:
<223> OTHER INFORMATION: siRNA

<400> SEQUENCE: 59
ggcgcaucug cguacacaca caggugagaa gcc                                  33

<210> SEQ ID NO 60
<211> LENGTH: 37
<212> TYPE: RNA
<213> ORGANISM: Mus musculus

<400> SEQUENCE: 60
aaggcgcauc ugcguacaca cacaggugag aagccuu                              37

<210> SEQ ID NO 61
<211> LENGTH: 37
<212> TYPE: RNA
<213> ORGANISM: Rattus norvegicus

<400> SEQUENCE: 61
aaggcgcauc ugaggacgca cacaggugag aagccuu                              37

<210> SEQ ID NO 62
<211> LENGTH: 37
<212> TYPE: RNA
<213> ORGANISM: Xenopus borealis

<400> SEQUENCE: 62
aaagcccauc ucagaaccca cacaggugag aagccuu                              37
```

```
<210> SEQ ID NO 63
<211> LENGTH: 37
<212> TYPE: RNA
<213> ORGANISM: Homo sapiens

<400> SEQUENCE: 63
gcuuacucuc gcccccuccc ugcaggugag aagcccu                              37
```

RNY-DERIVED SMALL RNAS AS BIOMARKERS FOR ATHEROSCLEROSIS-RELATED DISORDERS

The present invention concerns an in vitro method of diagnosis or prognosis of an atherosclerosis-related disorder by detecting a small Y RNA (s-RNY), as well as the use of an inhibitor of s-RNY as a medicament against atherosclerosis-related disorders. The invention also concerns a method for screening for a compound suitable for the treatment of an atherosclerosis-related disorder.

BACKGROUND TO THE INVENTION

The discovery of regulatory small RNAs is among the most significant biomedical breakthroughs in recent history. To date, three major classes of small RNAs have been identified, namely the microRNA (miRNA), the small-interfering RNA (sRNA), and the piwi-interacting RNA (piRNA). These classes differ in their biogenesis, their length, and their tissue distribution (Ghildiyal, M., and Zamore, P. D. (2009). Nat Rev Genet 10, 94-108; Kim, V. N. et al (2009). Nature reviews 10, 126-139). miRNAs are ~22 nucleotides (nt) in length and are generated from hairpin-shaped primary transcripts by two sequential processing steps mediated by a nuclear (Drosha) and a cytoplasmic (Dicer) RNAse III endonuclease. miRNAs are loaded in RISC (RNA-induced silencing complex), which main component is Argonaute 2 (Ago2), to mediate degradation and/or translation block of specific target messenger RNAs (mRNAs) via Watson-Crick base pairing partial sequence complementarity (Fabian, M. R., et al. (2010). Annual review of biochemistry 79, 351-379). miRNAs are ubiquitinously expressed and control a wide range of cellular activities, including development, immune function, and cell death (Fabian, M. R., et al. (2010). Annual review of biochemistry 79, 351-379). siRNAs derive from double stranded-RNAs that are processed by Dicer into 19 nt small RNAs. siRNAs are also incorporated in RISC to post-transcriptionally silence specific target mRNAs in stem-cells (Ghildiyal, M., and Zamore, P. D. (2009). Nat Rev Genet 10, 94-108). piRNAs derive from single stranded-RNAs that are processed by a poorly understood mechanism into 24-30 nt small RNAs. piRNAs mediate both epigenetic and post-transcriptional gene silencing of retrotransposons and other genetic elements in germ cells (Ghildiyal, M., and Zamore, P. D. (2009). Nat Rev Genet 10, 94-108). Importantly, recent analyses of data coming from next generation sequencing technologies, also known as deep or high-throughput sequencing, from cell cultures and tissues have revealed the existence of other classes of small RNAs, including those from sno-RNAs and tRNAs or from Alu repeats. Overall, these findings suggest that cells may generate a wide range of regulatory small RNAs with a broad variety of processing mechanisms and functions.

The inventors have explored whether atherogenic stimuli regulate the expression of novel regulatory small RNAs, which in turn may modulate apoptosis and inflammation in macrophages. Atherosclerosis is caused by an artery wall thickening, also known as lesion, as a result of the accumulation of lipids, cells, and extracellular matrix in the area between the endothelium and the underlying smooth muscle cells (Moore, K. J., and Tabas, I. (2011). Cell 145, 341-355). A key initiating step of atherosclerosis is the subendothelial accumulation of ApoB-LPs (apolipoprotein B-containing lipoproteins) composed of cholesteryl fatty acyl esters and triglycerides, which are transported in the blood as LDL (Low-density lipoprotein) (Moore, K. J., and Tabas, I. (2011). Cell 145, 341-355). Activation of endothelial cells by ApoB-LPs leads to the recruitment of macrophages, which play a major role all along atherosclerosis from the early phases of lesion formation to the advanced ones. Indeed, in early phases, macrophages engulf lipoproteins and lipids, and become the so-called foam cells, which secrete inflammatory cytokines and undergo apoptosis. Rapid efferocytic clearance of the apoptotic foam cells leads to suppression of the inflammatory response ultimately retarding lesion progression. However, in advanced lesions, macrophage apoptosis is not properly coupled with phagocytic clearance leading to the necrotic plaque formation. The build-up of necrotic debris ultimately promotes inflammation, plaque disruption, and eventually thrombosis. Both macrophage death rate and efficiency of apoptotic cell clearance are processes that control lesion progression (Moore, K. J., and Tabas, I. (2011). Cell 145, 341-355). Induction of macrophage apoptosis in atherosclerotic lesions involves the chronic and cumulative effect of several features including oxidant stress, cytokines, oxidized LDL (oxLDL), activation of Fas death pathway, saturated fatty acids, and endoplasmic reticulum stressors (Moore, K. J., and Tabas, I. (2011). Cell 145, 341-355). Therefore, understanding the molecular mechanisms underlying apoptosis in macrophages upon atheroma-relevant stimuli is a key goal in deciphering lesion progression.

The inventors have shown that, in macrophages stimulated with atherogenic lipids, RNYs (also called "Y RNAs") are processed into small RNAs which are about 24-34 nucleotide (nt) long and are referred to as small-RNYs (s-RNYs). These s-RNYs cause the degradation of a subset of mRNAs crucial for atherogenesis and ultimately modulate apoptosis and inflammatory response in lipid-laden macrophages.

RNYs are ~110 nt long cytoplasmic, non-coding RNAs that are characterized by extensive base-pairing of the 5' and 3' regions and by the association with the proteins Ro60 and La/SSB to form the Ro ribonucleoprotein complex. In macrophages incubated with atherogenic stimuli, such as palmitic acid (PA), generation of s-RNYs requires Ago2 and the single-stranded RNA binding protein hnRNP A1 which is the most abundant core proteins of the ribonucleoprotein complex. hnRNP A1 shuttles to the cytoplasm to directly bind RNYs and modulate the positioning/recruitment of Ago2 which in turn participates into the catalysis and maturation of RNYs into s-RNYs.

s-RNYs regulate pro-inflammatory and pro-apoptotic pathways in lipid-laden macrophages by controlling the expression levels of a subset of transcripts which are critical in regulating the pathogenesis of atherosclerosis, such as Fos, KLF2, and Nr4a1. Importantly, s-RNYs are responsible, at least in part, for the activation of p38 and NF-κB signaling pathways in PA-treated macrophages, ultimately promoting cell death and inflammatory response.

In accordance the above finding that s-RNYs are the main small RNAs regulating immune response in the pathogenesis of atherosclerosis, a significant increase of s-RNY expression was demonstrated in mouse models for atherosclerosis and in the serum of a cohort of patients with stable coronary artery disease (CAD). Furthermore, sRNY expression levels in CAD patients were positively correlated with pro-atherogenic lipids and inflammatory condition, while negative association was found with atheroprotective HDL.

Altogether, the inventor's results indicate that s-RNY expression can be used as a diagnostic marker and a therapeutic target for atherosclerosis.

DESCRIPTION OF THE INVENTION

Method of Diagnosis or Prognosis of an Atherosclerosis-Related Disorder

The invention concerns an in vitro method of diagnosis or prognosis of an atherosclerosis-related disorder in an individual, which comprises the steps of:
a) determining the level of expression of at least one biomarker consisting of a small Y RNA (s-RNY) in a biological sample of said individual,
b) comparing the level of expression of said at least one biomarker with a reference value,
c) deducing from said comparison if the individual has developed or is at risk of developing an atherosclerosis-related disorder.

The invention also concerns the use of at least one small Y RNA (s-RNY) as a biomarker of atherosclerosis-related disorders.

As used herein, an "atherosclerosis-related disorder" is a disease that results from the development of atherosclerosis in any artery in the body, including arteries in the heart, brain, arms, legs, pelvis, and kidneys. An atherosclerosis-related disorder can be, for example, chronic kidney disease, cerebrovascular disease, peripheral vascular disease, ischemic heart disease, carotid artery disease, or coronary artery disease (also called coronary heart disease (CHD)).

An atherosclerosis-related disorder is usually diagnosed by angiography when severe narrowing (stenosis) of artery is already present, and to a lesser extent by cardiac stress testing. Earlier detection of atherosclerosis-related disorder currently relies on anatomical detection such as coronary calcium scoring by computed tomography, carotid intimal media thickness (IMT) measurement by ultrasound, and intravascular ultrasound (IVUS) imaging, and/or physiologic measurement such as lipoprotein subclass analysis, or measurement of HbA1c, hs-CRP, and/or homocysteine.

The term "diagnosing" or "diagnosis" or "diagnostic" is used herein to refer to the identification of a molecular or pathological state, disease or condition, such as the identification of an atherosclerosis-related disorder or to refer to the identification of a patient who has developed or is at risk of developing an atherosclerosis-related disorder.

The term "prognosing" or "prognosis" or "prognostic" is used herein to refer to the prediction of the likelihood of developing an atherosclerosis-related disorder.

According to the invention, the term "biomarker" means a distinctive biological or biologically-derived indicator of a process, event, or condition. The term biomarker as used herein refers to a s-RNY that is differentially expressed in an individual who has developed or is at risk of developing an atherosclerosis-related disorder compared to a control individual or population.

The term "Small Y RNA" or "s-RNY" refer to a small RNA of about 24-34 nucleotides which is derived from the processing of a Y RNA (also called RNY).

RNYs are highly conserved in eukaryotes. Human genome contains four genes encoding RNYs respectively called hY1 RNA (hRNY1) of sequence SEQ ID NO: 1 (gi|161087011|ref|NR_004391.1|), hY3 RNA (hRNY3) of sequence SEQ ID NO: 2 (gi|161087012|ref|NR_004392.1|), hY4 RNA (hRNY4) of sequence SEQ ID NO: 3 (gi|161087013|ref|NR_004393.1|) and hY5 RNA (hRNY5) RNA of sequence SEQ ID NO: 4 (gi|197209873|ref|NR_001571.2|) (hY2 is a degradation product of hY1). In *Mus musculus* genome, genes encoding RNYs are called *Mus musculus* Y1 RNA (mRNY1) of sequence SEQ ID NO: 5 (gi|161333869|ref|NR_004419.1|); *Mus musculus* Y3 RNA (mRNY3) of sequence SEQ ID NO: 6.

Human s-RNYs include s-RNY1-5p (SEQ ID NO: 7) and s-RNY1-3p (SEQ ID NO: 8) both derived from hRNY1 by processing on its 5' or 3' side, respectively; s-RNY3-5p (SEQ ID NO: 9) and s-RNY3-3p (SEQ ID NO: 10) both derived from hRNY3 by processing on its 5' or 3' side, respectively; s-RNY4-5p (SEQ ID NO: 11) and s-RNY4-3p (SEQ ID NO: 12) both derived from hRNY4 by processing on its 5' or 3' side, respectively; and s-RNY5-3p (SEQ ID NO: 13) which derives from hRNY5 by processing on its 3' side.

The small RNYs s-RNY3-5p and s-RNY4-5p have been newly identified by the inventors. Hence, the invention also concerns an isolated nucleic acid consisting of a sequence SEQ ID NO: 9 (s-RNY3-5p) or SEQ ID NO: 11 (s-RNY4-5p).

*Mus musculus* s-RNYs include *Mus musculus* s-RNY1-5p (SEQ ID NO: 14) and *Mus musculus* s-RNY1-3p (SEQ ID NO: 15) both derived from mRNY1 by processing on its 5' or 3' side, respectively, and *Mus musculus* s-RNY3-5p (SEQ ID NO: 16) and *Mus musculus* s-RNY3-3p (SEQ ID NO: 17) both derived from mRNY3 by processing on its 5' or 3' side, respectively.

In one embodiment, said at least one biomarker is selected from the group consisting of s-RNY1-5p (SEQ ID NO: 7), s-RNY1-3p (SEQ ID NO: 8), s-RNY3-5p (SEQ ID NO: 9), s-RNY3-3p (SEQ ID NO: 10), s-RNY4-5p (SEQ ID NO: 11), s-RNY4-3p (SEQ ID NO: 12), and s-RNY5-3p (SEQ ID NO: 13) or variants thereof.

As used herein, the term "variant" of a s-RNY denotes nucleic acid sequences that have at least about 80% nucleic acid sequence identity with a nucleic acid sequence disclosed herein. Preferably, a variant nucleic acid sequence will have at least about 80%, 81%, 82%, 83%, 84%, 85%, 86%, 87%, 88%, 89%, 90%, 91%, 92%, 93%, 94%, 95%, 96%, 97%, 98%, 99% nucleic acid sequence identity over the full-length of a nucleic acid sequence as disclosed herein. Nucleic acid sequence identity can be calculated by methods well-known to one skilled in the art. The percentage of identity may be calculated by performing a pairwise global alignment based on the Needleman-Wunsch alignment algorithm to find the optimum alignment (including gaps) of two sequences along their entire length, for instance using Needle, and using the DNAFULL matrix with a gap opening penalty of 10 and a gap extension penalty of 0.5. To that end, RNA sequences would be written in DNA bases.

In the frame of the invention, the level of expression of two, three or more biomarkers according to the invention may be determined.

In one embodiment, the level of expression of at least one biomarker is compared to a reference value.

According to the invention, a level of expression of at least one biomarker of the invention upper than the reference value is indicative that the individual has developed or is at risk of developing an atherosclerosis-related disorder.

As used herein, the term "determining" includes qualitative and/or quantitative detection (i.e. detecting and/or measuring the level of expression) with or without reference to a control or a predetermined value. As used herein, "detecting" means determining if a s-RNY is present or not in a biological sample and "measuring" means determining the amount of a s-RNY in a biological sample. Typically the level of expression a s-RNY may be determined for example by RT-PCR performed on a biological sample and more particularly a stem-loop RT-PCR method as described in Chen et al., (2005) Nucleic Acids Res. 2005 Nov. 27; 33(20):e179.

For instance, according to the method of the invention, determination of a level of expression of at least s-RNY1-5p (SEQ ID NO: 7), s-RNY1-3p (SEQ ID NO: 8), s-RNY3-5p (SEQ ID NO: 9) or s-RNY4-5p (SEQ ID NO: 11) upper than their respective reference values is indicative that the individual has developed or is at risk of developing an atherosclerosis-related disorder.

The term "the level of expression of a biomarker is upper than the reference value" as used herein, means that there is a statistically significant increase between the level of expression of said biomarker as determined in the biological sample and the reference value. In one embodiment, the level of biomarker can be compared to the reference value using the ratio of the level of said biomarker as compared with the reference value or using p-value.

As used herein, the term "reference value" refers to the amount of a s-RNY in biological samples obtained from the general population or from a selected population of individuals. The predetermined reference value can be a threshold value or a range. For example, the selected population may be comprised of apparently healthy subjects, such as individuals who have not previously had any sign or symptoms indicating the presence of an atherosclerosis-related disorder.

The reference value can be any number of statistical measures to distinguish between a level indicative that an individual has developed or is at risk of developing an atherosclerosis-related disorder and a level indicative that an individual has not developed or is not at risk of developing an atherosclerosis-related disorder, including Mean and Median expression levels, and/or cut-off or threshold s-RNY expression or fold change values as determined in an individual or a group of individuals.

Level of expression of small Y RNAs may be measured by using similar techniques as can be used to quantify gene transcript in particular, direct hybridization based assays and amplification-based assays, with some experimental adaptation, well known in the art, due to the short sequences of the small Y RNAs. For example, the reverse transcription of small Y RNA to cDNA is realized using hairloop primers such as developed by the Applied Biosystems company (Perkin Elmer).

For instance, nucleic acids having at least 10 nucleotides and exhibiting sequence complementarity or homology to the s-RNY of interest herein find utility as amplification primers. It is understood that such nucleic acids need not be identical, but are typically at least about 80% identical to the homologous region of comparable size, more preferably 85% identical and even more preferably 90-95% identical.

In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Primers typically are shorter single-stranded nucleic acids, of between 10 to 25 nucleotides in length, designed to perfectly or almost perfectly match a nucleic acid of interest, to be amplified. The primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

In a particular embodiment, the methods of the invention comprise the steps of providing total RNAs extracted from a biological sample such a blood sample and subjecting the RNAs to amplification with specific primers, more particularly by means of a quantitative or semi-quantitative RT-PCR as described below.

According to an embodiment, said at least one biomarker is selected from the group consisting of s-RNY1-5p (SEQ ID NO: 7), s-RNY1-3p (SEQ ID NO: 8), s-RNY3-5p (SEQ ID NO: 9), and s-RNY4-5p (SEQ ID NO: 11).

Indeed, s-RNY1-3p, s-RNY1-5p, s-RNY3-5p, and s-RNY4-5p have been identified as being induced by athero-relevant stimuli in bone marrow derived macrophages (BMDM) or human primary macrophages. Furthermore, s-RNY1-3p has been found to have a single binding site in Krüppel-like factor 2 (KLF2) mRNA and s-RNY1-3p downregulates KLF2 gene at the post-transcriptional level in lipid-laden macrophages. KLF2 has anti-apoptotic and an anti-inflammatory role in macrophages and is known as a critical gene in regulating the pathogenesis of atherosclerosis. Additionally, s-RNY1-5p and s-RNY4-5p were detected in human serum and found unregulated in serum CAD patients compared to control individuals. The inventors further found that s-RNY1-5p and s-RNY4-5p were positively correlated with pro-atherogenic lipids and correlated negatively with HDL markers. HDL markers are associated with decreased risk of atherosclerosis-related disorder.

In a preferred embodiment, the method of diagnosis or prognosis of an atherosclerosis-related disorder comprises the step of determining the level of expression of a nucleic acid of sequence s-RNY1-5p (SEQ ID NO: 7) and/or s-RNY4-5p (SEQ ID NO: 11). Preferably, the biological sample is a fluid sample, in particular whole blood, plasma or serum.

According to another embodiment, the method of diagnosis or prognosis of an atherosclerosis-related disorder comprises the step of determining the level of expression of at least one biomarker selected from the group consisting of s-RNY1-5p (SEQ ID NO: 7), s-RNY1-3p (SEQ ID NO: 8), s-RNY3-5p (SEQ ID NO: 9), and s-RNY4-5p (SEQ ID NO: 11).

The term "biological sample" refers to a biological sample obtained for the purpose of in vitro evaluation. Biological samples that may be used for performing the methods according to the invention encompass any biological sample derived from a patient containing RNA and more particularly s-RNYs, including any fluids, tissues, cell samples, organs, biopsies, etc. Typical samples to be used in the methods according to the invention are blood samples (e.g. whole blood sample), plasma or serum. In a preferred embodiment, said blood sample is a whole blood sample obtained from a patient to be tested.

The term "patient" or "individual" may be, for example a human or non-human mammal (such as a rodent (mouse, rat), a feline, a canine or a primate) affected by or likely to be affected by an atherosclerosis-related disorder. Preferably, the patient or the individual is a human. The patient may present risk factors for development of atherosclerosis-related disorder, such as obesity, diabetes, and hypertension. Preferably, the method of the invention further comprises the step of determining the level of expression of at least one pro-atherogenic lipid, preferably triglycerides, lipoprotein containing ApoB or ApoE and/or of HDL markers, preferably HDL-C and apoA-I.

Methods of Treatment

The inventors showed that s-RNY expression is induced in macrophages exposed to various types of apoptotic stimuli, including those that are relevant to atherosclerosis development (example 2). It has also been demonstrated that s-RNY expression affects the modulation of gene expression in lipid-laden macrophages by directly regulating, at the post-transcriptional level, a critical subset of mRNAs for the pathogenesis of atherosclerosis development (example 4). Additionally, s-RNYs induced by atherogenic stimuli are an intrinsic component of the machinery regulating apoptosis in lipid-laden macrophages, through activation of p38 and NF-κB pathways to ultimately promote cell death and pro-inflammatory response in macrophages (example 5). Altogether, these results identify s-RNYs as responsible for regulating pro-inflammatory and pro-apoptotic pathways in lipid-laden macrophages.

Thus the invention also concerns an inhibitor of a small Y RNA (s-RNY) for use as a medicament. The invention further concerns an inhibitor of a s-RNY for use in treating an atherosclerosis-related disorder.

The inhibitor of a s-RNY may be directed against any s-RNY as defined above, i.e. any human s-RNY or variant thereof According to an embodiment, said inhibitor of s-RNY is an inhibitor of a s-RNY selected from the group consisting of s-RNY1-5p (SEQ ID NO: 7), s-RNY1-3p (SEQ ID NO: 8), s-RNY3-5p (SEQ ID NO: 9) or s-RNY4-5p (SEQ ID NO: 11).

As used herein, the term "s-RNY inhibitor" refers to a compound that inhibits or reduces s-RNY biological activity. The biological activity of s-RNY depends on the amount of the s-RNY nucleic acid (i.e. its expression level), as well as on the amount of RNY from which s-RNY is processed and matured, or from the s-RNY interaction with its target sequences.

Therefore, the s-RNY inhibitor may reduce or inhibit s-RNY expression (i.e. inhibit RNY processing by for instance by inhibiting the interaction of RNY with its binding partner) or reduce or inhibit s-RNY interaction ability with its target sequences.

"s-RNY expression" refers to events modifying RNY post-transcriptionally, by cleavage and maturation, to provide a functional s-RNY, notably any reaction which results in inhibition of RNY processing.

As used herein, the term "target sequence" of the s-RNY according to the invention is a sequence to which the s-RNY specifically hybridizes. A target sequence interacts with a s-RNY by Watson-Crick base pairing, and includes for instance Krüppel-like factor 2 (KLF2) mRNA as described in the Section Examples below.

As used herein, the term "binding partner" refers to a molecule (peptidyl or non-peptidyl) that interacts directly with the biomarker of the invention. Preferably said binding partner is a protein partner or a fusion protein partner or its binding domain or an antibody, antibody variants, antibody-derived molecules. Preferably said binding partner is a protein implicated in maturation of hRNY1, hRNY3, hRNY4 or hRNY5.

In particular, it has been identified by the inventors that, in macrophages incubated with atherogenic stimuli, generation of s-RNYs requires Ago2 and the single-stranded RNA binding protein hnRNP A1 which makes part of the ribonucleoprotein complex. Furthermore, RNYs, the precursors of s-RNY, themselves associate with the proteins Ro60 and La/SSB to form the Ro ribonucleoprotein complex. Accordingly, a s-RNY inhibitor may be a molecule which inhibits or reduces interaction of RNYs with Ago2, heterogeneous nuclear ribonucleoproteins (hnRNPs) complex, Ro60 or La/SSB, or a molecule which inhibits or reduces Ago2 processing of RNYs.

"Ro ribonucleoprotein (RNP) complex" or Ro ribonucleoprotein particles (RNPs) contain at least three proteins: the La protein, which is involved in the correct termination of RNA polymerase III transcription and the Ro RNP-specific proteins of 52 kDa (Ro52) and 60 kDa (Ro60). Ro RNPs may contain additional components, such as RNA components. The RNA components of Ro RNPs in human cells consist of one out of four different small RNYs. Ro60 (also known as Ro/SSA) is a protein of sequence SEQ ID NO: 20 (P10155.2 GI:52788235). La (also known as SSB or La/SSB) is a protein of sequence SEQ ID NO: 21 (La/SSB: gi|10835067|ref|NP_003133.1).

Protein argonaute-2 (Ago2) is an enzyme of sequence SEQ ID NO: 18 (Acc No gi|29171734|ref|NP_036286.2). Ago2 has an endoribonuclease activity for double-stranded RNAs and is the catalytic component of the RNA-induced silencing complex (RISC). Ago2 is involved in play a role in short-interfering-RNA-mediated gene silencing.

Heterogeneous nuclear ribonucleoproteins A1 (hnRNP A1) is a nucleo-cytoplasmic shuttling protein of sequence SEQ ID NO: 19 (Acc No gi|4504445|ref|NP_002127.1) with roles in many aspects of RNA metabolism. hnRNPs are associated with pre-mRNAs in the nucleus and appear to influence pre-mRNA processing and other aspects of mRNA metabolism and transport. hnRNP A1 is involved in the packaging of pre-mRNA into hnRNP particles, transport of poly(A) mRNA from the nucleus to the cytoplasm and may modulate splice site selection.

According to one embodiment, the s-RNY inhibitor is an inhibitor of gene expression of at least one protein selected from the group consisting of Ago2 (SEQ ID NO: 18), heterogeneous nuclear ribonucleoproteins (hnRNPs, such as hnRNP A1 of sequence SEQ ID NO: 19) complex, Ro60 (SEQ ID NO: 20) and La/SSB (SEQ ID NO: 21). Preferably, said s-RNY inhibitor prevents or reduces processing of RNYs into s-RNYs.

An "inhibitor of gene expression" refers to any natural or synthetic compound that has a biological effect to inhibit the expression of a gene.

Therefore, an "inhibitor of Ago2 gene expression" denotes a natural or synthetic compound that has a biological effect to inhibit the expression of Ago2 gene expression.

Therefore, an "inhibitor of hnRNP A1 gene expression" denotes a natural or synthetic compound that has a biological effect to inhibit the expression of hnRNP A1 gene expression.

Therefore, an "inhibitor of Ro60 gene expression" denotes a natural or synthetic compound that has a biological effect to inhibit the expression of Ago2 gene expression.

Therefore, an "inhibitor of La/SSB gene expression" denotes a natural or synthetic compound that has a biological effect to inhibit the expression of hnRNP A1 gene expression.

In one embodiment of the invention, said inhibitor of gene expression is a siRNA.

Small inhibitory RNAs (siRNAs) can function as inhibitors of gene expression for use in the invention. Gene expression can be reduced with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999);

Elbashir, S. M. et al. (2001); Hannon, G J. (2002); McManus, M T. et al. (2002); Brummelkamp, T R. et al. (2002); U.S. Pat. Nos. 6,573,099 and 6,506,559; International Patent Nos. WO 01/36646, WO 99/32619, and WO 01/68836).

In one particular embodiment, the sequence of the siRNA targeting Ago2 is represented by SEQ ID NO: 22.

In one particular embodiment, the sequence of the siRNA targeting hnRNP is represented by SEQ ID NO: 23.

In one particular embodiment, the sequence of the siRNA targeting Ro60 is represented by SEQ ID NO: 24.

In one particular embodiment, the sequence of the siRNA targeting La/SSB is represented by SEQ ID NO: 25.

According to another embodiment, the s-RNY inhibitor specifically interacts with at least one nucleic acid selected from the group consisting of hRNY1 (SEQ ID NO: 1), hRNY3 (SEQ ID NO: 2), hRNY4 (SEQ ID NO: 3) and hRNY5 (SEQ ID NO: 4), preferably consisting of SEQ ID NO: 1 (hRNY1) and SEQ ID NO: 2 (hRNY3).

Typically, said s-RNY inhibitor may be an inhibitor of the interaction between Ago2 protein or heterogeneous nuclear ribonucleoproteins (hnRNPs) complex and at least one RNY, in particular a RNY selected from the group consisting of SEQ ID NO: 1 (hRNY1) and SEQ ID NO: 2 (hRNY3).

As used herein, the terms "inhibitor of the interaction" means preventing or reducing the direct or indirect association of one or more molecules, nucleic acids, peptides, proteins. As used herein, the term "inhibitor of the interaction between Ago2 or the heterogeneous nuclear ribonucleoproteins (hnRNPs) complex and at least one RNY" is a molecule which can prevent the interaction between Ago2 or hnRNPs with at least one RNY by competition or by fixing to one of the molecules.

The s-RNYs provide a new identified tool for controlling the expression of target genes. More particularly, s-RNYs enable inhibition of the expression of said target genes by exploiting an Ago2-associated machinery to cause degradation of mRNAs that contain complementary sequences to s-RNYs. One possible way of interfering with the s-RNYs activity, is to use oligonucleotides (ODNs) comprising complementary nucleic acid sequences of these s-RNYs as competitors of the endogenous sequence within the mRNAs of target genes, for binding to s-RNYS. Like the natural elements, the decoys are able to bind s-RNYs. Therefore, when these elements are in surplus they will decoy s-RNYs away from natural transcriptional elements. When regulatory factors, s-RNYs in particular, are prevented from binding their target sequences, their regulatory effects on gene expression are generally impeded. The decoy strategy aims at providing an intracellular surplus of ODNs binding to s-RNYs, thus sequestering them from their natural site(s). In this way, mRNAs degradation induced by s-RNYs is prevented.

Inhibitors of said s-RNY for use in the invention may be based on antisense oligonucleotide (ODNs) constructs. Antisense oligonucleotides, including anti-sense RNA molecules and anti-sense DNA molecules, would act to directly block the activity of s-RNYs by binding thereto and thus preventing binding leading to mRNA degradation, For example, antisense oligonucleotides of at least about 15 bases and complementary to unique regions of the s-RNY transcript sequence can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). It should be further noted that antisense oligonucleotides may be modified with phosphorothioate to prevent their in vivo hydrolysis by nucleases. Such modifications are well known in the art. Antisense oligonucleotides useful as inhibitors of s-RNY inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters.

Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Accordingly in one preferred embodiment, the inhibitor of said s-RNY is a nucleic acid which specifically hybridizes to at least one nucleic acid sequence selected from the group consisting of s-RNY1-5p (SEQ ID NO: 7), s-RNY1-3p (SEQ ID NO: 8), s-RNY3-5p (SEQ ID NO: 9), s-RNY3-3p (SEQ ID NO: 10), s-RNY4-5p (SEQ ID NO: 11), s-RNY4-3p (SEQ ID NO: 12), and s-RNY5-3p (SEQ ID NO: 13) or variants thereof.

Typically, said inhibitor is a nucleic acid of sequence selected from the group consisting of SEQ ID NO: 22 (siRNA targeting Ago2), SEQ ID NO: 23 (siRNA targeting hnRNP), SEQ ID NO: 24 (siRNA targeting Ro60), SEQ ID NO: 26 (2'-OMe-RNA antisense to human or mouse s-RNY1-5p), and SEQ ID NO: 54 (2'-OMe-RNA antisense to human s-RNY4-5p: 5'-AGUUCUGAUAACCCACUAC-CAUCGGACCAGCC-3').

The invention further concerns a method of treating an atherosclerosis-related disorder, comprising administering to a patient in need thereof a therapeutically effective amount of an inhibitor of a s-RNY.

According to an embodiment, said s-RNY is selected from the group consisting s-RNY1-5p (SEQ ID NO: 7), s-RNY1-3p (SEQ ID NO: 8), s-RNY3-5p (SEQ ID NO: 9) and s-RNY4-5p (SEQ ID NO: 11).

The inhibitor of a s-RNY is advantageously formulated in a pharmaceutical composition, together with a pharmaceutically acceptable carrier.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, 'Treatment' includes both therapeutic treatment and prophylactic or preventive treatment, wherein the object is to prevent or slow down the targeted pathologic condition or disorder. Those in need of treatment include those already with the disorder as well as those prone to have the disorder or those in whom the disorder is to be prevented. The term "treating" includes reducing, alleviating or inhibiting or eliminating the symptoms or progress of a disorder.

Treatment in accordance with the invention includes a method of treating an atherosclerosis-related disorder, which comprises administering to a patient in need of treatment, an inhibitor of s-RNY or pharmaceutical composition containing such inhibitor. Preferably, the treatment further comprises administering to said patient an anti-atherosclerosis drug, such as bile acid sequestrant, niacin (nicotinic acid), statins (HMG-CoA reductase inhibitors), fibrates or probucol, or combinations thereof.

Preferably, an effective amount, preferably a therapeutically effective amount of the inhibitor of s-RNY of the invention is administered. An "effective amount" refers to an amount effective, at dosages and for periods of time necessary, to achieve the desired therapeutic or prophylactic result. The effective amount may vary according to the drug with which the inhibitor of s-RNY is co-administered.

A "therapeutically effective amount" of an inhibitor of s-RNY of the invention may vary according to factors such as the disease state, age, sex, and weight of the individual, and the ability of the inhibitor of s-RNY, to elicit a desired therapeutic result. A therapeutically effective amount encompasses an amount in which any toxic or detrimental effects of the inhibitor of s-RNY are outweighed by the therapeutically beneficial effects. A therapeutically effective amount also encompasses an amount sufficient to confer benefit, e.g., clinical benefit.

According to another aspect of the invention, it is provided a method of treating an atherosclerosis-related disorder, which comprises the steps of:
a) diagnosing or prognosing an atherosclerosis-related disorder in an individual by determining the level of expression of at least one biomarker consisting of a small Y RNA (s-RNY) in a biological sample of said individual, as described above, and
b) administering a therapeutically effective amount of anti-atherosclerosis drug to said individual diagnosed or prognosed with an atherosclerosis-related disorder.

According to said aspect, the invention also relates to an anti-atherosclerosis drug for use in treating an atherosclerosis-related disorder in an individual, wherein the individual has been diagnosed or prognosed with an atherosclerosis-related disorder by determining the level of expression of at least one biomarker consisting of a small Y RNA (s-RNY) in a biological sample of said individual. In particular, said use can comprise diagnosing or prognosing the individual with an atherosclerosis-related disorder by measuring the level of expression of at least one biomarker consisting of a small Y RNA (s-RNY) in a biological sample of said individual.

According to said aspect of the invention, the anti-atherosclerosis drug may be, without limitation, a bile acid sequestrant, niacin (nicotinic acid), statins (HMG-CoA reductase inhibitors), fibrates or probucol, a s-RNY inhibitor as described above, or combinations thereof.

A Method for Screening for a Compound Suitable for the Treatment and/or Prevention of an Atherosclerosis-Related Disorder The invention further concerns a method of screening for a compound suitable for the treatment of an atherosclerosis-related disorder which comprises the steps of:
a) contacting a candidate compound with a s-RNY or a RNY,
b) identifying as a compound suitable for the treatment of an atherosclerosis-related disorder which inhibits the maturation of said RNY into s-RNY or which inhibits the activity of said s-RNY.

Said s-RNY may be s-RNY1-5p (SEQ ID NO: 7), s-RNY1-3p (SEQ ID NO: 8), s-RNY3-5p (SEQ ID NO: 9), s-RNY3-3p (SEQ ID NO: 10), s-RNY4-5p (SEQ ID NO: 11), s-RNY4-3p (SEQ ID NO: 10), s-RNY5-3p (SEQ ID NO: 13) or variants thereof. Preferably, said s-RNY is selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p) or a variant thereof.

Said RNY may be RNY1, RNY3, RNY4 or RNY5, preferably selected from the group consisting of SEQ ID NO: 1 (hRNY1), SEQ ID NO: 2 (hRNY3) and SEQ ID NO: 3 (hRNY4), still preferably SEQ ID NO: 1 (hRNY1), SEQ ID NO: 2 (hRNY3).

According to the invention, a compound suitable for the treatment of an atherosclerosis-related disorder may inhibit the interaction of a RNY with a polypeptide selected from the group consisting of SEQ ID NO: 18 (Ago2), SEQ ID NO:20 (Ro60), SEQ ID NO: 19 (hnRNP A1) and SEQ ID NO:21 (La/SSB).

Typically, determination of the ability of a candidate compound to inhibit the activity of a s-RNY may comprise the step of determining the level of expression of a polypeptide of sequence selected from the group consisting of SEQ ID NO: 29 (c-Fos; gi|4885241|ref|NP_005243.1), SEQ ID NO: 30 (Krüppel-like factor 2 (KLF2) gi|7706469|ref|NP_057354.1), SEQ ID NO: 31 (Zfyve28 gi|187953521|gb|AAI37311.1), SEQ ID NO: 32 (Rhomboid family-1 (Rhbdf1) gi|190341097|ref|NP_071895.3), SEQ ID NO: 33 (Fgfr1, gi|105990522|ref|NP_075598.2), SEQ ID NO: 34 (Lysyl oxidase (Lox) gi|20149540|ref|NP_002308.2) and SEQ ID NO: 35 (Nr4a1 (also known as Nur77) gi|27894344|ref|NP_775180.1). These polypeptides are known to be important in regulating the pathogenesis of atherosclerosis, and their mRNAs have been identified as potential s-RNYs direct target-mRNAs by the inventors.

As used herein the term "protein" or "polypeptide" refers to any chain of amino acids linked by peptide bonds, regardless of length or post-translational modification.

The level of expression of a protein or a polypeptide may be determined by any method familiar to one skilled in the art. Such methods typically include methods based on the determining the corresponding mRNA expression and methods based on the determining the level of expression of a protein.

The level of expression of a protein or a polypeptide may be assessed by determining the corresponding mRNA expression (transcription products). This measurement may be performed by various methods which are well known to the person skilled in the art, including quantitative methods involving reverse transcriptase PCR (RT-PCR), such as real-time quantitative RT-PCR (qRT-PCR), and methods involving the use of DNA arrays (macroarrays or microarrays) and in situ hybridization.

The level of expression of a protein or a polypeptide may be assessed by using immunologic methods. Suitable immunologic methods include enzyme linked immunoassays (ELISA), sandwich, direct, indirect, or competitive ELISA assays, enzyme linked immunospot assays (ELIspot), radio immunoassays (RIA), flow-cytometry assays (FACS), immunohistochemistry, Western Blot, fluorescence resonance energy transfer (FRET) assays, protein chip assays using for example antibodies, antibody fragments, receptor ligands or other agents binding the proteins coded by the sequence. The level of expression of such proteins is quantified using technologies well known by the art.

Primers and Kits Containing Thereof for Use in Diagnosing or Prognosing Atherosclerosis-Related Disorders The invention concerns a pair of primers suitable for amplifying a s-RNY for use in diagnosing or prognosing an atherosclerosis-related disorder.

The invention also concerns a probe specifically hybridizing to a s-RNY for use for diagnosing or prognosing an atherosclerosis-related disorder. Accordingly a nucleic acid specifically hybridizing to a nucleic acid sequence consisting of SEQ ID NO: 9 (s-RNY3-5p) or SEQ ID NO: 11 (s-RNY4-5p) is provided for use as a probe for diagnosing or prognosing atherosclerosis-related disorder.

Said s-RNY may be s-RNY1-5p (SEQ ID NO: 7), s-RNY1-3p (SEQ ID NO: 8), s-RNY3-5p (SEQ ID NO: 9), s-RNY3-3p (SEQ ID NO: 10), s-RNY4-5p (SEQ ID NO: 11), s-RNY4-3p (SEQ ID NO: 12), s-RNY5-3p (SEQ ID NO: 13) or variants thereof. Preferably, said s-RNY is selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p) or variants thereof.

The term "probe" refers to an isolated nucleic acid capable of hybridizing to a target nucleic acid. A detectable label or reporter molecule can be attached to a probe. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. ((1989) *Molecular Cloning; A Laboratory Manual*, Cold Spring Harbor). Probes are preferably at least 12, 15, 20, 25, or 30 nucleotide long. Probes may be less than 60, 50, 40 or preferably 35 nucleotide long.

Probes can be used for diagnosing or prognosing atherosclerosis-related disorder by identifying that at least one s-RNY as described above, in particular a s-RNY selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p) or variants thereof is over-expressed in a biological sample compared with a control sample or a reference value. Contacting a total RNA sample (transcriptome) of a biological sample, with the probe, under conditions which allow hybridization of the probe with its corresponding fragment in the nucleic acid, results in the formation of a nucleic acid/probe hybrid. The formation of this hybrid can be detected (e.g., via labeling of the nucleic acid or probe), whereby the formation of this hybrid indicates the expression of the corresponding sequence. Such identification methods based on hybridization with a specific probe (either on a solid phase carrier or in solution) have been described in the art. The specific probe is preferably a sequence which, under optimized conditions, hybridizes specifically to at least one s-RNY selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p.

Preferably, the probe comprises a sequence which is at least 80%, preferably between 80 and 85%, more preferably between 85 and 90%, especially preferably between 90 and 95%, most preferably between 95% and 100% identical (or complementary) to the nucleotide sequence of a specific region. Preferably, the probe will comprise a sequence of about 15 to about 40, or 20 to about 40 and notably, 15, 20, 25, 30, 35, 38, or all contiguous nucleotides identical (or complementary) to a s-RNY, in particular to a s-RNY selected from the group consisting of SEQ ID NO: 7 (s-RNY1-5p), SEQ ID NO: 9 (s-RNY3-5p), SEQ ID NO: 8 (s-RNY1-3p), SEQ ID NO: 11 (s-RNY4-5p), SEQ ID NO: 10 (s-RNY3-3p), SEQ ID NO: 12 (s-RNY4-3p) and SEQ ID NO: 13 (s-RNY5-3p) or variants thereof, preferably, a s-RNY selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p) or variants thereof.

A probe according to the invention may comprise, consist or consist essentially of a sequence selected from the group consisting of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 47, SEQ ID NO: 48, SEQ ID NO: 49, SEQ ID NO: 50, SEQ ID NO: 51 and SEQ ID NO: 52. Preferably, said probe according to the invention may comprise, consist or consist essentially of a sequence selected from the group consisting of SEQ ID NO: 36, SEQ ID NO: 37, SEQ ID NO: 38, SEQ ID NO: 40, SEQ ID NO: 41, SEQ ID NO: 43, SEQ ID NO: 44, SEQ ID NO: 47, SEQ ID NO: 48, and SEQ ID NO: 52.

The term "primer" is meant for short nucleic acid molecules, such as a DNA oligonucleotide, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule. Primer pairs can be used for amplification of a nucleic acid sequence, for example, by PCR, real-time PCR, or other nucleic-acid amplification methods known in the art. Methods for preparing and using primers are described for example, in Sambrook et al. ((1989) *Molecular Cloning: A Laboratory Manual*, Cold Spring Harbor, New York). Said primer may be a sense primer and/or an antisense primer, said sense primer comprising or consisting of 15 to 40 consecutive nucleotides of a nucleotide sequence that is identical to or substantially identical (i.e. at least 75%, 80%, 90%, 95% or 98% identical) to the nucleotide sequence of a s-RNY, in particular to a s-RNY selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p), or a variant thereof, and said antisense primer comprising or consisting of 15 to 40 consecutive nucleotides of a nucleotide sequence that is complementary to a nucleotide sequence that is identical to or substantially identical (i.e. at least 75%, 80%, 90%, 95% or 98% identical) to the nucleotide sequence of a s-RNY, in particular to a sequence selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p), or a variant thereof. Preferably, primers may be less than 100, 50, 40, 25 or preferably 20 nucleotides long.

A primer according to the invention may comprise, consist or consist essentially of a sequence selected from the group consisting of SEQ ID NO: 36, SEQ ID NO: 37, SEQ ID NO: 38, SEQ ID NO: 39 SEQ ID NO: 40, SEQ ID NO: 41, SEQ ID NO: 42, SEQ ID NO: 43, SEQ ID NO: 44, SEQ ID NO: 47, SEQ ID NO: 48, SEQ ID NO: 49, SEQ ID NO: 50, SEQ ID NO: 51 and SEQ ID NO: 52. Preferably, said primer according to the invention may comprise, consist or consist essentially of a sequence selected from the group consisting of SEQ ID NO: 36, SEQ ID NO: 38, SEQ ID NO: 39, SEQ ID NO: 40, SEQ ID NO: 41, SEQ ID NO: 43, SEQ ID NO: 44, SEQ ID NO: 47, SEQ ID NO: 48, and SEQ ID NO: 52.

The invention also relates to a pair of primers suitable for amplifying a nucleic acid sequence consisting of SEQ ID NO: 9 (s-RNY3-5p) or SEQ ID NO: 11 (s-RNY4-5p), both s-RNY being newly identified by the inventors.

The invention also relates to a probe specifically hybridizing to a nucleic acid sequence consisting of SEQ ID NO: 9 (s-RNY3-5p) or SEQ ID NO: 11 (s-RNY4-5p).

Also provided is a probe or primers specifically hybridizing to a s-RNY as described above, in particular to a s-RNY selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p) or variants thereof, for use for diagnosing or prognosing of an atherosclerosis-related disorder.

The invention also concerns a kit comprising means for determining the level of expression of at least one s-RNY, in particular of a s-RNY selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p) or a variant thereof, such as the pair of primers and/or probes according to the invention.

The kits according to the invention may be used for use in the diagnosis or prognosis of an atherosclerosis-related disorder by determining the level of expression of at least one biomarker of the invention. The kit of the invention may thus comprise a combination of reagents allowing to determine the level of expression of at least one s-RNY, in particular of a s-RNY of sequence SEQ ID NO: 7 (s-RNY1-5p), SEQ ID NO: 8 (s-RNY5-5p), SEQ ID NO:9 (s-RNY1-3p) or SEQ ID NO: 11 (s-RNY4-5p) or a variant thereof and optionally the instructions of the manufacturer for use in the diagnosis or prognosis of an atherosclerosis-related disorder. Accordingly, it comprises, for each of the biomarkers to be tested, at least one probe or a pair of primers that selectively hybridize with said biomarkers.

The kit according to the invention may further comprise at least one reference value.

The invention will be further described in view of the following figures and examples.

EXAMPLES

Example 1: Material and Methods

Animals and Diets

Figure 1:
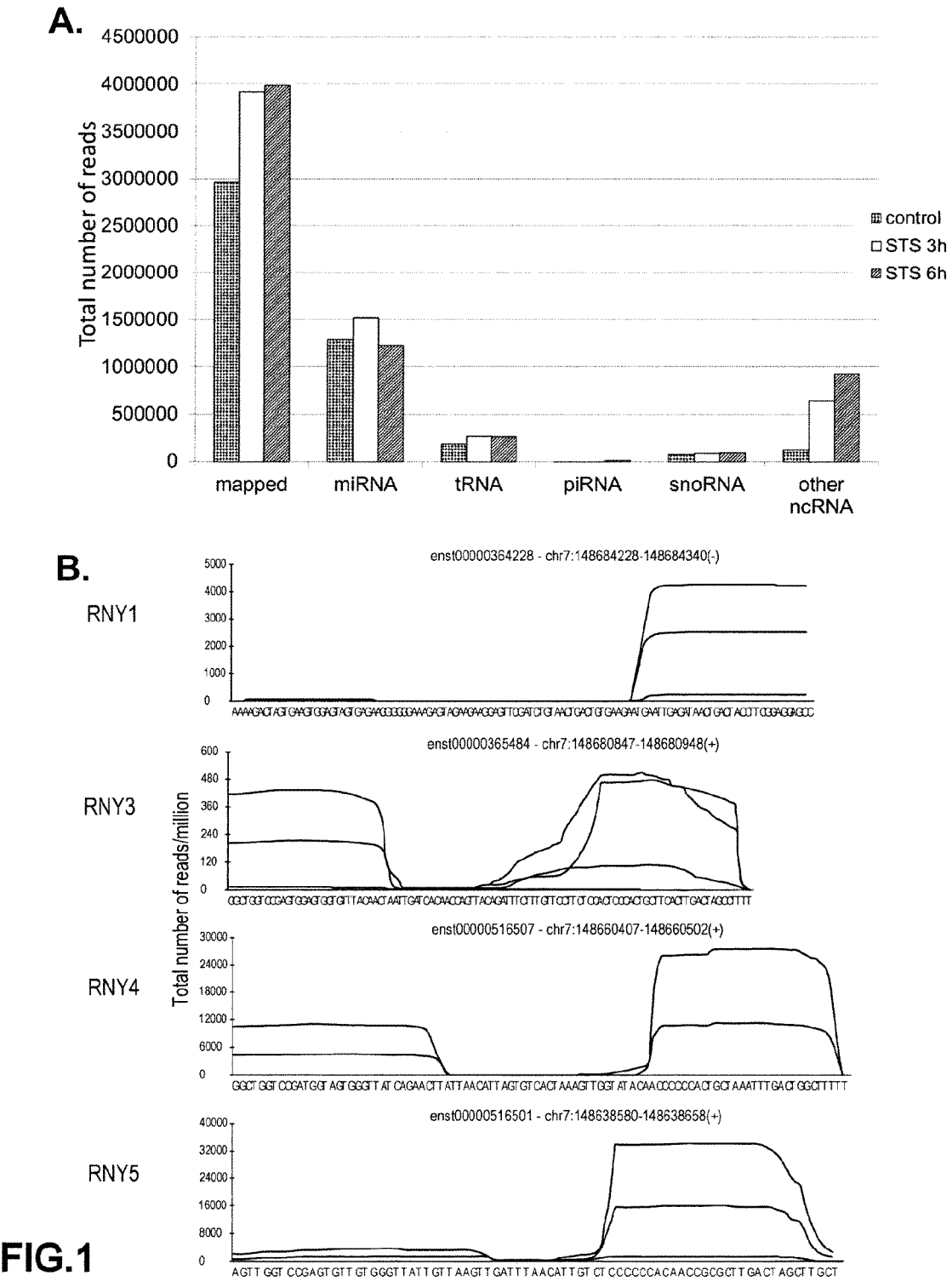
FIG. 1: (A) Bioinformatic analysis of the high-throughput small RNAs sequencing showing the distribution of different classes of small RNAs identified and the upregulation of small RNAs derived from RNYs. (B) (s-RNYs) in human primary macrophages stimulated with 1 µM of staurosporine (STS) at the indicated time points.

Animals were kept in a pathogen-free barrier facility and maintained in accordance with Institutional Animal Care and Use Protocol of University of Nice Sophia Antipolis in accordance with appropriate national regulations concerning animal welfare. The following mice were purchased from Charles River Laboratories (L'Arbresle, France): C57BL/6J, ApoE−/− (B6.129P2-APOE/J), and Ldlr−/− (B6.129S7-Ldlrtm1Her/J). High Cholesterol Diet (HCD) formula # TD02028 and TD96335 (Harlan Teklad) for ApoE−/− or Ldlr−/−, respectively, were purchased from ssniff Spezialdiaten GmbH (Soest, Germany). ApoE−/− and Ldlr−/− male mice at 8 weeks of age were fed with either HCD or regular diet (chow diet) for 12 or 20 weeks, respectively. Aortic arches, heart, and blood plasma were dissected.

Study Population and Data Collection

Subjects were randomly selected from a large case-control study on coronary artery disease (CAD) referenced as GENES study (Genetique et Environnement en Europe de Sud) as previously described (Bouisset et al., 2012). Briefly, CAD male patients living in the Toulouse area (Southwestern France) and aged between 45 and 74 years, were prospectively recruited from 2001 to 2004, admitted in the Department of Cardiology of the Toulouse University Hospital, and referred for evaluation and management of stable CAD. Stable CAD was defined by a history of acute coronary syndrome and of coronary revascularization, documented myocardial ischemia, stable angina, or the presence on the coronary angiogram of a coronary stenosis of >50%. During the same period, healthy male controls, aged 45 to 74, were selected from the general population using the electoral rolls. Stratification by 10-age group was used to approximately match the age distribution of the controls with that of cases. All individuals underwent medical examination in the Department of Cardiology in the Toulouse University Hospital and completed standardized questionnaires covering age, medical history, socioeconomic and lifestyle variables such as educational level, smoking status and physical activity. Physical activity was categorized into five levels from 1 to 4: no physical activity (1), light physical activity for 20 min once a week (2), moderate physical activity for 20 min twice a week (3), intense physical activity for 20 min 3 times a week or more (4). They also underwent a standardized medical examination with anthropometric and clinical measurements and provided fasting blood samples. Blood samples were analyzed for serum total cholesterol, high-density lipoprotein-cholesterol (HDL-C), triglycerides (TG), glucose, γ-glutamyltransferase (γ-GT) and sensitive C-reactive protein (CRP) with enzymatic reagents on an automated analyser (Hitachi 912, Roche Diagnostics, Meylan, France). LDL-cholesterol (LDL-C) was calculated using the Friedewald formula, with VLDL-cholesterol (VLDL-C) (g/L)=TG (g/L)/5 as long as TG concentration was below 4 g/L (Genoux et al., 2011). Lipoproteins containing ApoB and ApoE (LpB:E) were assayed by a specific immuno-electrodiffusion assay (Sebia, France). In the present work, 45 CAD patients and 45 age-matched control individuals were randomly drawn for serum s-RNYs measurements.

In the tables 3 and 4, data are presented as percentage for qualitative variables or as mean with standard deviation for quantitative ones. Qualitative variables were compared with $\chi^2$ test (or Fisher exact test when necessary). The mean values of quantitative variables were compared to Student's t-test. Shapiro-Wilks was used to test the normality of distribution of residuals and Levene's test to check the homogeneity of variables. When the basic assumptions of Students t-test were not satisfied, the data were logarithmically transformed or subjected to a Wilcoxon Mann Whitney's test. Associations of s-RNYs with clinical characteristics and biological markers were tested using Spearman's rank correlations. Analyses were two-tailed and p<0.05 was considered to be significant. These statistical analyses were carried out using the SAS statistical software package 9.2 (SAS Institute, Cary, Ill., USA) and with STATA statistical software (release 11.2, Stata Corporation, College Station, Tex., USA). ROC test was calculated using GraphPad Prism (version 5.01, La Jolla, Calif. 92037, USA).

Ethics Statement

The study protocol was approved by the local Ethics Committee of the hospital of Toulouse (CHU Toulouse/INSERM, file 1-99-48, February 2000) and the national commission for data processing and freedoms (N° 900165). Written informed consent was obtained from all participants involved in the study. Biological collection was constituted according to the principles expressed in the Declaration of Helsinki and registered under number DC-2008-403 at the Ministry of Research and at the Regional Health Agency.

Reagents

LPS, LTA, Tg, STS, BSA, PA, stearic acid, oleic acid, and linoleic acid were purchased from Sigma (Saint-Quentin Fallavier, France). oxLDL was purchased from Clinisciences (Nanterre, France).

Primary Macrophages

Bone marrow cells were collected from femurs and tibias of ten-week-old male C57BL/6J mice by flushing with sterile medium as previously described (T. Ruggiero, M. et al (2009) *FASEB J* 23:2898-2908). To differentiate into macrophages, bone marrow cells ($10^6$) were plated in 10-cm plates in 7 ml of BMDM medium (DMEM supplemented with 20% low-endotoxin fetal bovine serum, 30% L929-cell conditioned medium, 1% I-glutamine, 1% Pen/Strep, 0.5% Na pyruvate, and 0.1% β-mercaptoethanol), and fed with 2.5 ml of fresh medium every 2 days for 7 days. Human primary macrophages were prepared from peripheral blood monocytes obtained from healthy donors (Jacquel, A., et al. (2012). *Blood* 119, 4527-4531) in agreement with the French legislation on human biomedical research. All participants provided written informed consent attesting they had received all the information they needed about the study and they agreed in accordance with appropriate national regulations.

Cell Transfection and Immunoblotting

BMDMs and NIH-3T3 cells (ATCC) were transiently transfected for 48 hr with Lipofectamine 2000 (Invitrogen) according to the manufacturer's instructions. siRNAs were transfected at the final concentration of 24 nM, while 2'-OMe-RNA antisense oligonucleotides to s-RNYs (Eurogentec) were transfected at the final concentration of 100 nM. When required, cell lysates were incubated at room temperature with RNase A (10 mg/ml, Ambion) for 30 min. Three-hundred micrograms of protein was immunoprecipitated with Protein A-Dynabeads (Invitrogen)-coupled antibodies for 16 hr at 4° C. with rotation. Immunoprecipitates were washed four times with lysis buffer and resuspended in SDS protein loading buffer. Proteins were subjected to SDS-PAGE, electroblotted onto PVDF membranes, and probed with different antibodies as indicated.

Small RNA Sequencing

Ten micrograms of total RNAs were subjected to the small RNA preparation procedure, and the libraries were sequenced on either Illumina or Solidi platforms. For the analysis, the 3' adaptor sequence was removed using FASTX, and the clipped reads were aligned to the genome database and DeepBase53 using BLAT and Novoalign.

Fluorescence In Situ Hybridization and Immunofluorescence

Fluorescence in situ hybridization coupled with immunofluorescence was carried out as previously described (Hu, Q., et al. (2012). *Nature structural & molecular biology* 19, 1168-1175). BMDMs were fixed in 10% neutral formalin and hybridized with FAM-labeled antisense LNA probe. The slides were then incubated with an human anti-GW182 antiserum to stain P-bodies (Eystathioy, T., et al. (2003). *Journal of molecular medicine* (Berlin, Germany) 81, 811-818). The probe used in this study was purchased from Exiqon (Denmark). For immunofluorescence, aortic sinus from ApoE$^{-/-}$ mice were fixed in 10% neutral formalin, penetrated with 20% sucrose in PBS, and embedded in OCT compound. Serial 10-μm sections of the aortic sinus were stained with a rat Mac3 and a mouse monoclonal hnRNP A1 antibodies. Slides were coverslipped in Vectashield Mounting Medium with Dapi (Invitrogen). The results were analyzed on a Leica DM5500B microscope with a HAMAMATSU camera ORGA-ER. LNA probe sequence is detailed in Table 1.

TABLE 1

Oligonucleotidesused for RT-PCR, cloning and Northern blot analyses.

| | Forward primer | Reverse primer |
|---|---|---|
| Mouse and human s-RNY1-5p (RT) | | 5'- GTC GTA TCC AGT GCA GGG TCC GAG GTA TTC GCA CTG GAT ACG ACA TTG AG -3' (SEQ ID NO: 36) |
| mouse s-RNY3-5p (RT) | | 5'- GTC GTA TCC AGT GCA GGG TCC GAG GTA TTC GCA CTG GAT ACG ACA CC -3' (SEQ ID NO: 37) |
| human s-RNY3-5p (RT) | | 5'- GTC GTA TCC AGT GCA GGG TCC GAG GTA TTC GCA CTG GAT ACG ACA GTT GT -3' (SEQ ID NO: 38) |
| human s-RNY4-5p (RT) | | 5'- GTC GTA TCC AGT GCA GGG TCC GAG GTA TTC GCA CTG GAT ACG ACA GTT CT -3' (SEQ ID NO: 39) |
| s-RNYs universal primer (qPCR) | | 5'- GTGCAGGGTCCGAGGT -3' (SEQ ID NO: 40) |
| Mouse/human s-RNY1-5p (qPCR) | 5'- TGGTCCGAAGGTAGTGAGT -3' (SEQ ID NO: 41) | |
| Mouse s-RNY3-5p (qPCR) | 5'- TTGGTCCGAGAGTAGTGGT -3' (SEQ ID NO: 42) | |
| Human s-RNY3-5p (qPCR) | 5'- TCCGAGTGCAGTGGTGTTTA -3' (SEQ ID NO: 43) | |
| Human s-RNY4-5p (qPCR) | 5'- GGTCCGATGGTAGTGGGTTAT -3' (SEQ ID NO: 44) | |
| wt s-RNY1-3p BS from KLF2 mRNA (cloning) | 5'- AAG GCG CAT CTG CGT ACA CAC ACA GGT GAG AAG CCT AAG GCG CAT CTG CGT ACA CAC ACA GGT GAG AAG CCT -3' (SEQ ID NO: 45) | |
| mutant s-RNY1-3p BS from KLF2 mRNA | 5'- AAG GCG CAT CTG CGT ACA CAC ACA GAG TGA GGA CCT AAG GCG CAT CTG CGT ACA CAC ACA GAG TGA GGA CCT -3' (SEQ ID NO: 46) | |
| Mouse and humans s-RNY1-5p (Northern blot) | | 5'- ACTCACTACCTTCGGACCA -3' (SEQ ID NO: 47) |
| Mouse and humans s-RNY1-3p (Northern blot) | | 5'- AGTCAAGTGCAGTAGTGAG -3' (SEQ ID NO: 48) |

TABLE 1-continued

Oligonucleotides used for RT-PCR, cloning and Northern blot analyses.

| | Forward primer | Reverse primer |
|---|---|---|
| Mouse RNY1 loop (Northern blot) | | 5'- TTCAATCTGTAACTGACTG -3' (SEQ ID NO: 49) |
| Mouse s-RNY3-5p (Northern blot) | | 5'- ACCACTACTCTCGGACCAA -3' (SEQ ID NO: 50) |
| Mouse s-RNY3-3p (Northern blot) | | 5'- CTGGTCAAGTGAAGCAGTG -3' (SEQ ID NO: 51) |
| Human s-RNY4-5p (Northern blot) | | 5'- CCCACTACCATCGGACCAG -3' (SEQ ID NO: 52) |
| U6 snRNA (Northern blot) | | 5'-CGT TCC AAT TTT AGT ATA TGT GCT GCC GAA GCG AGC AC-3' (SEQ ID NO: 53) |

Microarray Analysis

For mRNA profiling analysis BMDMs were collected from 4 C57BL/6J males and transfected with siRNAs against the terminal loop of RNYs and control. 48 hr after transfection, total RNA was isolated by using RNAeasy kit (Qiagen). RNA samples were labeled with Cy3 dye using the low RNA input QuickAmp kit (Agilent) as recommended by the supplier. 400 ng of labeled cRNA probe were hybridized on 8×60K high density SurePrint G3 gene mouse GE 8×60K Agilent microarrays. Normalization of microarray data was performed with the Limma package available from Bioconductor (http://www.bioconductor.org) using the quantile methods. Means of ratios from si RNYs-treated versus control were calculated. Differentially expressed genes were selected based on at least a modulation of 1.2 fold change between BMDMs overexpressing s-RNYs and control, and a statistically significant Student t-test (p<0.05).

Apoptosis Assay

Apoptosis was assayed in BMDMs by staining with Alexa 488-conjugated annexin V and Dapi as previously described (Jacquel, A., et al., 2012. *Blood* 119(19): 4527-4531). The number of annexin V- and Dapi-positive cells was counted and expressed as a percent of the total number of cells from duplicate wells.

Luciferase Reporter Assay

NIH-3T3 cells (80% confluence in 96-well plates) were transfected with Lipofectamine 2000® according to the manufacturer's instructions. Luciferase reporter assay was performed as previously described (Repetto, E., et al. (2012). *PLoS genetics* 8, e1002823).

RNA In Vitro Processing and UV-Crosslinking $^{32}$P-labeled RNAs were synthesized and used as substrates for either in vitro processing assays or UV-crosslinking experiments as previously described (Trabucchi, M., et al (2009). *Nature* 459, 1010-1014).

RNA Immunoprecipitation

RNA immunoprecipitation was performed as previously described (Trabucchi, M., et al (2009). *Nature* 459, 1010-1014) with minor modifications. Briefly, cells lysates were immunoprecipitated with Protein A-Dynabeads (Invitrogen)-coupled antibodies at 4° C. overnight. Total RNA was prepared using Trizol (Invitrogen), and analyzed by quantitative RT-PCR. The primer sequences are detailed in Table 1.

Northern Blot

Total RNA was isolated from cells using Trizol (Invitrogen), resolved on 10% polyacrylamide-urea gels, and electroblotted onto HyBond N+ membranes. Membranes were hybridized overnight with radiolabeled DNA antisense oligonucleotides to s-RNYs in ExpressHyb solution (Clontech). After hybridization, membranes were washed three times with 2×SSC and 0.05% SDS, twice with 0.1×SSC and 0.1% SDS, exposed overnight to imaging screens, and analyzed using a Storm 860 PhosphorImager. The same blot was hybridized (upon stripping in boiling 0.1% SDS) with three distinct probes, including control U6 snRNA (Table 1).

mRNA and s-RNY Expression Analysis

RNA expression by quantitative RT-PCR was carried out by using standard procedures. Briefly, for mRNA, total RNA was isolated from cells using Trizol and cDNA was synthesized with a random hexonucleotides using Superscript III (Invitrogen). For s-RNYs detection by quantitative RT-PCR a stem-loop quantitative RT-PCR method was used according to Chen et al. (Chen, C., et al. (2005). *Nucleic acids research* 33, e179). Briefly, total RNA was isolated from cells, tissue, or immunoprecipitation using Trizol (Invitrogen) according to the manufacturer's instructions. RNA extraction from extracellular medium, blood plasma, and serum was performed as previously described (Turchinovich, A., et al (2011). *Nucleic acids research* 39, 7223-7233). Briefly, 1.2 ml of Trizol LS were added to 0.4 ml of blood plasma, serum or media. Then (i) 5 pg of synthetic miRNA-39 from *Caenorhabditis elegans* (cel-miR-39) were added as a spike-in control for purification efficiency; (ii) 1.2 µl of glycogen (10 mg/ml) were added to enhance the efficiency of RNA column binding. Purification of extracted total RNA was performed with miRNeasy columns (Qiagen) according to the manufacturer's instructions. RNA was eluted in 30 µl of RNase-free water. cDNA was synthesized using a hairpin long oligonucleotide. This method allows the detection of the s-RNYs derived from only the 5' end of the precursor by quantitative RT-PCR analysis, namely the s-RNY1-5p and s-RNY3-5p from mouse and s-RNY1-5p, s-RNY3-5p, and s-RNY4-5p from human. Quantitative RT-PCRs using Sybr Green and TaqMan (Invitrogen) for cel-miR-39 were performed on a StepONE system (Applied Biosystem). The primer sequences are detailed in Table 1.

Recombinant Proteins and Antibodies for Western Blot

Recombinant Ago2 and hnRNP A1 were purchased from Sino Biological Inc. and CliniSciences, respectively, while recombinant KSRP was a gift from Dr. R. Gherzi. Mouse monoclonal anti-hnRNP A1 (4B10), mouse monoclonal anti-c-Myc (9E10), goat anti-actin (1-19), and IκBα (H-4) antibodies were purchased from SantaCruz. Rabbit anti-La/

SSB and anti-Ro60 (TROVE2) antibodies were purchased from GmbH. Anti-Ago2 antibody was purchased from Wako Chemicals while rabbit anti-KLF2 and anti-NOS2A antibodies were from Millipore. Anti-KSRP antibody was a gift from Dr. R. Gherzi. Mouse monoclonal anti-p53 (1C12), rabbit anti-cleaved Caspase-3 (Asp175), rabbit anti-caspase 3 (8G10), rabbit anti-P-p38 (9211), rabbit anti-p38 (9212), mouse anti-P-JNK (9255), and rabbit anti-P-JNK (9252) antibodies were purchased from Cell Signaling. Human anti-GW182 was a gift from Dr. M. J. Fritzler. Rat anti-mouse Mac-3 antibody (M3/84) was from BD Pharmingen. The immunofluorescence was revealed by using fluorescent secondary antibodies: Alexa Fluor 488-conjugated anti-rat IgG (H+L) antibody (Cell Signaling) for anti-mouse Mac3, Alexa Fluor 594-conjugated anti-mouse IgG (H+L) antibody (Molecular Probes) for anti-hnRNP A1, and Alexa Fluor 594-conjugated anti-human IgG (H+L) antibody (Invitrogen) for GW182.

Candidate siRNA Screen

SMARTpool siRNAs for the screen were purchased from Thermo Scientific (Illkirch, France). BMDMs were plated in 24-well plates and each SMARTpool siRNA was singularly transfected in three wells. 48 hr from the transfection cells were either left untreated or stimulated with 0.25 mM of PA for 18 hr, and total RNA was isolated and analyzed by quantitative RT-PCR. The experiment was repeated 4 times and statistically analyzed using Student's t-Test.

Our screen included enzymes involved in small RNA biogenesis, such as Dicer, Drosha, Ddx-5, Ago1, 2, 3 and 4, Piwil1, 2 and 4, and Elac1 (also known as tRNase Z 1) as well as RNA-binding protein components of the small RNA processing machineries such as Dgcr8, Trbp-2, hnRNP A1, Ilf3 (also known as NF90), Xpo5, Ksrp, Lin28, Zc3h12a (also known as MCPIP1), Ews, p53, and Fus-Tls. In addition, genes implicated in small RNA stability were knocked down such as Zcchc11 (also known as TUTase 4), Zcchc6 (also known as TUTase 7), Xrn2, Exosc2, and RNAseL.

siRNAs and Modified-RNA Oligonucleotides siRNA against mouse p53 and Ro60 were purchased from Ambion. Custom siRNAs or modified-RNA oligonucleotides were synthesized by Eurogentec:

mouse Ago2 5'-GUUGUAUUGUUUAGCGAUU-3' (SEQ ID NO: 22)

mouse hnRNP A1 5'-GCACUAGCCAUCUCUUGC-UUC-3' (SEQ ID NO: 23)

mouse La/SSB 5'-UUCCUUUAAAUCUUCCACC-3' (SEQ ID NO: 25)

mouse Dicer 5' UUCAGCUCGAUGGAUAUGGUG 3' (SEQ ID NO: 55)

mouse si-RNA against RNY1 terminal loop 5'-CAGU-CAGUUACAGAUUGAA-3' (SEQ ID NO:56)

mouse si-RNA against RNY3 terminal loop 5'-CAAC-CAGUUACAGAUUUCU-3' (SEQ ID NO:57)

mouse 2'-OMe-RNA antisense to s-RNY1-5p 5'-UUGA-GAUAACUCACUACCUUCGGACCAGCC-3' (SEQ ID NO: 26)

mouse 2'-OMe-RNA antisense to s-RNY1-3p 5'-AAGACUAGUCAAGUGCAGUAGUGAGAAG-3' (SEQ ID NO: 27)

mouse 2'-OMe-RNA antisense to s-RNY3-5p 5'-UAAACACCACUACUCUCGGACCAACC-3' (SEQ ID NO: 28).

Figure 2:
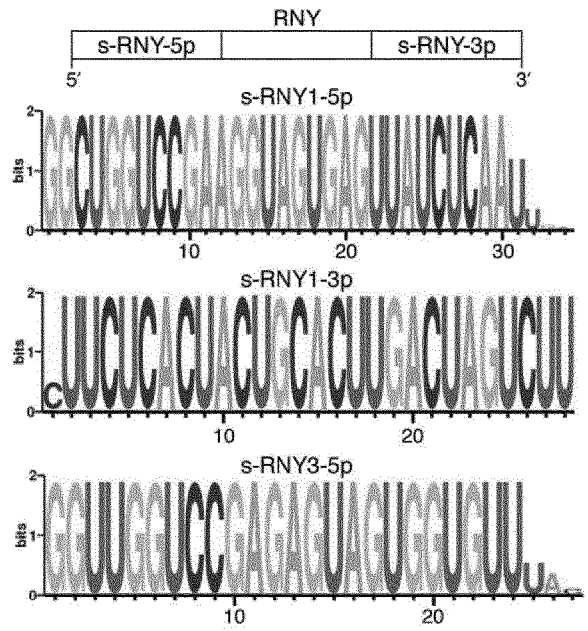
FIG. 2: (A) Bioinformatic analysis of small RNA-Seq data sets identifying a consensus sequence of small RNAs (the s-RNYs) derived from the RNYs in bone marrow derived-macrophages (BMDMs) after M-CSF withdrawal treatment for 36 hr. The bar graph on the top shows the localization of s-RNYs in RNYs. (B) Secondary structure models of mouse RNYs using RNAfold web server (http://rna.tbi.univie.ac.at/cgi-bin/RNAfold.cgi). Arrowheads indicate the mature s-RNYs, arrows indicate the potential cleavage sites of recombinant Ago2 in an in vitro processing assay. Putative hnRNP A1 binding sites are highlighted.
Figure 2:
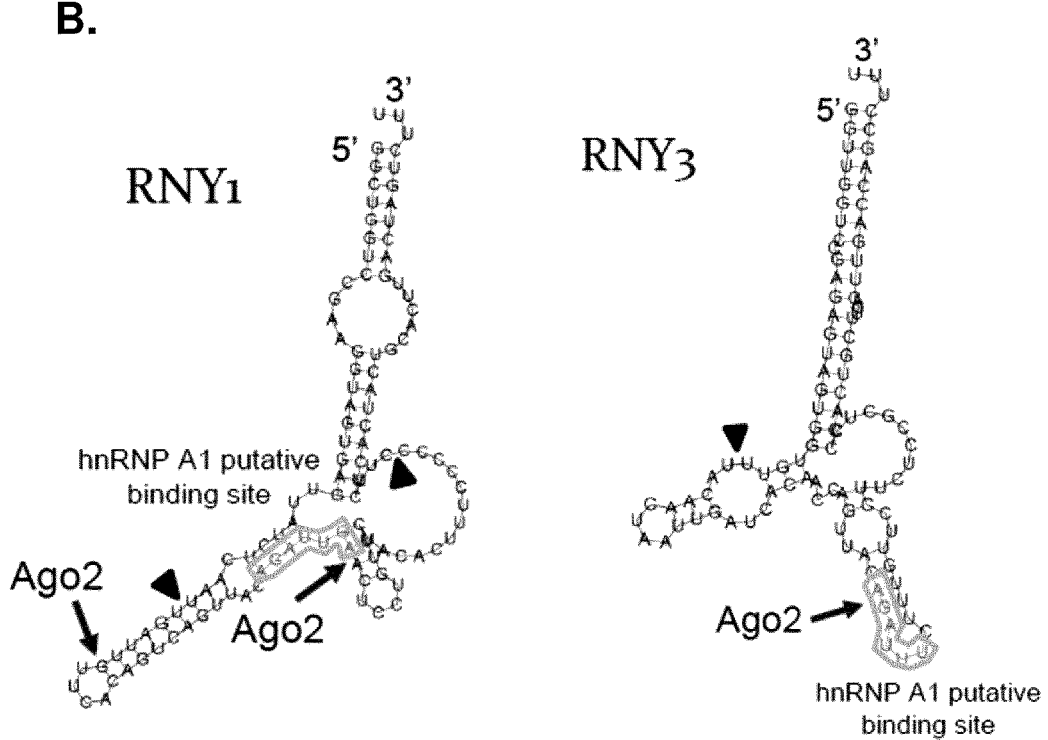

Example 2: Pro-Apoptotic and Atherogenic Stimuli Induce the Expression of RNY-Derived Small RNAs in Macrophages A high-throughput small RNAs sequencing has been performed in primary macrophages stimulated with either staurosporine (STS) or withdrawal of Macrophage-Colony Stimulating Factor (M-CSF) treatment. By mapping the sequencing data to small RNAs databases, including miRNAs, piRNAs, snoRNAs, riRNAs, and tRNAs using the Novoalign program (FIG. 1A), it was shown that apoptotic macrophages highly expressed RNY-derived small RNAs (FIG. 1B). 3 RNY-derived small RNAs were found in mouse and 6 in human varying in length from ~24 to ~34 nt which map to the end and stem regions of the RNYs (FIGS. 1B, 2A and 2B). These small RNAs will be referred hereinafter as s-RNYs, with the mouse s-RNY1-5p being previously classified as piRNA (piRNABank, http://pirnabank.ibab.ac.in/) and the human s-RNY5-3p as miRNA (Meiri, E., et al. (2010) *Nucleic acids research* 38, 6234-6246; Schotte, D. (2009) *Leukemia* 23, 313-322). RNY genes count four copies in human (RNY1, 3, 4, and 5) and two in mouse genome (RNY 1 and 3), and their sequence is well conserved in vertebrates. Northern blot analysis confirmed that the expression of s-RNYs (s-RNY1-5p, s-RNY1-3p, s-RNY3-5p and s-RNY4-5p) was induced in human primary macrophages upon treatment with either STS or withdrawal of M-CSF (data not shown).

Using the stem-loop RT-qPCR method previously described (Mestdagh, P. et al (2008) Nucleic acids research 36, e143), the expression of the s-RNYs derived from the 5' end of RNYs has been investigated in macrophages treated with the pro-apoptotic stimulus lipoteichoic acid (LTA) from the Gram-positive bacteria *Staphylococcus aureus* in combination with an endoplasmic reticulum (ER) stressor, such as thapsigargin (Tg). ER stress renders macrophages susceptible to apoptosis in the face of other pro-apoptotic stimuli. LTA/thapsigargin treatment induces the expression of s-RNYs in bone marrow-derived macrophages (BMDMs) (FIG. 3A), suggesting a general mechanism of s-RNY induction in dying macrophages.

Figure 3:
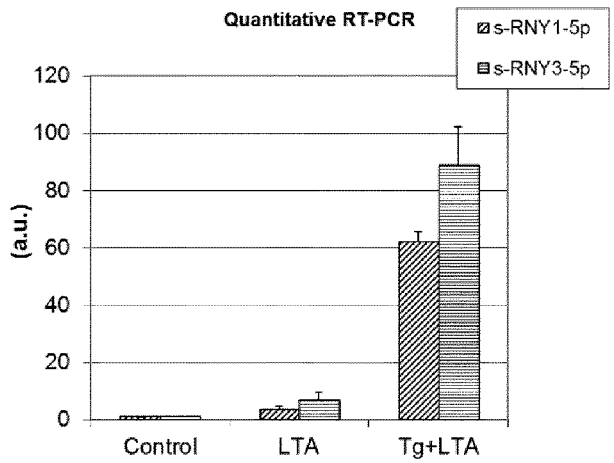
FIG. 3: (A) Quantitative RT-PCR analysis of the indicated s-RNYs in BMDMs incubated for 18 hr with 10 mg/ml LTA (Lipoteichoic acid) alone or in combination with 0.25 µM thapsigargin (Tg). The data were normalized by U2 snRNA. (B) Quantitative RT-PCR analysis of the indicated s-RNYs in BMDMs incubated for 28 hr with 0.25 µM of thapsigargin (Tg) alone or thapsigargin in combination with the indicated concentrations of oxidized-LDL (oxLDL). The data were normalized by U2 snRNA and presented as mean and s.d. (n=8). (C) Quantitative RT-PCR analysis of the indicated s-RNYs in BMDMs incubated for 28 hr with 0.25 µM Tg in combination with the indicated concentration of acetylated-LDL (acLDL). The data were normalized by U2 snRNA.
Figure 3:
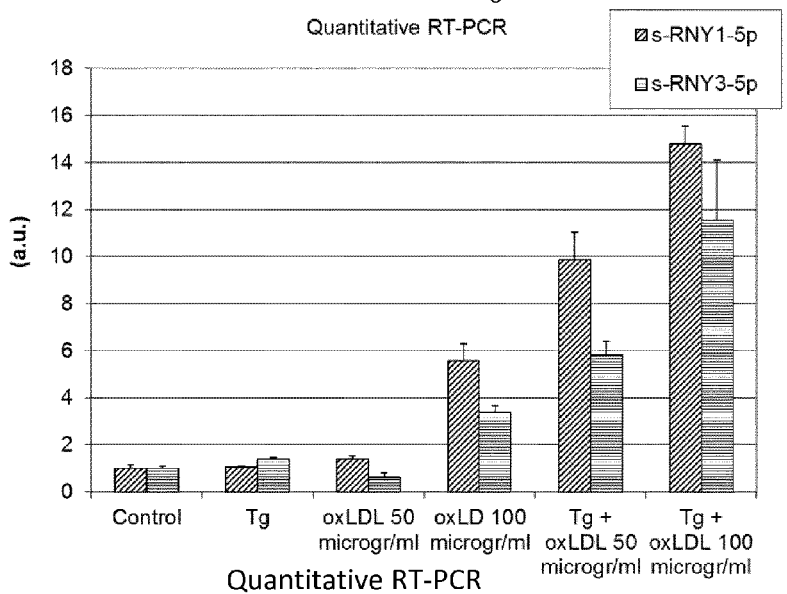
Figure 3:
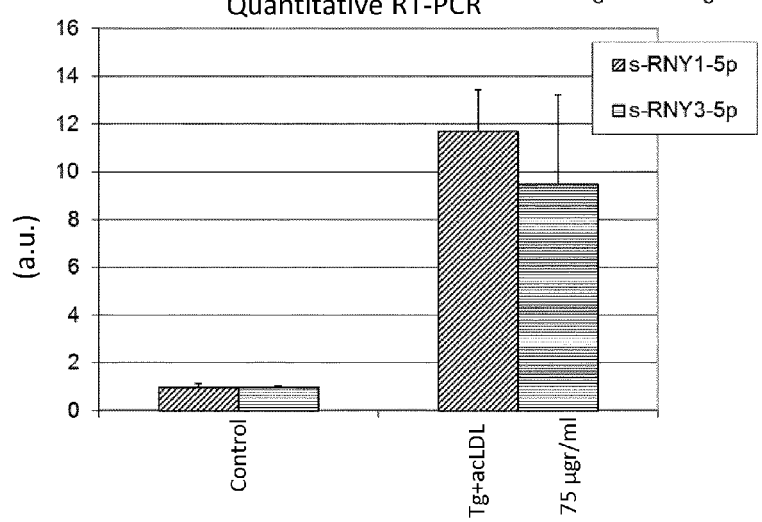
Figure 4:
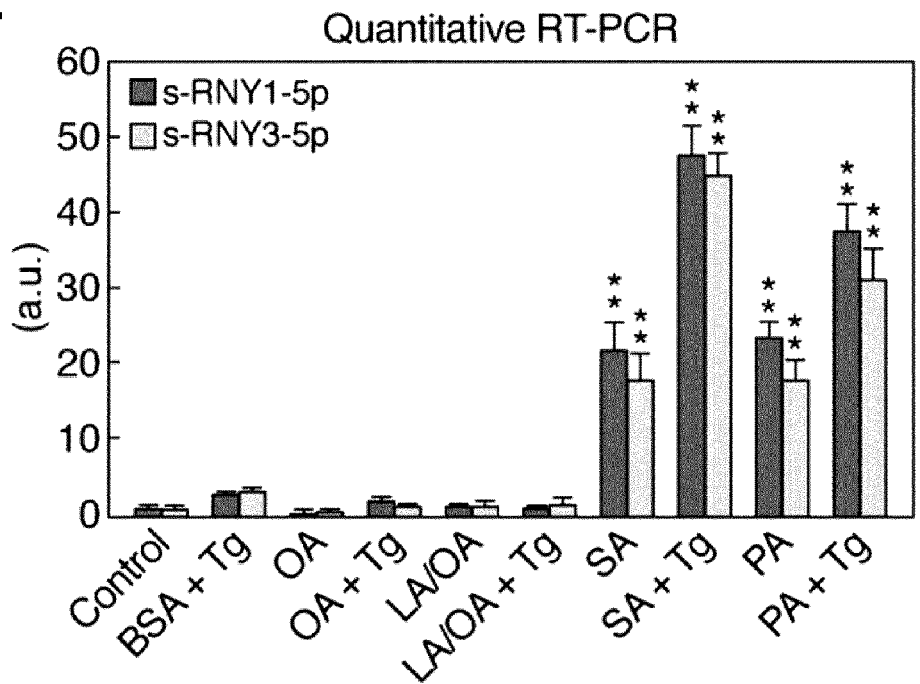
FIG. 4: (A) Quantitative RT-PCR analysis of the indicated s-RNYs in BMDMs incubated for 18 hr with 0.25 µM of thapsigargin (Tg) with BSA, 0.25 mM of the indicated fatty acids in complex with BSA, or thapsigargin plus the fatty acids. The data were normalized by U2 snRNA and presented as mean and s.d. (n=8). The unsaturated fatty acids were linoleic acid (LA) and oleic acid (OA), and the saturated fatty acids were stearic acid (SA) and palmitic acid (PA). Quantitative RT-PCR analysis of the indicated s-RNYs in control or ApoE$^{-/-}$ (B) or Ldlr$^{-/-}$ (C) aortic arches. The mice were fed with either chow diet or high cholesterol diet (HCD). The data were normalized by U2 snRNA and presented as mean and s.d. (n=8 for "B" and n=5 for "C"). Student's t-test: *P<0.05; **P<0.01.
Figure 4:
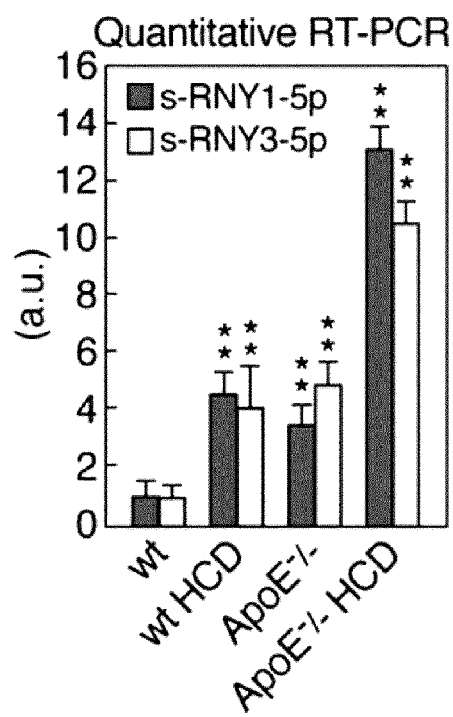
Figure 4:
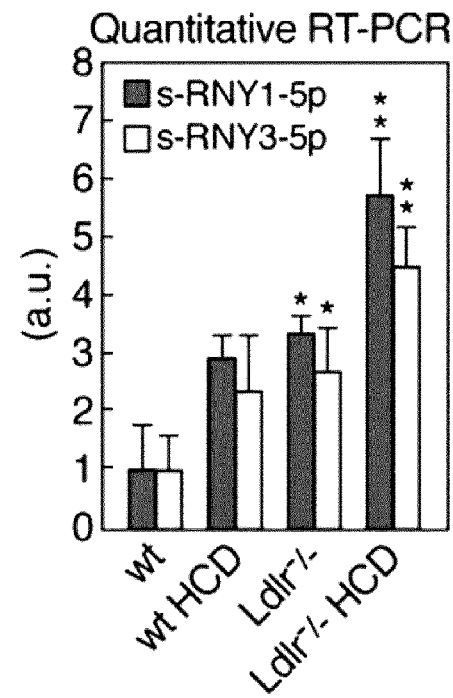

A number of lipids and lipoproteins associated with atherosclerotic diseases conspire with ER stress to cause macrophage apoptosis and progression of atherosclerotic lesions. To determine whether s-RNYs are induced in macrophages stimulated with athero-relevant stimuli, BMDMs have been treated with oxLDL, alone or in presence of thapsigargin. Whereas low dose of oxLDL or thapsigargin alone had no effect, higher level of oxLDL or both reagents together synergistically induced s-RNY expression (RT-PCR analysis for s-RNY1-5p and s-RNY3-5p (see FIG. 3B) and Nothern blot analysis for s-RNY1-3p (data not shown)). Similar results were observed when ER-stressed BMDMs were incubated with acetylated-LDL (acLDL) (FIG. 3C). Different types of fatty acids have been tested then to determine whether they could also trigger s-RNYs induction in macrophages, and if so, whether such an effect was amplified by ER stressor. As shown in FIG. 4A, the unsaturated fatty acids, such as oleic acid and linoleic acid did not induce s-RNY expression when given alone or in combination with thapsigargin. However, when the saturated fatty acids, such as palmitic (PA) and stearic acids, were given alone s-RNY expression was induced, and this effect was increased markedly in the setting of thapsigargin-induced ER stress (RT-PCR analysis for s-RNY1-5p and s-RNY3-5p (see FIG. 4A) and Nothern blot analysis for s-RNY1-3p and s-RNY1-5p (data not shown)). Moreover, to test whether the s-RNYs are induced in animal models for atherosclerosis, ApoE$^{-/-}$, Ldlr$^{-/-}$, and control mice have been compared. ApoE$^{-/-}$ and Ldlr$^{-/-}$ mice were fed with either chow diet or an atherogenic diet containing 1.3% or 1.25% of cholesterol, respectively. As shown in FIGS. 4B and 4C, quantitative RT-PCR from microdissected aortic arches revealed that s-RNYs were significantly upregulated in ApoE$^{-/-}$ and Ldlr$^{-/-}$ mice compared to control, and that high cholesterol diet (HCD) significantly increased their expression levels. Therefore, these results strongly indicate that s-RNY expression is induced in macrophages exposed to various types of apoptotic stimuli, including those that are relevant to atherosclerosis development. Moreover, s-RNYs are expressed in aortas of mouse models for atherosclerosis, raising the possibility that they might play a role in regulating lesion development.

Figure 5:
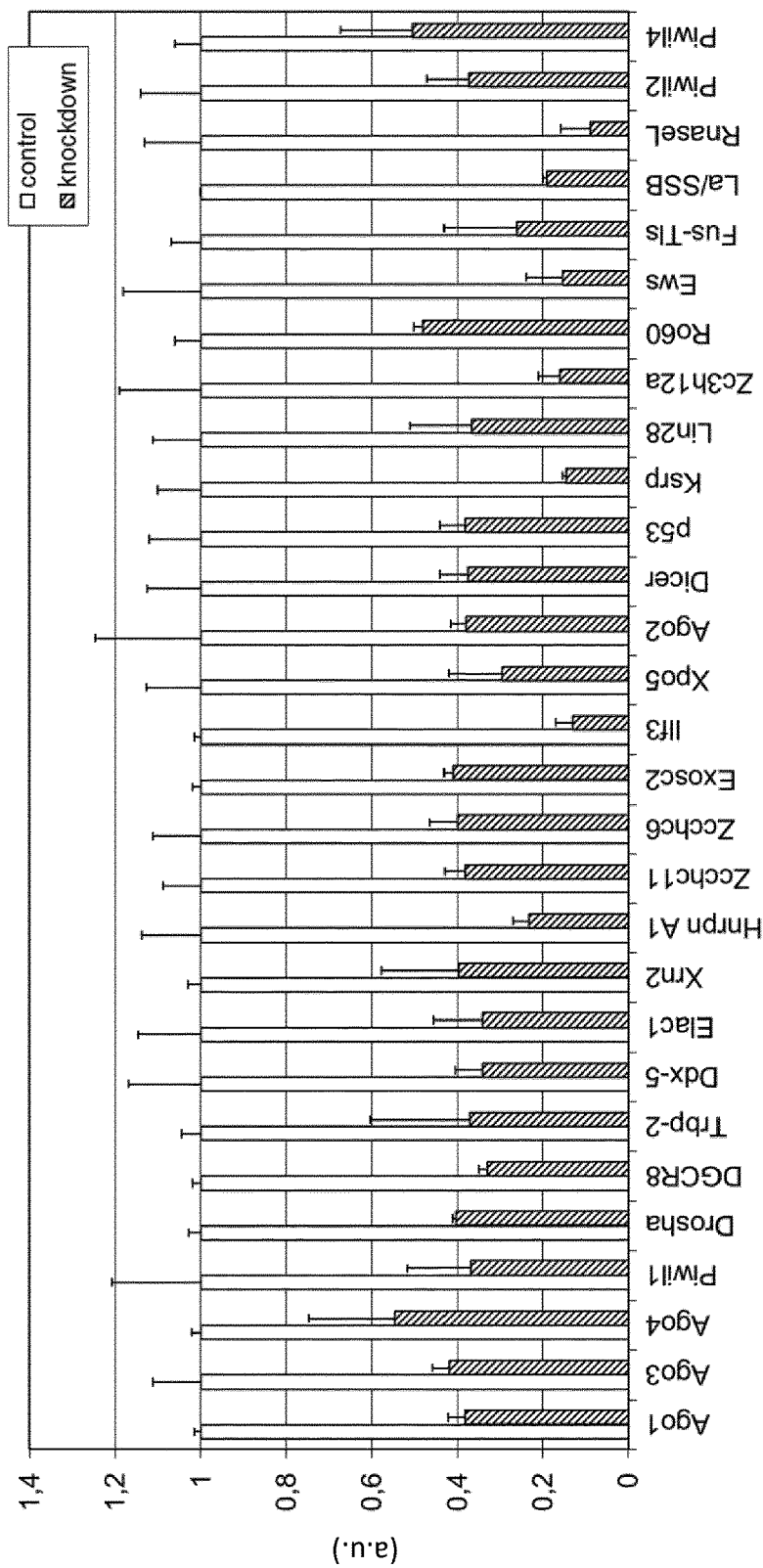
FIG. 5: Effectiveness of the knockdown mediated by SMARTpool siRNAs purchased from Thermo Scientific was assessed in BMDMs. After 48 hr from the transfection total RNA was isolated and analyzed by quantitative RT-PCR analysis. Data were normalized by U2 snRNA and presented as mean and s.d. (n=4). Student's t-test: **P<0.01.
Figure 6:
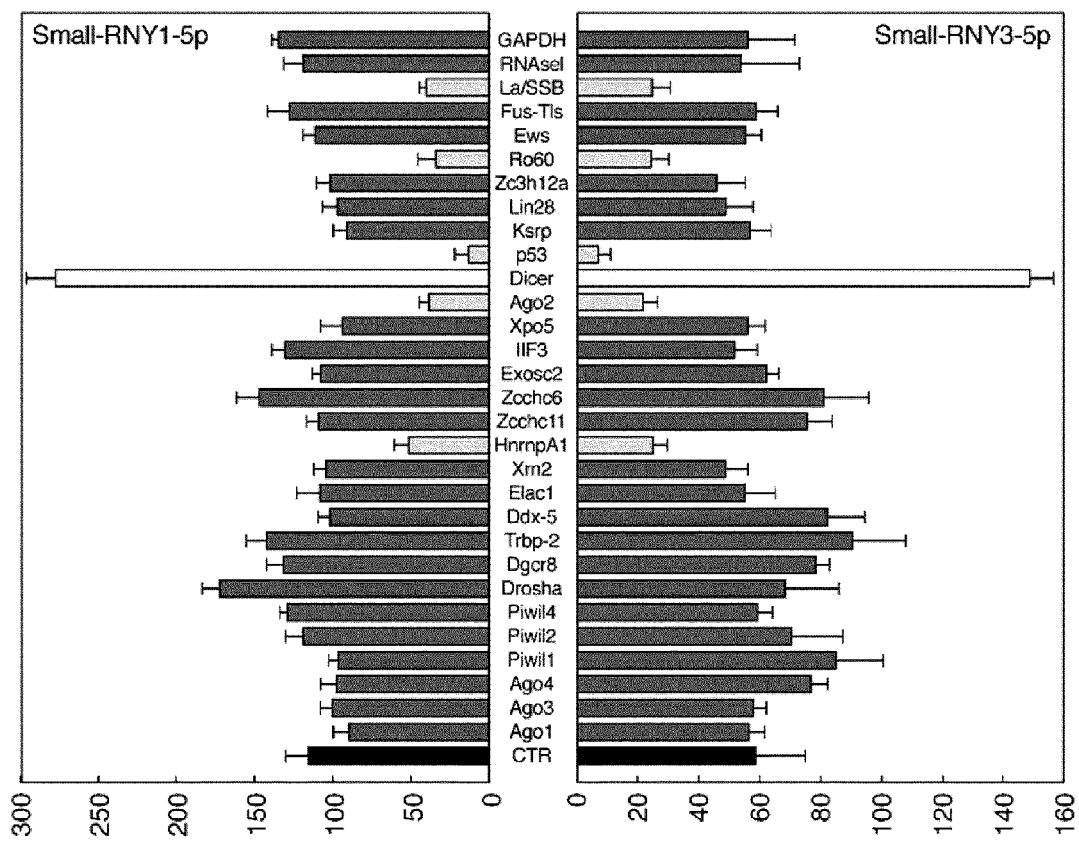
FIG. 6: Depletion of known regulators of small RNA biogenesis pathways and RNA metabolism shows that loss of La/SSB, Ro60, p53, Ago2, and hnRNP A1 (all in light grey) leads to a statistically significant reduction (Student's t-test: P<0.05) of the indicated s-RNYs, while depletion of Dicer leads to a significant induction (Student's t-test: P<0.05). BMDMs were left unstimulated or stimulated with 0.25 mM of PA for 18 hr, and total RNA was isolated and analyzed by quantitative RT-PCR. The data were normalized by U2 snRNA. Data are presented as mean and s.d. (n=4).
Figure 7:
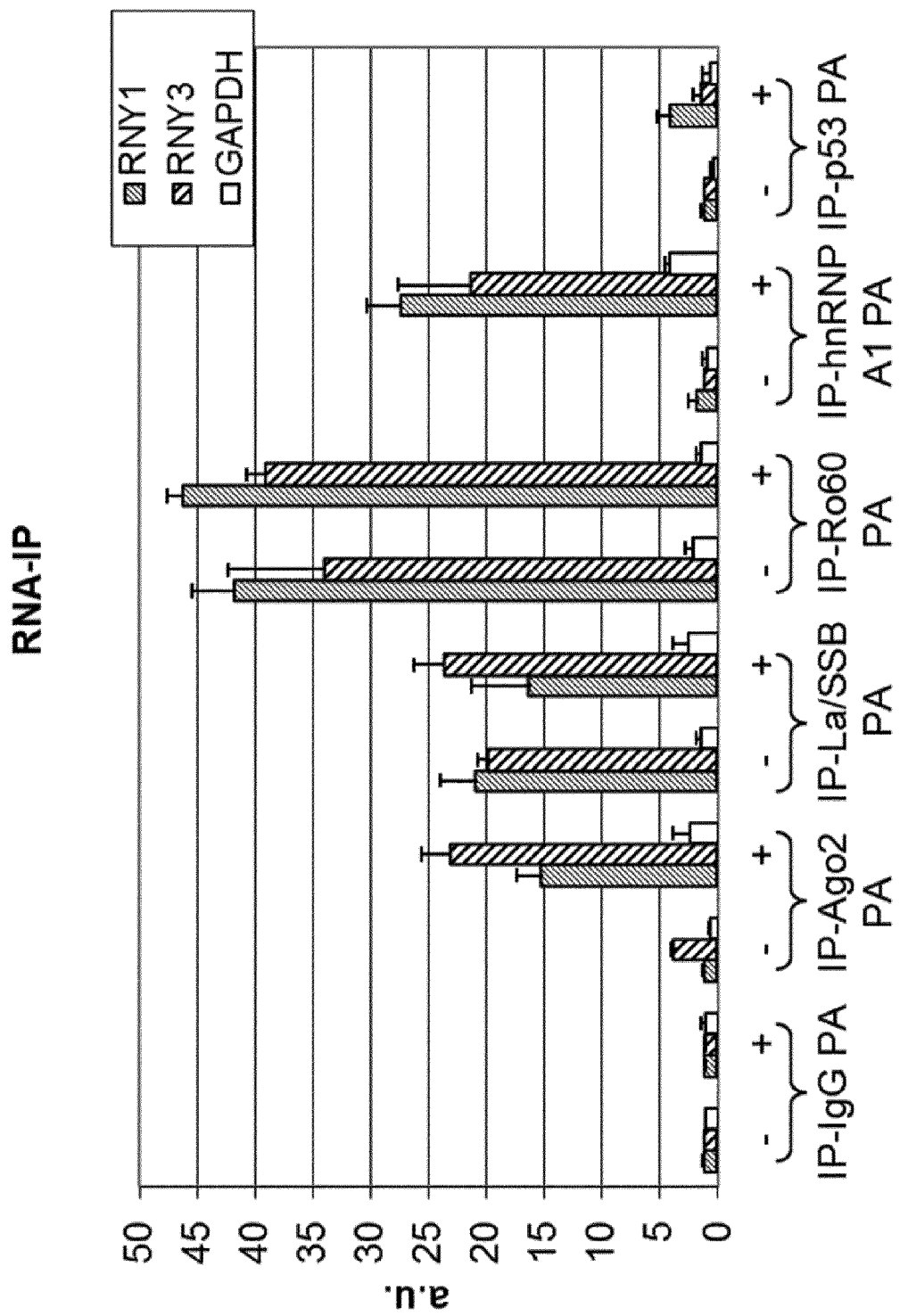
FIG. 7: RNA immunoprecipitation analysis using the indicated antibodies and the indicated RNAs in BMDMs. BMDMs were left unstimulated or stimulated with 0.25 mM of PA for 18 hr and total RNA was isolated and analyzed by quantitative RT-PCR. Data are presented as mean and s.d. (n=6) and normalized with the IgG and the input.

Example 3: Ago2- and hnRNP A1-Dependent Processing of RNYs in Lipid-Laden Macrophages Consistent with the observation that the induction of s-RNY expression (by M-CSF withdrawal or addition of oxLDL in combination with Tg, or PA in BMDM; or addition of STS on cultured human primary macrophages) is always accompanied by a reduction of RNY (Nothern blot analyses performed for s-RNY1-3p/RNY1, s-RNY1-5p/RNY1, s-RNY3-5p/RNY3, and s-RNY4-5p/RNY4; data not shown), a processing upregulation of RNYs has been found in vitro using total cell extracts from PA treated-BMDMs compared to unstimulated control (analyses performed for RNY1/s-RNY1-3p and s-RNY1-5p, and RNY3/s-RNY3-5p; data not shown), overall suggesting that s-RNY expression is modulated at the post-transcriptional level. Because RNYs form a hairpin secondary structure rather similar to that of miRNA precursors (FIG. 2B), an involvement of small RNA processing machinery components in s-RNY maturation has been hypothesized. To validate this hypothesis, a candidate siRNA screen has been performed in PA-treated BMDMs using smart-pool siRNAs to knockdown RNAse and RNA-binding proteins implicated in small RNA biogenesis, as well as Ro60 and La/SSB as RNA-binding proteins associated to the RNYs and forming the so called Ro ribonucleoprotein (RNP) complex (FIG. 5). Among the saturated fatty acids, PA is by far the most potent promoter of macrophage foam cell and apoptosis in atherosclerosis. As shown in FIG. 6, depletion of La/SSB, Ro60, p53, Ago2, and hnRNP A1 significantly decreased the induction of s-RNY expression, compared to Gapdh and non-targeting siRNA controls, as evaluated by quantitative RT-PCR from BMDMs stimulated with PA. In all these cases, s-RNY expression was statistically reduced by more than half. Surprisingly, it has been observed a significant increase of s-RNY expression levels by knocking down Dicer. Northern blot analysis from PA-treated BMDMs transfected with different siRNAs from those used in the siRNA screen, confirmed that the levels of s-RNYs were reduced by 70-90% upon knockdown of Ago2, hnRNP A1, Ro60, La/SSB, and p53 while increased upon Dicer knockdown (data not shown). Importantly, it has been noticed that upon Ago2 or hnRNP A1 knockdown in PA-treated BMDMs the decrease of s-RNY level induction was accompanied by an increase of the RNYs compared to control (Nothern blot analyses performed for s-RNY1-3p, s-RNY1-5p, and s-RNY3-5p; data not shown), suggesting that both Ago2 and hnRNP A1 may directly control the maturation of s-RNYs in lipid-laden macrophages. Conversely, knockdown of Ro60 and La/SSB decreased both s-RNYs and RNYs (data not shown), suggesting that these two proteins may stabilize RNYs and/or s-RNYs, as it was previously proposed. In support to a direct role of Ago2 and hnRNP A1 in regulating RNY processing, both RNYs but not Gapdh (negative control) were immunoprecipitated with antibodies against Ago2 or hnRNP A1 in PA-treated BMDMs while anti-La/SSB and anti-Ro60 antibodies did immunoprecipitate RNYs from both stimulated and unstimulated cells (FIG. 7). However, they did not immunoprecipitate with an anti-p53 antibody. Together, these results strongly indicate that both Ago2 and hnRNP A1 may directly control RNYs processing in lipid-laden macrophages.

Among the proteins found in the siRNA screen, only Ago2 is an enzyme. Ago2 has an endoribonuclease activity for double-stranded RNAs, is the catalytic component of the RISC and is involved in miR-451 processing. Ago2 is associated with different classes of small non-coding RNAs, including miRNAs and siRNAs. To establish whether Ago2 directly interacts with RNYs, recombinant protein and synthetic radiolabeled-RNYs (RNY1, RNY3) have been used in UV-cross-linking assays, which indicated a direct Ago2-RNYs interaction, while the TNF-ARE RNA, used as negative control, did not cross-link (data not shown). These data demonstrated the direct loading of the RNYs into Ago2 and raised the possibility that Ago2 might directly catalyze the maturation of s-RNYs. To check this hypothesis an in vitro processing assay has been performed using naked RNYs and the recombinant Ago2. Processing assay with RNY1 and RNY3 shows that recombinant Ago2 can cleave both RNYs but was unable to generate the final mature form, as speculated taking into account the predicted secondary structure of RNYs (data not shown and FIG. 2B). However, this experiment alone cannot exclude the occurrence of different cleavage sites in vivo due to a protein complex associated with Ago2, as one would expect from the well-established biochemical properties of Ago2. Indeed, Ago2 depletion in BMDM extracts stopped the RNY processing activity while the addition of the recombinant Ago2 was sufficient to rescue the blockade and to generate the full maturation of s-RNYs, as it has been demonstrated for RNY3 (data not shown).

Figure 8:
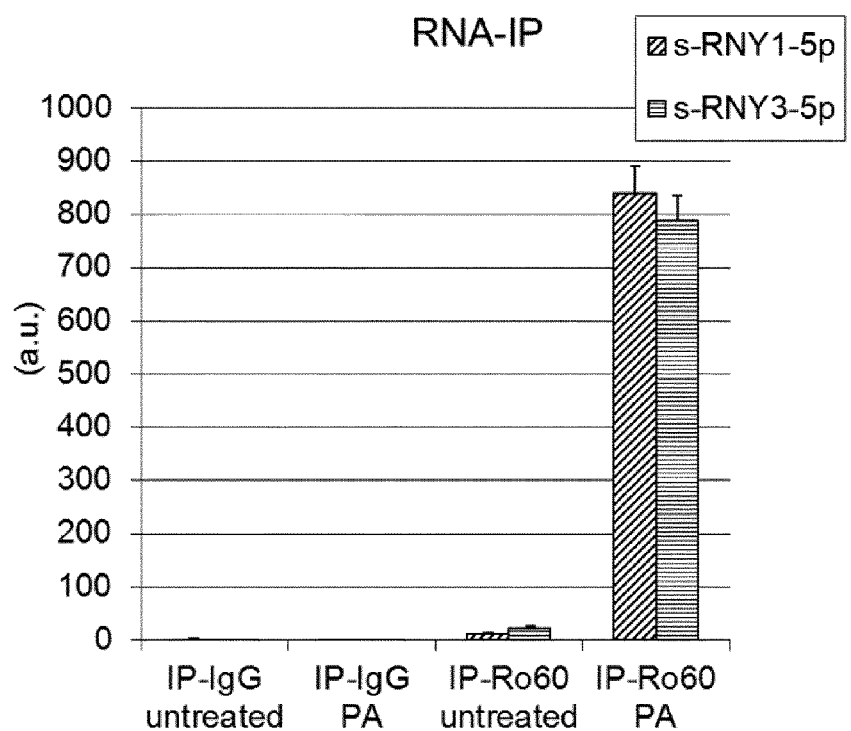
FIG. 8: (A) RNA immunoprecipitation analysis of Ro60 and the indicated s-RNYs in BMDMs. BMDMs were left unstimulated or stimulated with 0.25 mM of PA for 18 hr. RNA was isolated from immunoprecipitation and analyzed by quantitative RT-PCR. Data are presented as mean and s.d. (n=6) and normalized with the IgG and the input. Student's t-test: P<0.01. (B) RNA immunoprecipitation of either Ago2 or La/SSB and the indicated s-RNYs in BMDMs. BMDMs were left unstimulated or stimulated with 0.25 mM of PA for 18 hr. RNA was isolated from immunoprecipitation and analyzed by quantitative RT-PCR. Data are presented as mean and s.d. (n=6). Student's t-test: P<0.01.
Figure 8:
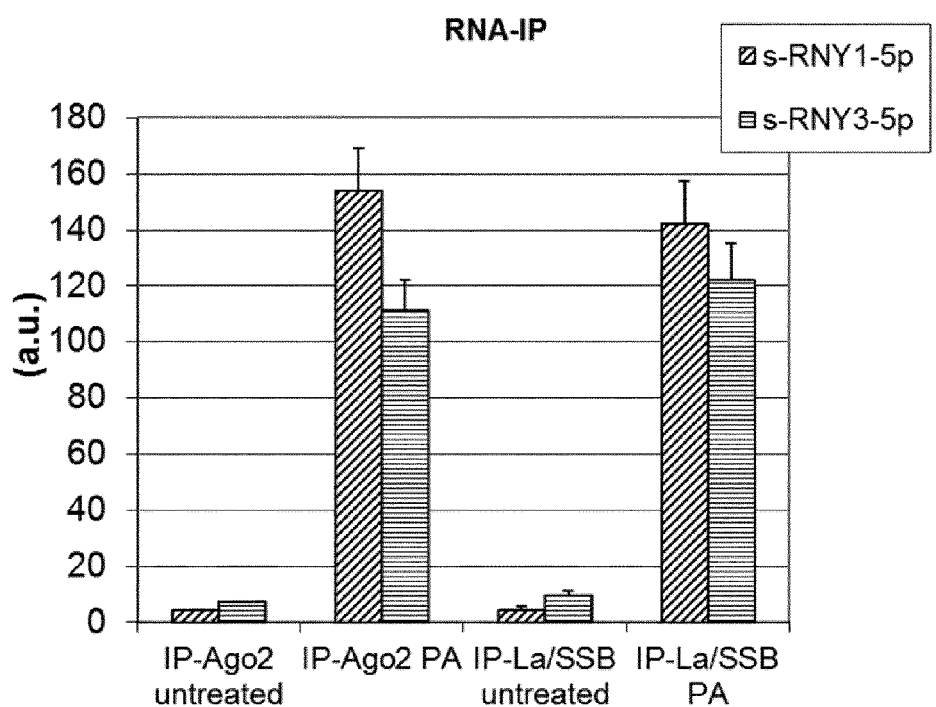

Interestingly, it has been recently reported that both RNY-associated proteins, La/SSB and Ro60, are integral components of Ago2 complex. In particular, previous reports demonstrated that La/SSB is both involved in miRNA processing and turnover of RISC by promoting the release of cleaved mRNA. Coimmunoprecipitation experiments in NIH-3T3 cells revealed that Ago2 interacted with La/SSB in both untreated- and PA-treated cells, while with Ro60 only upon PA treatment (data not shown), indicating that Ago2 is associated to the Ro RNP complex in lipid laden-cells. Moreover, antibodies against Ago2, La/SSB, or Ro60 immunoprecipitated s-RNYs from PA-stimulated BMDMs (FIGS. 8A and 8B), indicating the formation of a protein complex containing s-RNYs. In conclusion, these data strongly demonstrated a s-RNY maturation that proceeds with an Ago2-mediated cleavage.

Next, the possibility that the single-stranded RNA binding protein hnRNP A1 favors the Ago2-dependent processing of RNYs in PA-treated macrophages has been explored. hnRNP A1 is a nucleo-cytoplasmic shuttling protein with roles in many aspects of RNA metabolism. It has been recently reported that hnRNP A1 is involved in miRNA processing by specifically binding to the single-stranded terminal loop structure of selected miRNA precursors to finely modulate the biogenesis. In particular, it binds to miRNA precursors to induce a change in the secondary structure creating a more favorable cleavage site for Drosha. The data reveal that hnRNP A1 coimmunoprecipitated with Ro60 (data not shown) and that anti-hnRNP A1 antibody immunoprecipitated both RNYs in PA-stimulated BMDMs (FIG. 7). To establish whether hnRNP A1 interacts directly with RNYs, recombinant protein and in vitro transcribed RNY have been used in UV-cross-linking assays, which indicated a direct hnRNP A1-RNYs interaction (RNY1 and RNY3; data not shown) while the RNA binding protein KSRP, used as negative control did not cross-link to RNY1 or RNY3 (data not shown). The pri-let7-a, was used as a positive control, crossed-link to KSRP (data not shown). Interestingly, both RNY1 and RNY3 share some similarities with the hnRNP A1 binding sequence to the terminal loop of miR-18a precursors (FIG. 2), indicating that, as for miRNA precursors, hnRNP A1 binding to RNYs may create a more favorable cleavage site. Indeed, the presence of hnRNP A1 promotes the Ago2 cleavage (data not shown). Furthermore, because hnRNP A1 knockdown in PA-treated BMDMs abrogated the interaction of Ago2 with both RNY1 and RNY3 (FIG. 9A), it was concluded that hnRNP A1 favors the association of Ago2 to RNYs in lipid-laden macrophages. Therefore, these data indicate that hnRNP A1 is a key regulator of RNYs processing in lipid-laden macrophages based on its affinity binding to RNYs. Upon binding, hnRNP A1 could optimize the positioning/recruitment of Ago2 through a protein-protein interaction. Indeed, in PA-stimulated BMDMs, a RNAseA independency of the interaction between Ago2 and hnRNP A1 has been demonstrated (data not shown). In support of this conclusion, hnRNP A1 cytoplasmic levels dramatically increased during PA treatment of BMDMs (data not shown) and in Mac3-positive macrophages in aortic sinus of ApoE$^{-/-}$ mice (data not shown). The cytoplasmic localization of hnRNP A1 would promote the interaction to Ago2 and then the processing of RNYs. Overall, these results indicate that in lipid-laden macrophages the processing of RNYs is mediated by the Ago2/hnRNP A1 complex.

Example 4: Post-Transcriptional Regulation of Target mRNAs by S-RNYs

Figure 9:
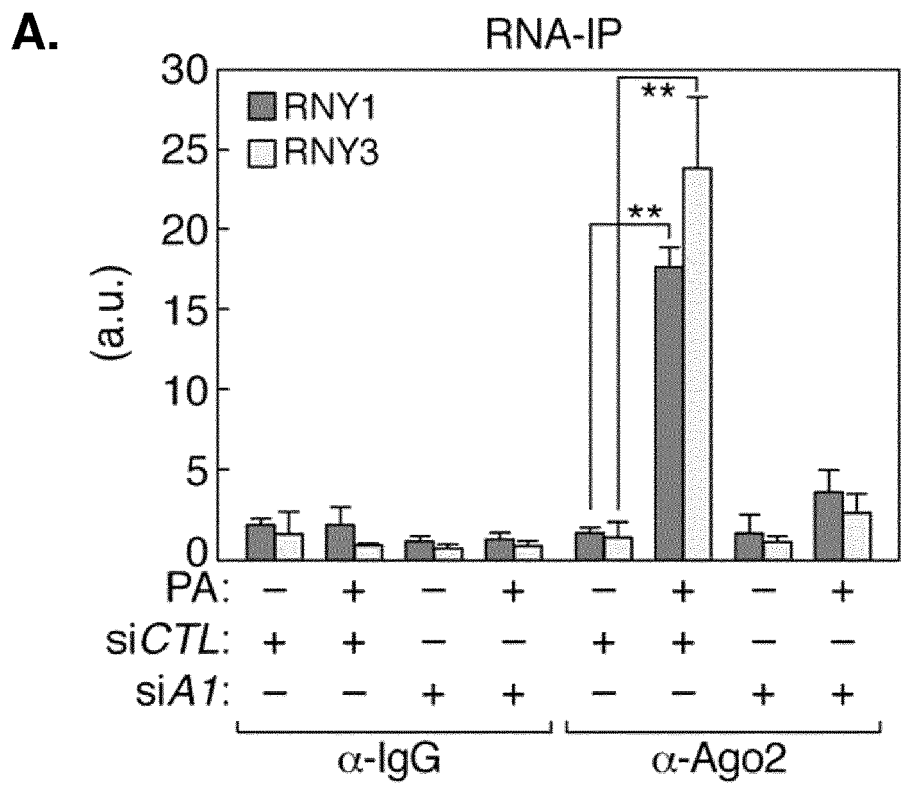
FIG. 9: (A) RNA immunoprecipitation of either Ago2 or IgG and the indicated RNYs in BMDMs. BMDMs were transfected with the indicated siRNAs and either left unstimulated or stimulated with 0.25 mM of PA for 18 hr. RNA was isolated from immunoprecipitation and analyzed by quantitative RT-PCR. Data are presented as mean and s.d. (n=6). Student's t-test: **P<0.01. (B) RNA immunoprecipitation analysis of GW182 and the indicated s-RNYs. BMDMs were left unstimulated or stimulated with 0.25 mM of PA for 18 hr. RNA was isolated from immunoprecipitation and analyzed by quantitative RT-PCR. Data are presented as mean and s.d. (n=6) and normalized with the IgG and the input.
Figure 9:
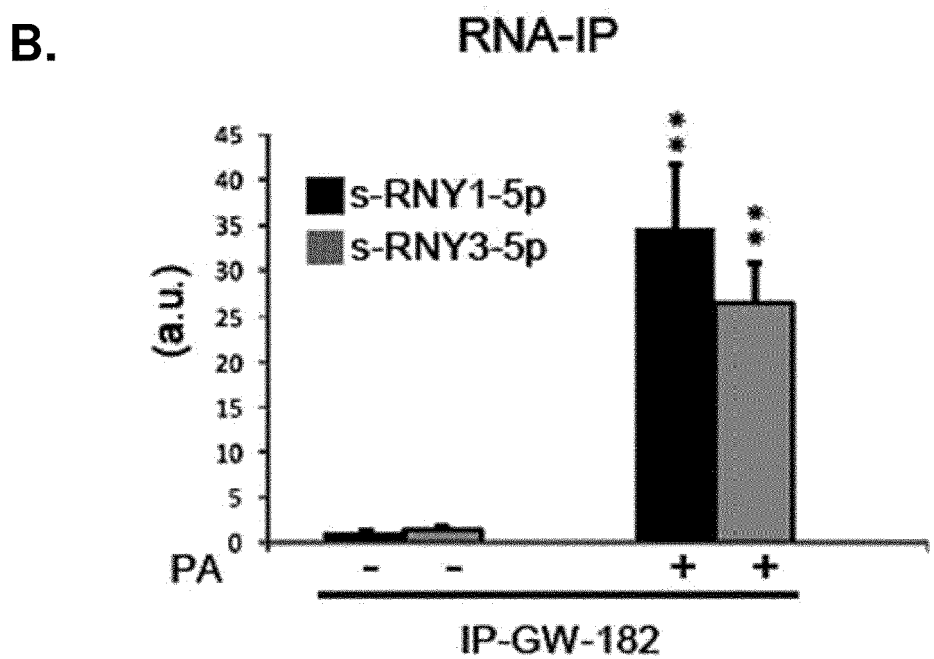

Given that s-RNYs are associated with Ago2 (FIG. 8B), the possibility that they might exert a post-transcriptional control of gene expression comparable to that of miRNAs has been explored, to target mRNAs by recognition of complementary sequences. It has been first determined whether s-RNYs localize to the Processing bodies (P-bodies), which serve as sites for RNA degradation mediated by small RNAs, such as miRNAs, piRNAs, and riRNAs. A fluorescence in situ hybridization has been performed followed by immunostaining (immuno-FISH) using a FAM conjugated-LNA probe to s-RNY1-5p together with immunofluorescent staining of GW182, as marker for the P-bodies. Although, the LNA probe used here can recognize both RNY1 and s-RNY1-5p, a change in the LNA-staining pattern has been noticed in BMDMs upon PA stimulus. In untreated BMDMs the RNY1 signal was diffused in all cytoplasm, while in PA-treated BMDMs the RNY1/s-RNY1-5p signal was a cytoplasmic dot staining pattern similar to that of GW182 (data not shown). Notably, the RNY1/s-RNY1-5p signal partially colocalized with GW182 in PA-treated BMDM (data not shown). Most importantly, RNA immunoprecipitation analysis demonstrated that GW182 interacts with s-RNYs in PA-treated BMDMs (FIG. 9B). Therefore, these data indicate that s-RNYs localize to the P-bodies in lipid-laden macrophages.

To determine the existence of direct targets of s-RNYs, microarray experiments were performed from BMDMs overexpressing s-RNYs and control. Because siRNA against the terminal loop of RNY1 or RNY3 generates s-RNYs associated to Ro60 mimicking the induction of the processing that occur in lipid-laden macrophages and apoptotic macrophages (demonstrated for s-RNY1-3p, s-RNY1-5p, and s-RNY3-5p; data not shown), this strategy has been used instead of overexpressing ectopic mimic s-RNYs. This approach would avoid any off-target effects due to the overexpression of ectopic s-RNYs. Direct s-RNY target mRNAs were expected to be enriched among the mRNAs that are downregulated in BMDMs overexpressing s-RNYs compared to control.

Figure 10:
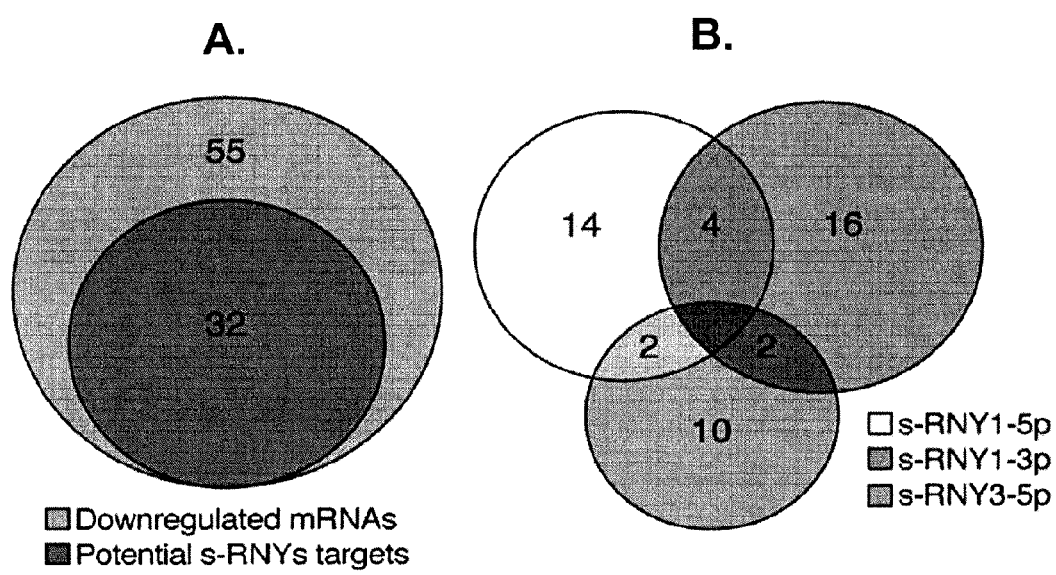
FIG. 10: (A) Venn diagram showing the potential s-RNYs target-mRNAs among the downregulated mRNAs detected from a microarray analysis of BMDMs overexpressing s-RNYs and control from 4 independent experiments. (B) Venn diagram showing the number of potential target-binding sites for each s-RNYs in both coding region and 3UTR of downregulated mRNAs of s-RNYs-overexpressing BMDMs.
Figure 11:
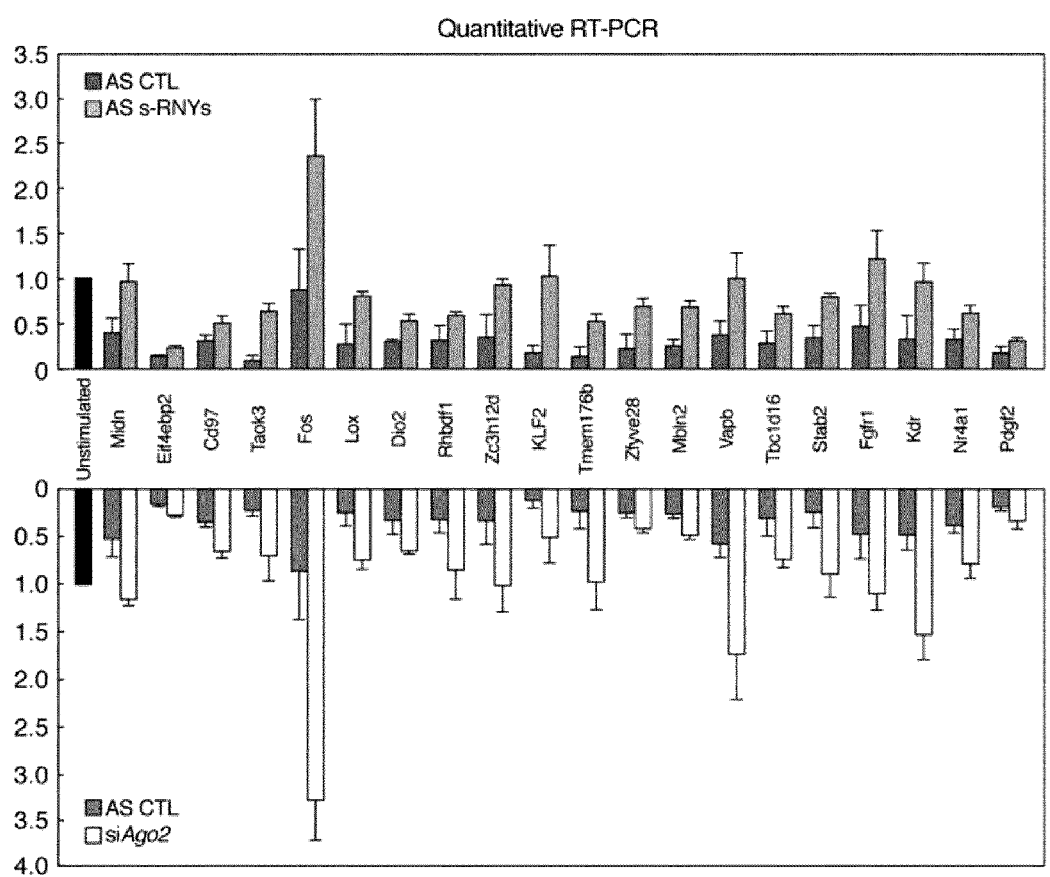
FIG. 11: Quantitative RT-PCR analysis of the potential s-RNYs-target mRNAs in BMDMs transfected with siAgo2, 2'-OMe-RNA antisense oligonucleotides (AS) to s-RNYs, or control. BMDMs were left unstimulated (black column) or stimulated with 0.25 mM of PA for 18 hr, and total RNA was isolated and analyzed. Data were normalized by U2 snRNA and are presented as mean and s.d. (n=6).

The 57 mRNAs statistically downregulated of at least 1.2 fold change in s-RNYs-overexpressed BMDMs were analyzed for the presence of potential binding sites for s-RNYs using Sylamer bioinformatic program (van Dongen, S., et al (2008) *Nature methods* 5, 1023-1025). Because miRNAs use a seed sequence of 6-8 nt in their 5' end to target both the 3' untranslated region (3UTR) and the coding region (CDS) of mRNAs, it has also been searched for at least 7 nt of sequence complementary between s-RNYs 5' end sequence and both 3UTR and CDS of the downregulated genes. As expected a significant enrichment of s-RNYs targets was observed in the downregulated mRNAs, about 56% (32 mRNAs) (FIGS. 10A and 10B). Consequently, genes regulated by s-RNYs would be affected in PA-treated macrophages transfected by siAgo2 or s-RNYs inhibitors. Indeed, the expression of at least 20/32 mRNAs (about 62%) were Ago2 and s-RNYs dependent, as evaluated by quantitative RT-PCR in PA-treated BMDMs transfected with siAgo2, 2'-OMe-RNA antisense oligonucleotides to s-RNYs, or control (FIG. 11; and data not shown). These data indicate that the altered mRNA expression profile of BMDMs expressing s-RNYs exhibits a signature that could be mediated by a direct target of mRNA by s-RNYs.

Figure 12:
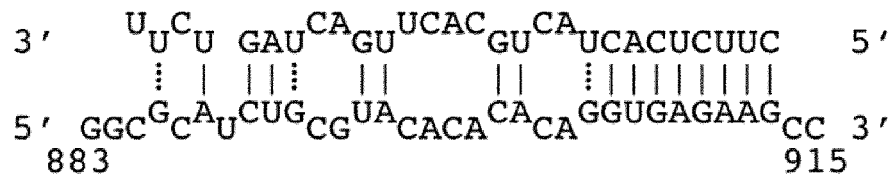
FIG. 12: (A) RNA duplex expected to result from base pairing of KFL2 mRNA with s-RNY1-3p. A-U and G-C base pairs are represented by solid lines; G-U wobble base pairs are represented by dotted lines, shown herein as SEQ ID NOS 58 and 59, respectively. (B) The sequence of the predicted target site of KFL2 mRNA from the indicated species, shown herein as SEQ ID NOS 60-63, respectively. The s-RNY1-3p seed complementary sequence is enclosed by a black box. Nucleotide conservation across the species is indicated by asterisks. (C) Relative luciferase activity of reporter constructs containing two either wt or mutant s-RNY1-3p binding sites (BS) from KFL2 mRNA sequence in NIH-3T3 cells transfected with either 2'-OMe-RNA antisense oligonucleotide to s-RNY1-3p or control. Cells were left unstimulated or stimulated with 0.25 mM of PA for 18 hr. The data were normalized using Renilla activity. Data are presented as mean and s.d. (n=4). Student's t-test: **P<0.01.
Figure 12:
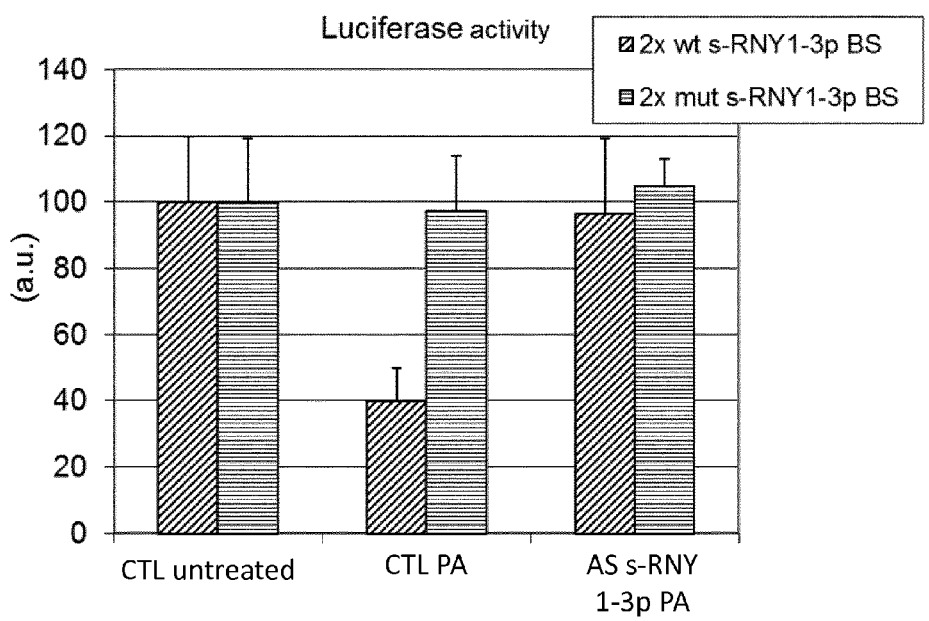

Interestingly, in the list of the potential s-RNYs direct target-mRNAs, some genes have been clearly demonstrated to be important in regulating the pathogenesis of atherosclerosis, the cell survival and the anti-inflammatory response Fos, Krüppel-like factor 2 (KLF2), Zfyve28, Rhomboid family-1 (Rhbdf1), Fgfr1, Lysyl oxidase (Lox) and Nr4a1 (also known as Nur77). In particular, KLF2 is a transcription factor having an anti-apoptotic and an anti-inflammatory role in macrophages. KLF2 is downregulated in atherosclerotic lesions of ApoE-/- and Ldlr-/- mice compared to control and mice bearing the double knockout for ApoE and KLF2 develop more severe and faster atherosclerotic lesions compared to control, indicating a protective role of this gene. Western blot experiments confirmed that the downregulation of KLF2 expression in PA-treated BMDMs was indeed rescued by the knockdown of Ago2 or of s-RNYs (data not shown), indicating a major role played by s-RNYs in regulating the expression of this gene. According to bioinformatic predictions, there is a single s-RNY1-3p binding site in KLF2 mRNA (FIG. 12A). Sequence conservation across vertebrates was strongest in the segment showing complementary to the seed region of s-RNY1-3p (FIG. 12B). To assess whether KLF2 mRNA is directly targeted by s-RNY1-3p, a reporter construct has been made containing 2 copies of the wild-type (wt) sequence of KLF2 having the binding site for s-RNY1-3p, and the mutant one cloned downstream to a luciferase CDS. Importantly, PA treatment of NIH-3T3 cells repressed luciferase activity of the reporter construct containing the wt sequence which was rescued by the knockdown of s-RNY1-3p (FIG. 12C). In contrast, the mutant reporter construct was not affected. Altogether, these data indicate that s-RNY expression affects the modulation of gene expression in lipid-laden macrophages by directly regulating at the post-transcriptional level a critical subset of mRNAs for the pathogenesis of atherosclerosis development, as it has been demonstrated for KLF2.

Figure 13:
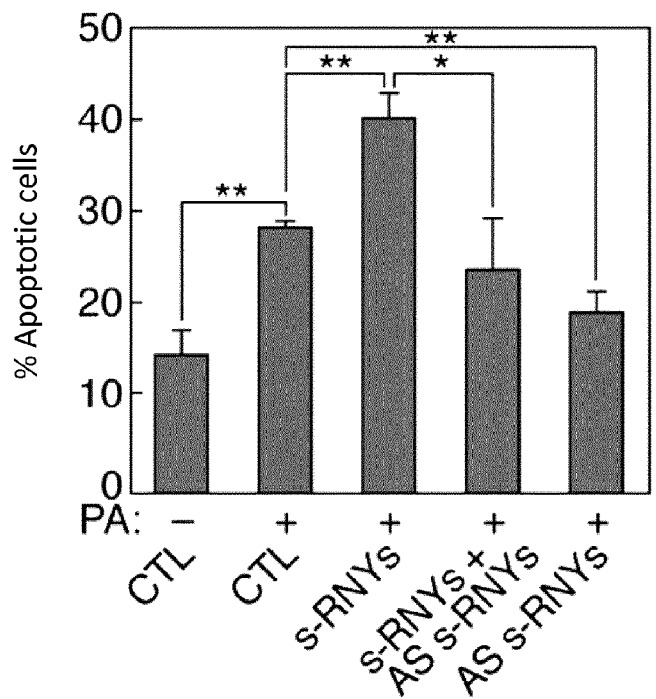
FIG. 13: Apoptotic data by fluorocytometry for BMDMs overexpressing s-RNYs, transfected with either 2'-OMe-RNA antisense oligonucleotides to s-RNYs or control. BMDMs were stimulated with 0.25 mM of PA for 18 hr (A), 0.25 μM thapsigargin (Tg) in combination with 100 μM of oxLDL for 28 hr (B), or left unstimulated (C). Percentage of apoptotic and necrotic cells was determined by staining with Dapi and annexin V-Alexa568. Data are presented as mean and s.d. (n=3).
Figure 13:
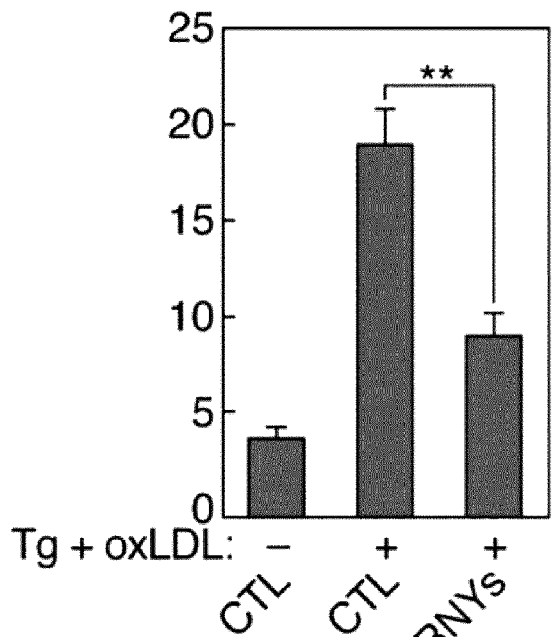
Figure 13:
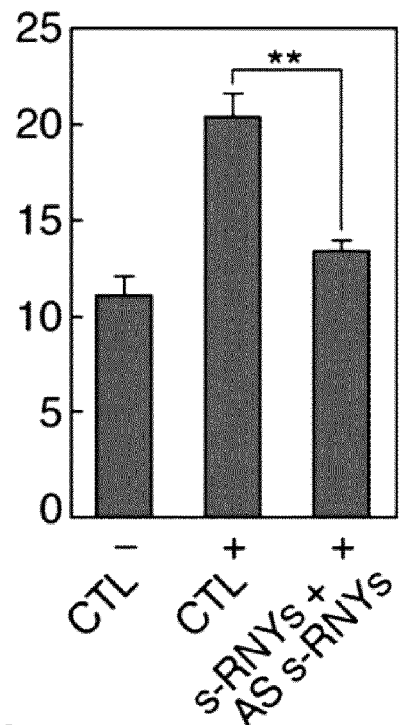

Example 5: s-RNYs Regulate Apoptosis and Inflammatory Response in Lipid-Laden Macrophages In accordance with previous reports (Scull, C. M., and Tabas, I. (2011). *Arteriosclerosis, thrombosis, and vascular biology* 31, 2792-2797; Seimon, T. A et al. (2010). *Cell metabolism* 12, 467-482), FIGS. 13A and 13B show an apoptosis activation in macrophages treated with pro-atherogenic stimuli, such as PA or Tg in combination with oxLDL. Hence, the effects of s-RNYs on BMDMs apoptosis using flow cytometry have been evaluated. As shown in FIG. 13A, induction of s-RNYs maturation by using siRNA against the terminal loop of RNYs causes an upregulation of the apoptosis mediated by PA treatment, which is rescued by co-transfecting the 2'-OMe-RNA antisense oligonucleotides (SEQ ID NO: 26, SEQ ID NO: 27 and SEQ ID NO: 28) to s-RNYs. Moreover, a downregulation of the apoptosis is observed when the endogenous s-RNY expression is knocked down in BMDMs treated with PA or oxLDL (FIGS. 13A and 13B). Notably, by promoting s-RNY maturation the apoptosis is induced in untreated BMDMs, which is also rescued by co-transfecting the 2'-OMe-RNA antisense oligonucleotides to s-RNYs (FIG. 13C). Furthermore, 2'-OMe-RNA antisense oligonucleotide to s-RNYs inhibits the activation of caspase-3 in PA-treated BMDMs (data not shown) while s-RNYs overexpression is able to activate it in unstimulated BMDMs (data not shown). Therefore, these results indicate that atherogenic stimuli-induced s-RNYs are an intrinsic component of the machinery regulating apoptosis in lipid-laden macrophages.

Figure 14:
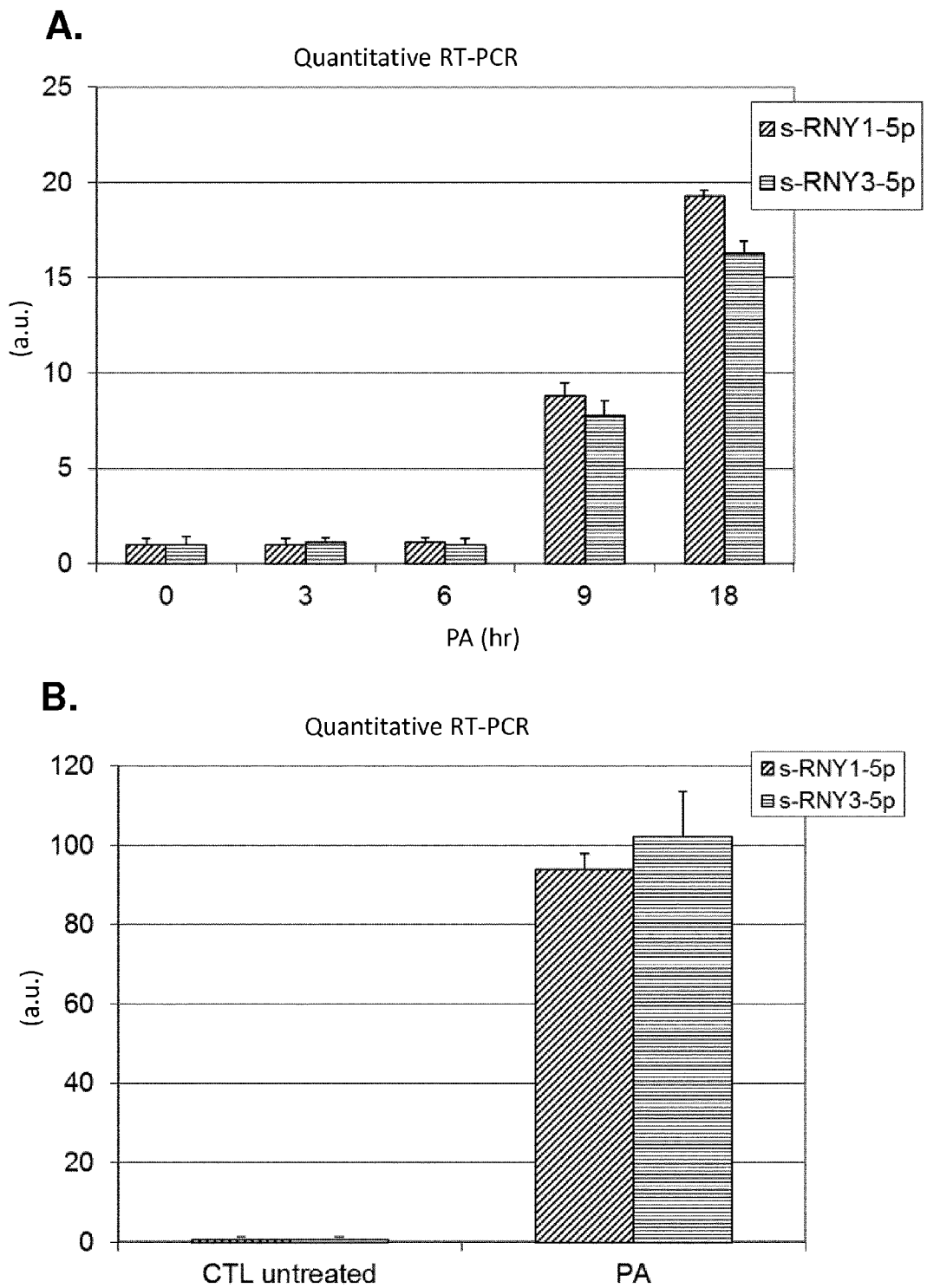
FIG. 14: (A) Quantitative RT-PCR analysis of the indicated s-RNYs in BMDMs incubated with 0.25 mM of PA the indicated time. The data were normalized by U2 snRNA. (B) Quantitative RT-PCR analysis of the indicated s-RNYs from the medium of BMDMs. Cells were left unstimulated or incubated with 0.25 mM PA for 18 hr. Data were normalized by using the synthetic non-mammalian cel-miR-39, which was added to the samples before the RNA extraction. Data are presented as mean and s.d. (n=8).
Figure 15:
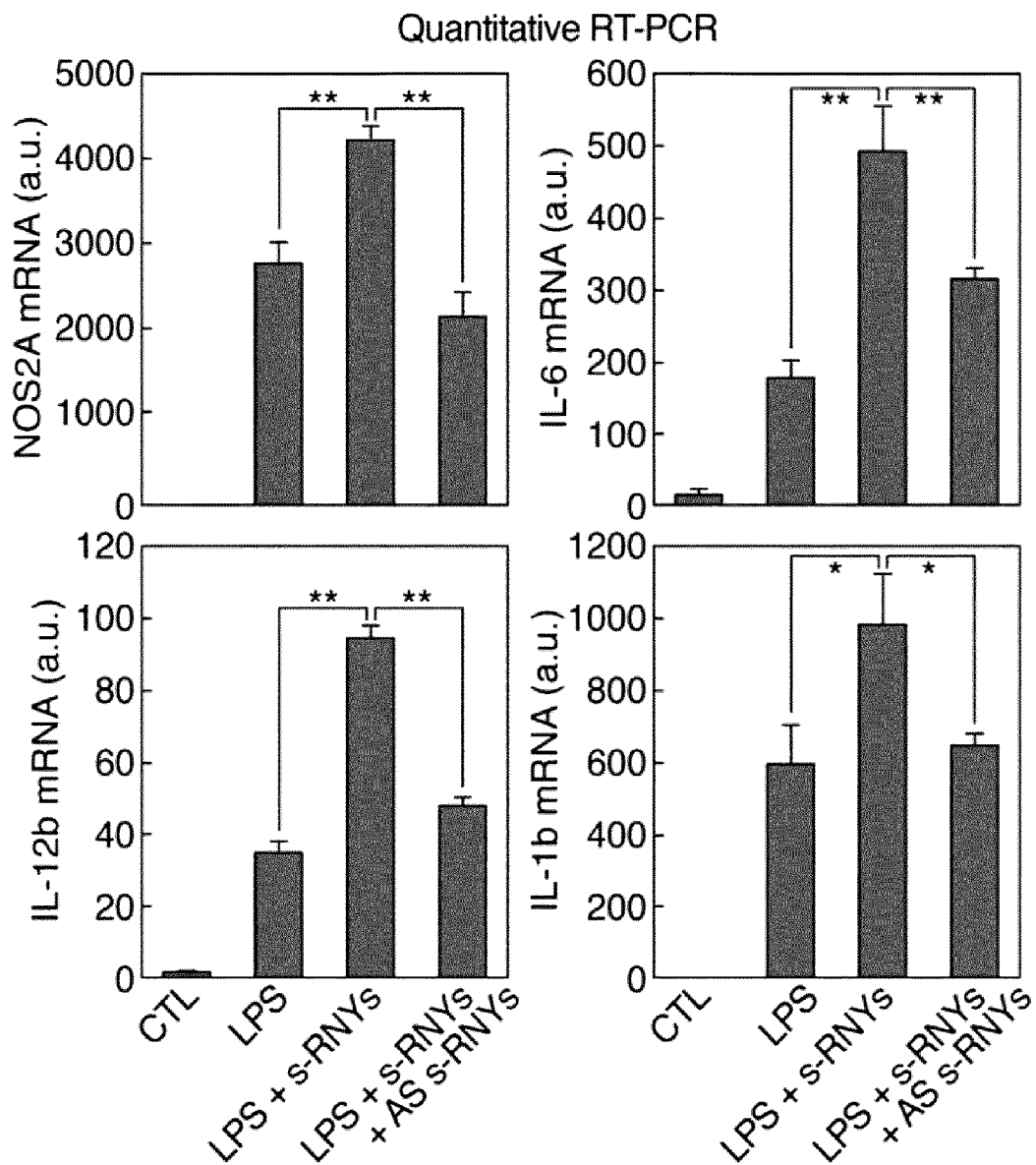
FIG. 15: Quantitative RT-PCR analysis of NOS2A, IL-6, IL-12b, and IL-1b transcripts in BMDMs overexpressing s-RNYs and transfected with either 2'-OMe-RNA antisense oligonucleotides to s-RNYs or control. BMDMs were left unstimulated or stimulated with 100 ng/ml LPS for 12 hr, and total RNA was isolated and analyzed. Data were normalized by U2 snRNA and are presented as mean and s.d. (n=4). Student's t-test: *P<0.05; **P<0.01.

Given that PA treatment promotes both apoptosis and inflammatory response in macrophages by regulating signaling pathways downstream Toll-like receptors (TLR) activation, including c-Jun NH2-terminal kinase (JNK), NF-κB, and p38, it has been hypothesized that s-RNYs may regulate PA mode of action in macrophages by ultimately modulating these signaling pathways. Time course experiments revealed that PA enhanced p38 activation, which depends on p38 phosphorylation, starting by 9 hr while NF-κB activation, which depends on IκBα degradation, after 9 hr of treatment (data not shown). As previously reported, free fatty acids treatment of BMDMs did not significantly enhance the JNK activation upon phosphorylation (data not shown). Interestingly, s-RNY expression was induced by 9 hr of PA treatment in BMDMs (FIG. 14A) suggesting a timing correlation between s-RNYs induction and cell signaling activation, and a possible role of s-RNYs in regulating them. In fact, the inventors have demonstrated that NF-κB and p-38 activation are both reduced upon s-RNYs knockdown in PA-treated BMDMs (data not shown), indicating that s-RNYs promote the activation of both signaling pathways. Consistent with this conclusion, s-RNYs overexpression in BMDMs strongly increased the PA-induced expression of NF-κB-target genes, as it was demonstrated for nitric oxide synthase 2 (NOS2A) (data not shown). Moreover, the effect of inducing s-RNY maturation on the expression regulation of death cytokines and nitric oxide activated by NF-κB pathway has been tested in BMDMs treated with the general macrophage activator lipopolysaccharide (LPS). As shown in FIG. 15, s-RNYs enhanced a significant upregulation of the mRNAs encoding for NOS2A, interleukin (IL)-6, IL-12b, and IL-1b. Therefore these data indicate that s-RNYs activate p38 and NF-κB pathways to ultimately promote cell death and pro-inflammatory response in macrophages.

Example 6: s-RNYs are Upregulated in the Blood of Mouse Models for Atherosclerosis and in Patients with Coronary Artery Disease Significant amounts of miRNAs have been recently found in extracellular body fluids, including blood, urine, saliva, and semen. Some circulating miRNAs in the blood have been successfully revealed as biomarkers for several human disorders, such as many cancers, cardiovascular diseases, and brain and liver injuries. To evaluate whether s-RNYs may be considered as novel biomarkers for atherosclerosis-derived diseases, the presence of s-RNYs in the extracellular environment has first been determined. For that purpose, RNA was isolated from the medium of PA-treated BMDMs and s-RNY expression levels were measured by quantitative RT-PCR (FIG. 14B). PA treatment resulted in a ~100-fold enrichment of s-RNYs in extracellular environment compared to control. Like miRNAs, s-RNYs are also strikingly stable in cell culture medium. Indeed, Northern blot from a combination of medium and debris of BMDMs treated with STS at different time points revealed that s-RNYs were significantly stable in the extracellular space (Northern blot analysis showing the stability of s-RNY1-5p in BMDMs stimulated with 1 μM of staurosporine (STS) over 72 hours; data not shown). This result may indicate that s-RNY stability is likely caused by their association with protein complex, microvesicles, exosomes, apoptotic bodies, or lipoproteins as it has been recently proved for extracellular miRNAs. In accordance with previous reports, Northern blot results show that non-miRNA species, such as U6 snRNA, are extremely unstable in the extracellular environment (data not shown).

Figure 16:
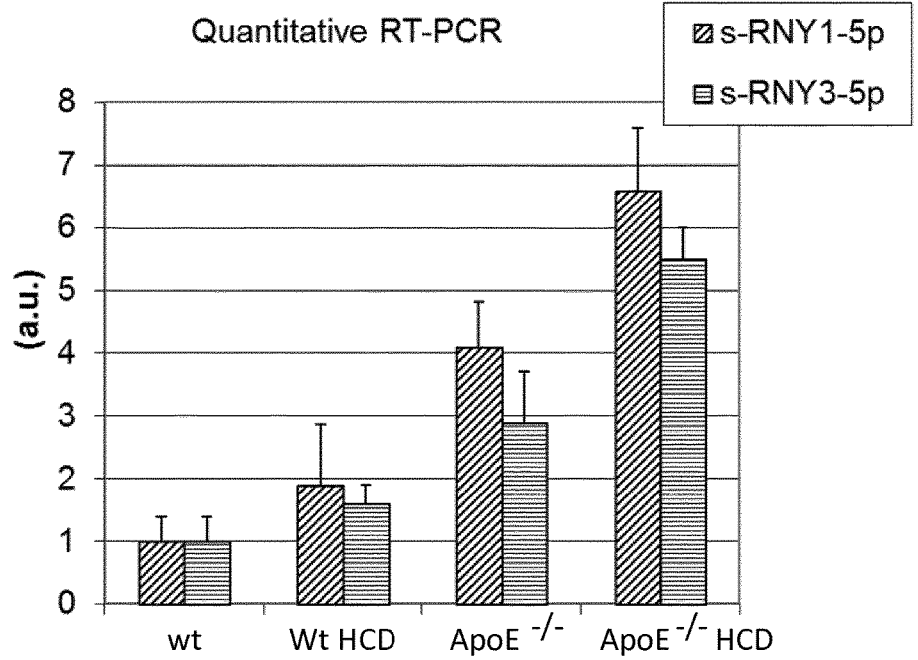
FIG. 16: Quantitative RT-PCR of the indicated s-RNYs in the blood plasma of ApoE$^{-/-}$ (A) or Ldlr$^{-/-}$ (B) mice or control. Mice were fed with either chow diet or HCD for either 12 (ApoE$^{-/-}$ mice) or 20 (Ldlr$^{-/-}$ mice) weeks. Data were normalized by using cel-miR-39 and are presented as mean and s.d. (n=8 for ApoE$^{-/-}$ and n=5 for Ldlr$^{-/-}$ mice). Student's t-test: *P<0.05, **P<0.01.
Figure 16:
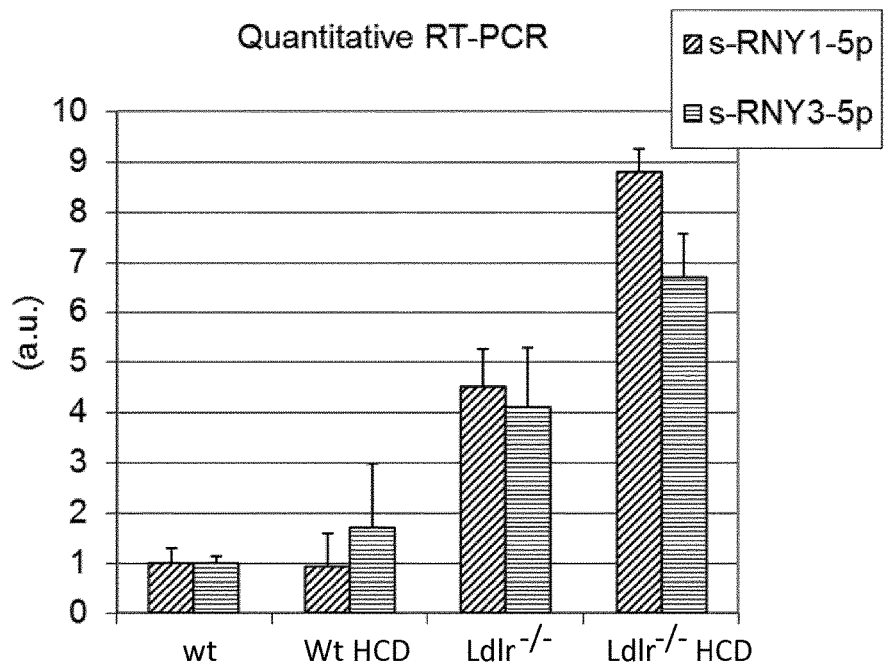

To test whether s-RNYs are significantly present in the blood of animal models for atherosclerosis s-RNY expression levels has been compared in the blood plasma of ApoE$^{-/-}$, Ldlr$^{-/-}$, and control mice. The animals were fed with either chow diet or HCD. As shown in FIG. 16, quantitative RT-PCR from blood plasma revealed that s-RNYs were significantly upregulated in ApoE$^{-/-}$ and Ldlr$^{-/-}$ mice compared to control, and even more when mice were fed with HCD.

Therefore, because of these data it can be logically anticipated that s-RNYs can be found in significant amounts in human body fluids of patients with atherosclerosis-related diseases. To validate this hypothesis, the expression of s-RNYs were measured in 45 male patients with stable Coronary Artery Disease (CAD) and 45 age-matched healthy normolipemic male subjects, in the context of a case-control study (Bouisset F. et al. (2012) *The American journal of cardiology* 110, 197-202). Metabolic and clinical variables of CAD and control individuals are summarized in Table 2.

TABLE 2

Clinical and biological characteristics of the study population

|  | Cases (n = 45) | Controls (n = 45) | P |
|---|---|---|---|
| Age (year) | 59.6 (±8.2) | 59.2 (±9.3) | 0.84 |
| Waist (cm) | 97.0 (±10.4) | 97.0 (±13.1) | 0.86 |
| BMI (kg/m2) | 26.8 (±4.0) | 27.8 (±5.4) | 0.29 |
| Triglycerides (g/L)[a] | 1.59 (±0.74) | 1.21 (±0.73) | 0.02 |
| Total cholesterol (g/L) | 2.16 (±0.41) | 2.20 (±0.40) | 0.70 |
| LDL-C (g/L) | 1.39 (±0.40) | 1.41 (±0.34) | 0.82 |
| HDL-C (g/L) | 0.48 (±0.15) | 0.55 (±0.13) | 0.003 |
| apoB (g/L) | 1.12 (±0.24) | 1.06 (±0.21) | 0.20 |
| apoA-I (g/L) | 1.24 (±0.25) | 1.51 (±0.24) | 0.001 |
| LpB:E (mg/L) | 85.6 (±44.8) | 45.3 (±45.6) | 0.001 |
| γ-GT (IU/L) | 53.3 (±34.1) | 40.0 (±32.0) | 0.06 |
| CRP[b] (mg/L) | 5.8 (±3.8) | 2.2 (±2.8) | 0.003 |

TABLE 2-continued

Clinical and biological characteristics of the study population

|  | Cases (n = 45) | Controls (n = 45) | P |
|---|---|---|---|
| Physical activity[c] | 1.9 (±0.8) | 2.3 (±0.9) | 0.03 |
| s-RNY1-5p[d] | 2.09 (±0.79) | 0.39 (±0.57) | 0.001 |

Data are expressed in mean (±SD) or %;
γ-GT: γ-glutamyltransferase;
CRP: C-Reactive Protein;
BMI: Body Mass Index.
[a]log transformed data;
[b]geometric mean;
[c]level of physical activity 1 to 4;
[d]square root value.

Figure 17:
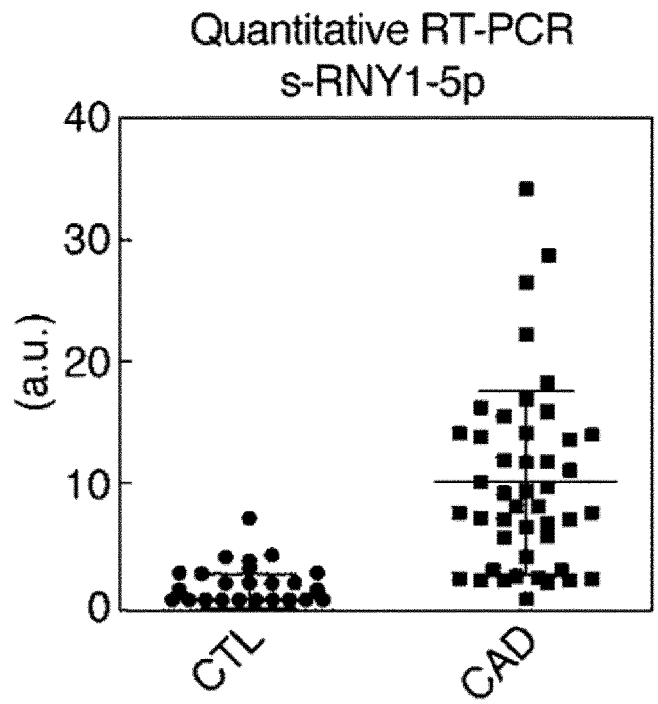
FIG. 17: (A) Significant different expression of circulating s-RNY1-5p in the serum of patients with Coronary Artery Disease (CAD, n=45) versus healthy control (CTR, n=45). Data derived from quantitative RT-PCR, normalized using cel-miR-39, and presented as mean and s.d. Student's t-test: ***P<0.001. (B) Receiver Operating Characteristic (ROC) curve for predicting CAD. The ROC curve was constructed using s-RNY1-5p based on the quantitative RT-PCR data (n=45). The area under the ROC curve is given and 95% confidence interval was calculated (0.90-0.99). The diagonal line indicates a test with an area under the ROC curve of 0.5.
Figure 17:
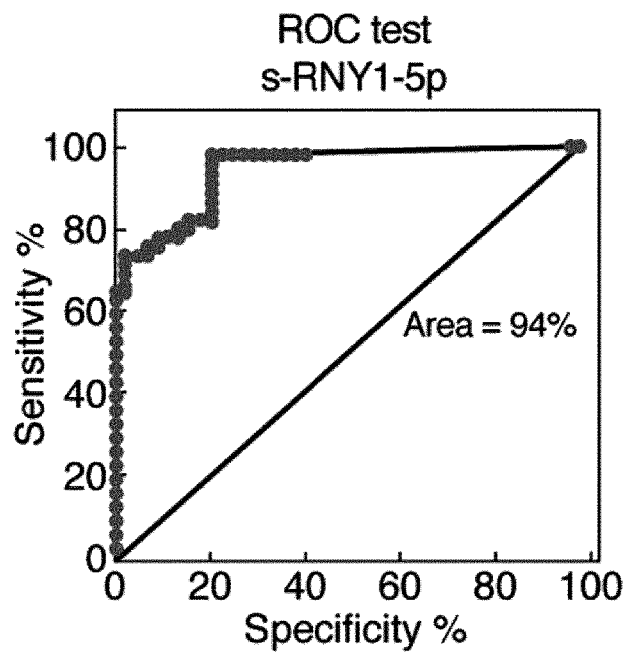
Figure 18:
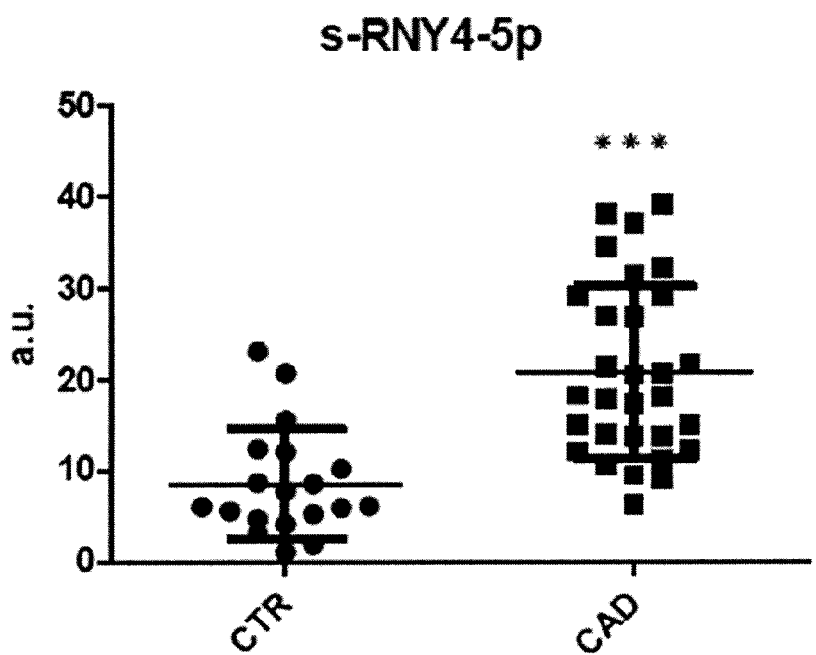
FIG. 18: Significant different expression of circulating s-RNY4-5p in the serum of patients with Coronary Artery Disease (CAD) versus control (CTR). (A) Data derived from quantitative RT-qPCR, Normalized by using cel-miR-39 and presented as mean and s.d. (CTR n=19; CAD n=30). (B) Area under the Receiver Operating Characteristic (ROC) curve for s-RNY4-5p based on the Quantitative RT-PCR data.
Figure 18:
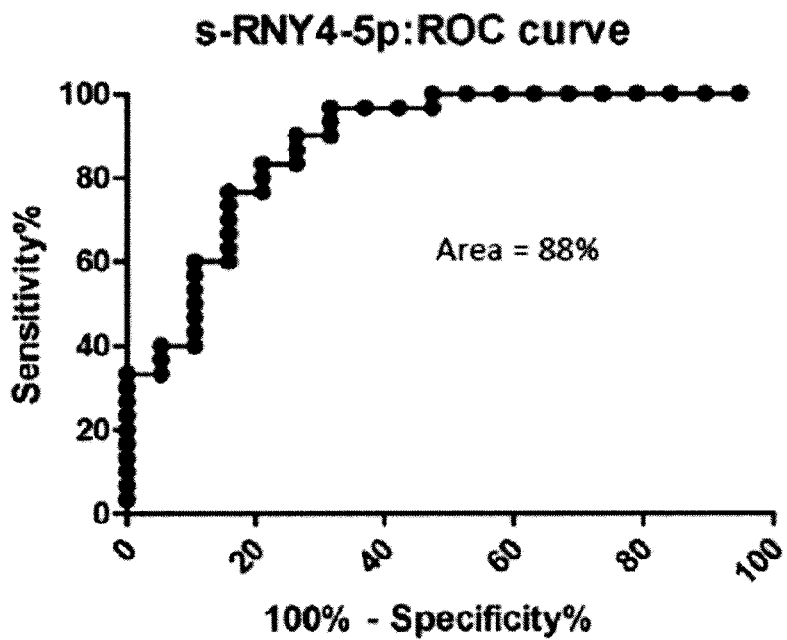
Figure 19:
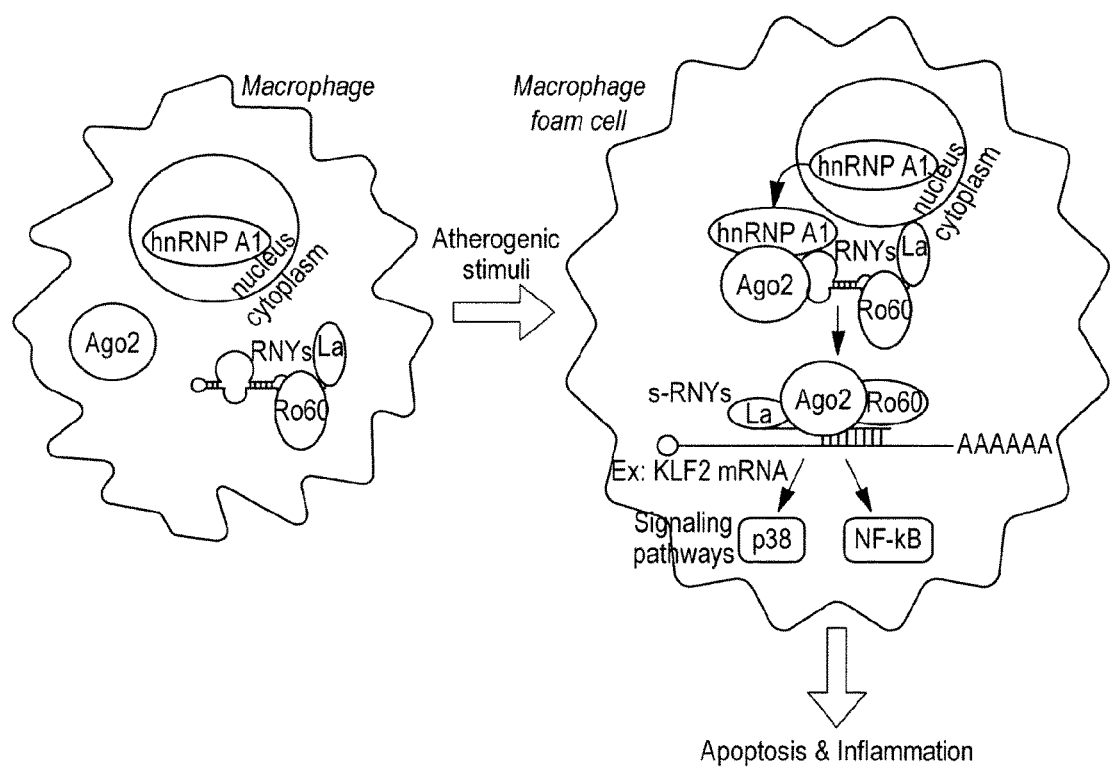
FIG. 19: s-RNYs are expressed in the peripheral blood of patients with coronary artery disease. A model for atherogenic lipids-dependent generation of s-RNYs that act on a subset of mRNAs containing seed complementary sequences and exert signaling pathway effects.
Figure 20:
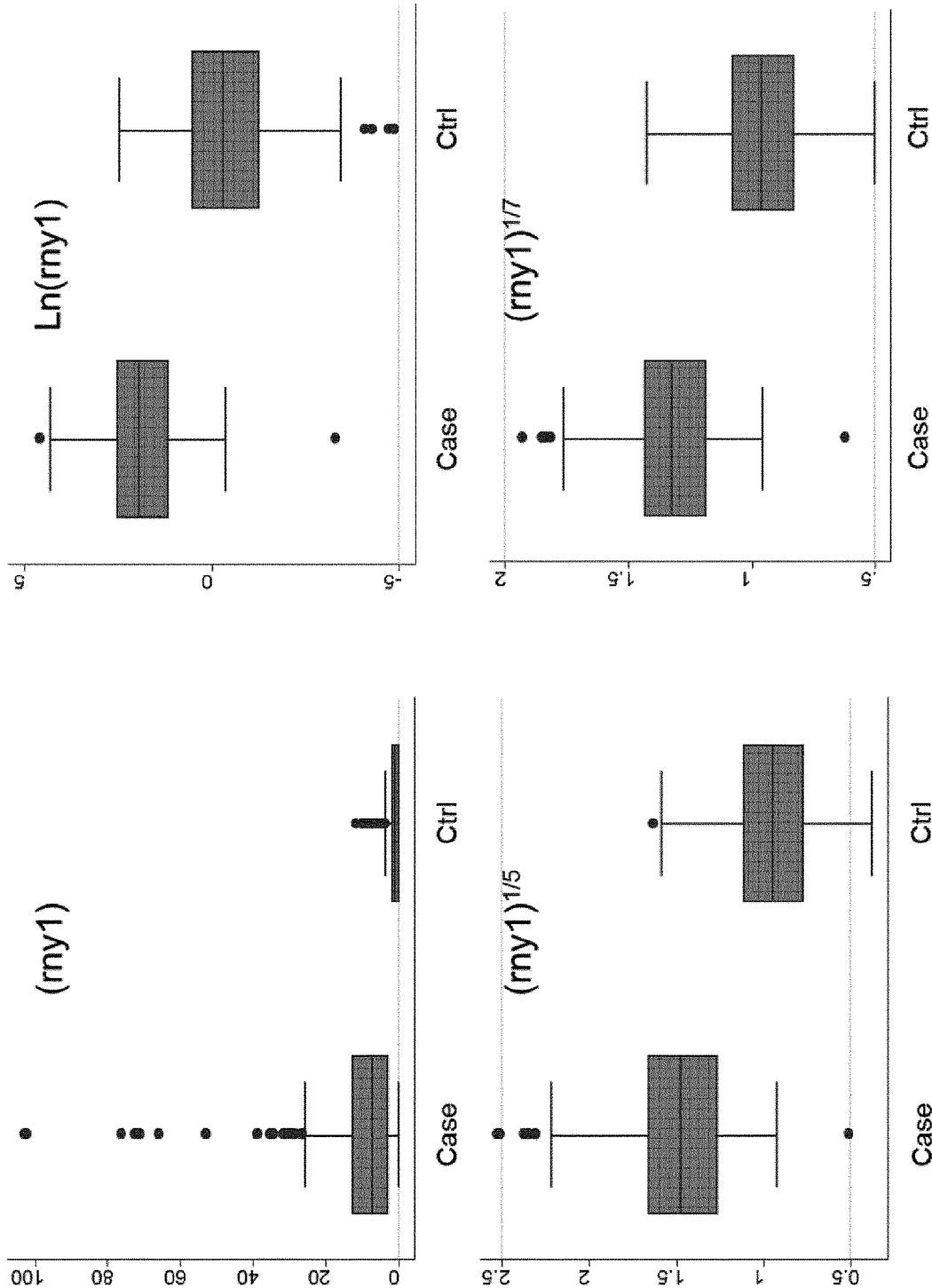
FIG. 20: Box plots of s-RNY1_5P according to coronary artery disease (CAD) status.
Figure 21:
FIG. 21: Normal density plots of crude and transformed s-rny1_5p.
Figure 21:
Figure 21:
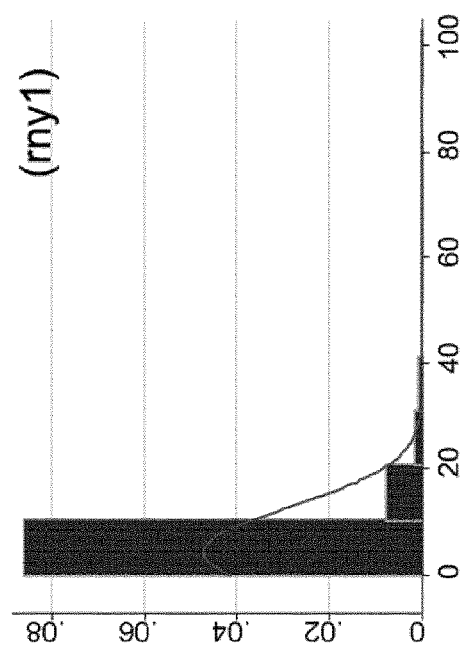
Figure 21:
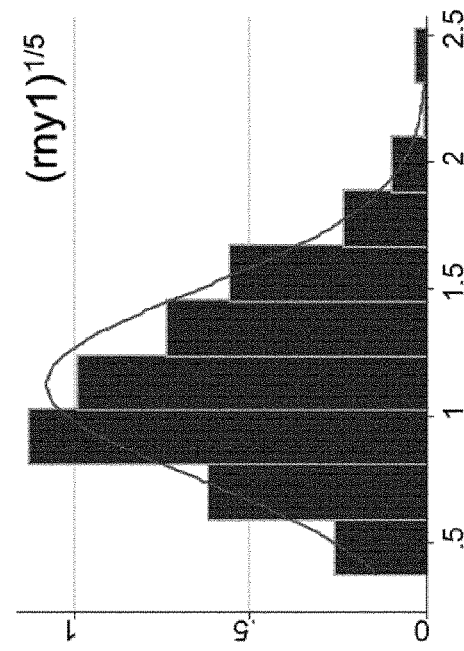

Among metabolic markers, total or LDL-cholesterol (LDL-C) were not significantly different between the two cohorts, probably reflecting effects of lipid-lowering drugs in CAD patients. However, CAD patients displayed higher levels of pro-atherogenic lipids such as triglycerides and lipoproteins containing ApoB and ApoE (LpB:E), increased CRP and lower atheroprotective high-density lipoprotein (HDL) markers such as HDL-cholesterol (HDL-C) and apoA-I levels. Body mass index (BMI) and waist circumference were not significantly different between cases and controls but physical activity was lower in cases and 84.4% of current or former smokers were found in cases against 55.6% in control individuals. Altogether, these clinical and biological characteristics reflect an increased prevalence of classical cardiovascular risk factors in CAD patients. A dysregulation of the expression of s-RNYs has been investigated in serum from CAD patients compared to healthy controls. Data show a significant upregulation of s-RNY1-5p expression in CAD patients (p<0.001, Table 2 and FIG. 17A). s-RNY4-5p was also detected in human serum and found unregulated in serum CAD patients compared to control individuals (p<0.001, Table 3 and FIG. 18A) while s-RNY3-5p was not detected in both CAD patients and control. Importantly, correlation between s-RNY1-5p levels and individual metabolic parameters and cardiovascular risk markers were investigated (Table 4).

TABLE 3

Clinical and biological characteristics of the study population (s-RNY4-5p)

|  | Cases (n = 30) | Controls (n = 19) | p |
|---|---|---|---|
| Age (year) | 59.2 (±7.7) | 59.1 (±8.6) | 0.98 |
| Waist (cm) | 98.0 (±11.8) | 101.0 (±15.1) | 0.52 |
| BMI (kg/m2) | 27.4 (±4.7) | 29.5 (±6.8) | 0.25 |
| Triglycerides (g/L)[a] | 1.56 (±0.76) | 1.56 (±0.93) | 0.97 |
| Total cholesterol (g/L) | 2.15 (±0.38) | 2.35 (±0.47) | 0.10 |
| LDL-C (g/L) | 1.37 (±0.35) | 1.52 (±0.42) | 0.20 |
| HDL-C (g/L) | 0.46 (±0.17) | 0.52 (±0.12) | 0.14 |
| apoB (g/L) | 1.14 (±0.25) | 1.08 (±0.26) | 0.49 |
| apoA-I (g/L) | 1.23 (±0.28) | 1.55 (±0.26) | 0.001 |
| LpB:E (mg/L) | 73.2 (±43.7) | 45.9 (±58.6) | 0.07 |
| γ-GT (IU/L) | 55.9 (±39.5) | 45.7 (±40.2) | 0.49 |
| CRP[b] (mg/L) | 6.9 (±3.7) | 2.6 (±4.6) | 0.006 |
| Physical activity[c] | 1.9 (±0.8) | 2.1 (±0.9) | 0.34 |
| s-RNY4-5p[d] | 4.43 (±1.00) | 2.75 (±0.99) | 0.001 |

Data are expressed in mean (±SD) or %;
γ-GT: γ-glutamyltransferase;
CRP: C-Reactive Protein;
BMI: Body Mass Index.
[a]log transformed data;
[b]geometric mean;
[c]level of physical activity 1 to 4;
[d]square root value.

TABLE 4

Sperman rank correlation coefficients between s-RNYs and some metabolic parameters and cardiovascular risk factors in the study population

|  | s-RNY1-5p[#] (n = 90) | p | s-RNY4-5p[#] (n = 49) | p |
|---|---|---|---|---|
| Age (year) | 0.01 | 0.91 | −0.22 | 0.13 |
| Waist (cm) | −0.02 | 0.83 | −0.08 | 0.60 |
| BMI (kg/m2) | −0.10 | 0.35 | −0.14 | 0.34 |
| Triglycerides (g/L) | 0.24 | 0.02 | 0.33 | 0.03 |
| Total cholesterol (g/L) | −0.07 | 0.48 | −0.06 | 0.69 |
| LDL-C (g/L) | −0.07 | 0.55 | −0.03 | 0.84 |
| HDL-C (g/L) | −0.37 | 0.001 | −0.27 | 0.06 |
| apoB (g/L) | 0.17 | 0.11 | 0.19 | 0.19 |
| apoA-I (g/L) | −0.56 | 0.001 | −0.39 | 0.006 |
| LpB:E (mg/L) | 0.36 | 0.001 | 0.52 | 0.001 |
| γ-GT (IU/L) | 0.28 | 0.009 | 0.34 | 0.02 |
| CRP (mg/L) | 0.43 | 0.001 | 0.47 | 0.001 |
| Physical activity[a] | −0.21 | 0.05 | −0.34 | 0.02 |

[#]Spearman rank correlation;
γ-GT: γ-glutamyltransferase;
CRP: C-Reactive Protein;
BMI: Body Mass Index.
[a]level of physical activity 1 to 4 s-RNY1-5p was positively correlated with pro-atherogenic lipids (triglycerides and LpB:E) and negatively with HDL markers (HDL-C and apoA-I). Environmental factors, such as physical activity and an inflammatory condition, as documented by elevated CRP, displayed positive correlation with RNY1-5p (Table 4). Same correlations were found for s-RNY4-5p (Table 4). Overall, these data indicate a strong correlation between s-RNYs and CAD risk, as it was attested by the high score of the area under the ROC curves (FIGS. 17B and 18B), supporting the hypothesis that s-RNY1-5p and s-RNY4-5p measurement might improve CAD risk prediction.

The upregulation of RNY-derived small RNAs (in particular s-RNY1-5p) in patients with coronary artery disease was confirmed on a larger cohort of patients (n=263) (see Table 5 and FIGS. 20-25).

TABLE 5

Demographic, clinical and biological characteristics of patients and controls

|  | Case | | Control | | t-test or |
|---|---|---|---|---|---|
|  | mean | SD | mean | SD | CHI2 |
|  | n = 263 | | n = 514 | | p |
| s-RNY1-5p | 10.42 | 12.33 | 1.32 | 1.67 | 0.001** |
| (RNY1-5p)$^{1/5}$ | 1.49 | 0.28 | 0.94 | 0.25 | 0.001 |
| (RNY1-5p)$^{1/6}$ | 1.39 | 0.22 | 0.95 | 0.22 | 0.001 |
| (RNY1-5p)$^{1/7}$ | 1.33 | 0.18 | 0.95 | 0.19 | 0.001 |
| Quartiles RNY1-5p (%) |  |  |  |  | 0.001 |
| Q1: <0.474 | 0.4 |  | 37.9 |  |  |
| Q2: 0.474-1.618 | 5.3 |  | 34.6 |  |  |
| Q3: 1.619-4.701 | 28.5 |  | 23.4 |  |  |
| Q4: >4.701 | 65.8 |  | 4.1 |  |  |
| Total cholesterol (g/L) | 2.02 | 0.38 | 2.24 | 0.38 | 0.001 |
| HDL cholesterol (g/L) | 0.43 | 0.12 | 0.55 | 0.13 | 0.001 |
| LDL cholesterol (g/L) | 1.25 | 0.34 | 1.45 | 0.32 | 0.001 |
| Serum triglyceride (g/L) | 1.68 | 0.89 | 1.21 | 0.77 | 0.001* |
| Apolipoprotein A1 (g/L) | 1.23 | 0.22 | 1.50 | 0.24 | 0.001 |
| Apolipoprotein B (g/L) | 1.04 | 0.22 | 1.08 | 0.22 | 0.03 |
| ApoC3 (mg/L) | 33.8 | 12.9 | 30.8 | 12.7 | 0.002 |
| ApoE (mg/L) | 99.4 | 56.0 | 71.5 | 46.5 | 0.001* |
| LpBC3 (mg/L) | 16.4 | 10.6 | 14.1 | 10.5 | 0.006 |
| LpBE (mg/L) | 76.4 | 56.7 | 48.6 | 46.1 | 0.001* |
| Lp(a) (g/L) | 0.47 | 0.44 | 0.30 | 0.37 | 0.001* |
| IF1 (mg/L) | 0.43 | 0.14 | 0.52 | 0.15 | 0.001 |

TABLE 5-continued

Demographic, clinical and biological characteristics of patients and controls

| | Case | | Control | | t-test or |
|---|---|---|---|---|---|
| | mean n = 263 | SD | mean n = 514 | SD | CHI2 p |
| Gamma glutamyl transferase (IU/L) | 62.8 | 68.6 | 45.2 | 56.8 | 0.001** |
| High sensitivity C reactive protein (mg/L) | 17.2 | 29.7 | 3.1 | 5.1 | 0.001** |
| Fasting glucose (mmol/l) | 5.93 | 2.01 | 5.43 | 1.06 | 0.19** |
| Serum insulin (UI/L) | 15.9 | 19.5 | 10.0 | 8.1 | 0.001** |
| HOMA-IR | 4.2 | 4.9 | 2.6 | 2.8 | 0.001** |
| Adiponectin (µg/mL) | 5.6 | 4.3 | 7.0 | 4.4 | 0.001 |
| Waist (cm) | 99.3 | 10.7 | 95.3 | 9.9 | 0.001 |
| Waist to hip ratio | 0.99 | 0.04 | 0.96 | 0.05 | 0.001 |
| Body mass index (kg/m$^2$) | 27.5 | 4.0 | 26.9 | 3.6 | 0.04 |
| Systolic blood pressure (mmHg) | 137.0 | 20.2 | 137.4 | 16.5 | 0.82** |
| Diastolic blood pressure (mmHg) | 83.5 | 11.2 | 82.7 | 7.9 | 0.55** |
| Resting heart rate (beat/mn)*** | 63.7 | 11.5 | 62.8 | 9.2 | 0.79** |
| Body Fat (bioelectrical impedance %) | 28.2 | 5.4 | 26.2 | 5.1 | 0.001 |
| Age (year) | 60.3 | 8.0 | 59.0 | 8.3 | 0.04 |
| Schooling (number of years spent at school) | 9.6 | 3.0 | 13.1 | 4.3 | 0.001** |
| Current tobacco consumption (number cig) | 3.4 | 10.1 | 2.3 | 7.0 | 0.22** |
| Tobacco consumption number (pack year) | 41.5 | 37.9 | 17.2 | 21.3 | 0.001** |
| Physical activity score | 1.86 | 0.67 | 2.23 | 0.82 | 0.001** |
| Alcohol consumption (g/day) | 28.8 | 28.5 | 23.8 | 24.1 | 0.09** |
| Wine | 25.8 | 26.4 | 20.4 | 21.8 | 0.02** |
| Schooling (number of years spent at school) % | | | | | 0.001 |
| <9 | 42.2 | | 17.5 | | |
| 9-10 | 32.7 | | 9.0 | | |
| >10 | 25.1 | | 73.5 | | |
| Treatment for hypertension (%) | 44.1 | | 19.6 | | 0.001 |
| Treatment for diabetes (%) | 23.2 | | 5.2 | | 0.001 |
| Treatment for dyslipidemia (%) | 63.5 | | 23.3 | | 0.001 |
| Smoking (%) | | | | | 0.001 |
| current | 18.3 | | 14.6 | | |
| former | 65.4 | | 50.4 | | |
| never | 16.3 | | 35.0 | | |
| Ankle-arm index ≤ 0.9 (%) | 33.6 | | 1.6 | | 0.001 |
| Physical activity (%) | | | | | 0.001 |
| no | 27.4 | | 18.5 | | |
| medium | 61.6 | | 45.9 | | |
| high | 11.0 | | 35.6 | | |
| Alcohol consumption (%) | | | | | 0.03 |
| no | 17.1 | | 12.4 | | |
| <40 g/day | 54.4 | | 64.3 | | |
| ≥40 g/day | 28.5 | | 23.3 | | |
| Metabolic syndrome (NCEP ATP-III %) | 48.5 | | 17.7 | | 0.001 |

*analyses performed on log transformed data
**Kruskal-Wallis test

The level of expression of these small RNAs was also checked in 514 healthy individuals and it was found that the higher expression of s-RNY1-5p is associated with high levels of CRP, LDLc, ApoB and lower levels of ApoA. 24 patients infected by bacteria, therefore having high CRP but no atheroscerostis, show intermediate levels of s-RNY1-5p expression.

Taken together, the highest levels of s-RNY1-5p are specifically associated to patients with atherosclerosis.

Figure 22:
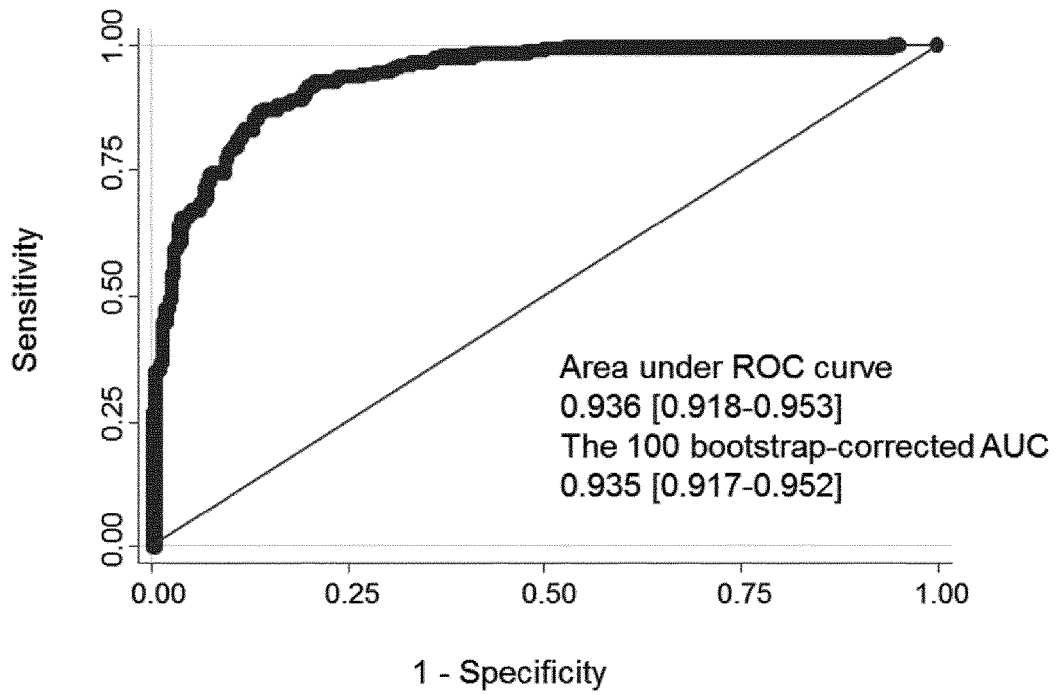
FIG. 22: Receiver-operator characteristic (ROC) curve for prediction of CAD with s-RNY1-5p.
Figure 23:
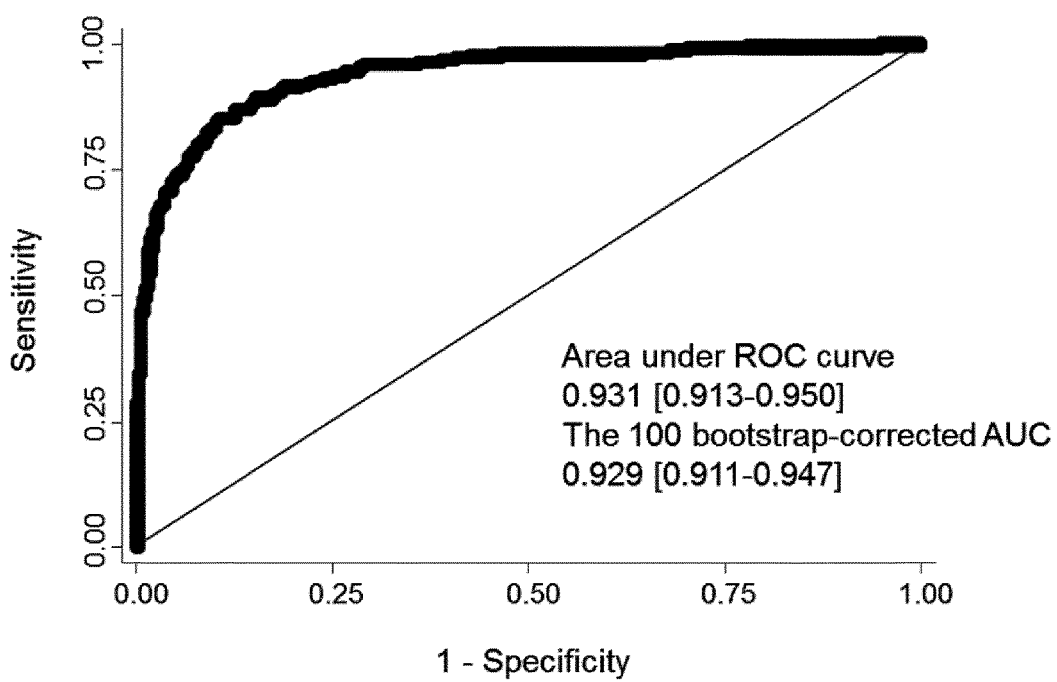
FIG. 23: ROC curve for prediction of CAD with hypertension, dyslipidemia, diabetes, smoking, school duration, ankle-arm index, ApoA1 and CRP.
Figure 24:
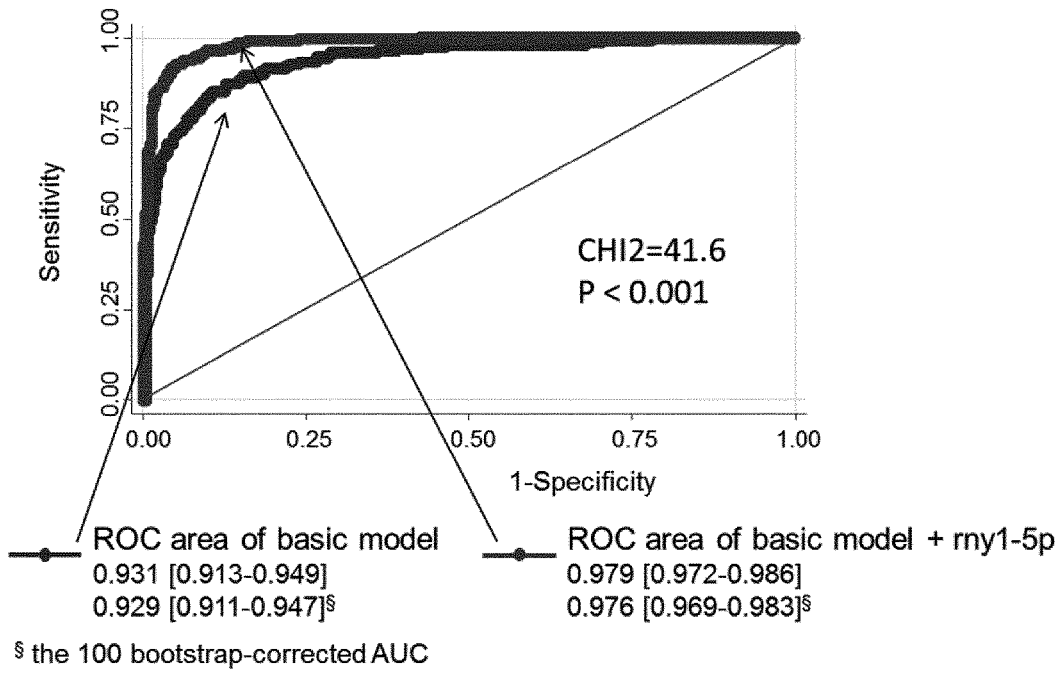
FIG. 24: ROC curves for prediction of CAD Comparison of basic cardiovascular risk factors model with full model (+s-RNY1_5P).
Figure 25:
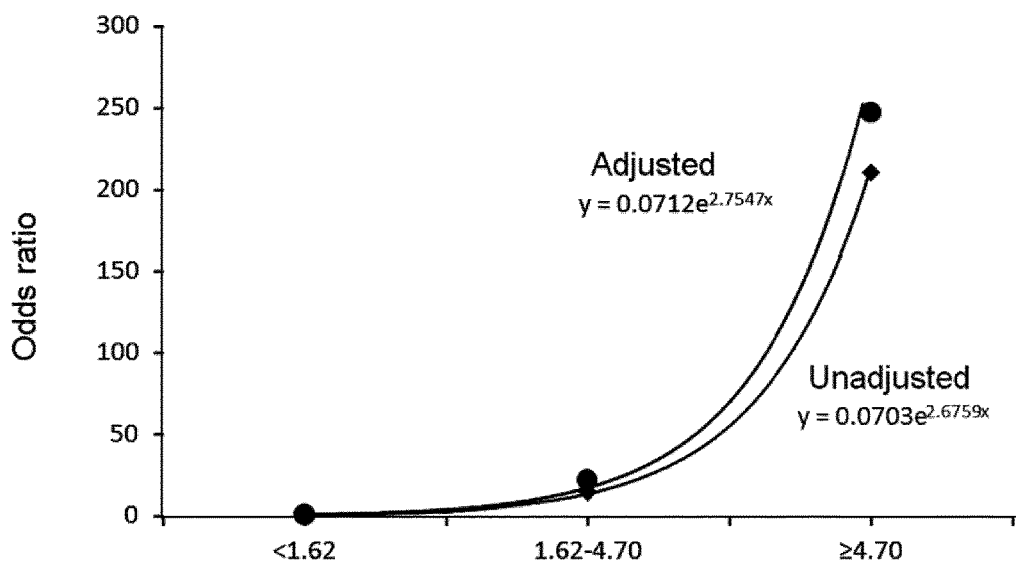
FIG. 25: Odds ratio for s-RNY1_5P.

FIGS. 22-24 respectively display ROC curve for prediction of CAD based on (i) s-RNY1-5p, (ii) basic cardiovascular risk factors (hypertension, dyslipidemia, diabetes, smoking, school duration, ankle-arm index, ApoA1 and CRP), or (iii) s-RNY1-5p combined with basic cardiovascular risk factors, A ROC curve is a graphical representation of the sensitivity (or true positive rate) against the false positive rate (i.e. [1—specificity], specificity being the true negative rate) of a marker-based test. A ROC space is defined by sensitivity and (1-specificity) as x and y axes respectively. The best possible prediction method would yield a point in the upper left corner or coordinate (0,1) of the ROC space, representing 100% sensitivity (no false negatives) and 100% specificity (no false positives). A completely random guess would give a point along a diagonal line (the so-called line of no-discrimination) from the left bottom to the top right corners. The diagonal divides the ROC space. Points above the diagonal represent good classification results (better than random), points below the line poor results (worse than random). The Area Under the Curve (AUC) of a ROC curve may be calculated. The higher the AUC, the higher the diagnostic accuracy of the diagnostic marker.

For combined analysis of markers, a new virtual marker Z is calculated based on a linear combination of the levels of the individual markers. Z is calculated as follows: $Z = \Sigma a_i \times [Marker_i]$ where $a_i$ are calculated coefficients and [$Marker_i$] are individual levels of marker (optionally in normalised units). The values of the $a_i$ coefficients are determined in order to maximize the Area Under the Curve (AUC) of the ROC curve for the selected marker combination. Determination of the coefficient values may be readily achieved using for instance mROC program or any other program implementing an algorithm for maximising the AUC of ROC which may be used for multivariate ROC.).

The results shown on FIG. 24 indicate that s-RNY1-5p improves the diagnostic accuracy of CAD when combined with basic cardiovascular risk factors.

The invention claimed is:

1. A method of treating an atherosclerosis-related disorder selected from the group consisting of atherosclerosis, chronic kidney disease, cerebrovascular disease, peripheral vascular disease, ischemic heart disease, carotid artery disease, and coronary artery disease in an individual in need thereof, which comprises:
   a) diagnosing or prognosing the individual with an atherosclerosis-related disorder by measuring the level of expression of at least one biomarker consisting of a small Y RNA (s-RNY) in a biological sample of said individual, wherein a level of expression of said biomarker higher than a reference value is indicative that the individual has developed or is at risk of developing an atherosclerosis-related disorder; and
   b) administering a therapeutically effective amount of an anti-atherosclerosis drug to said individual diagnosed or prognosed with an atherosclerosis-related disorder, wherein said anti-atherosclerosis drug is selected from the group consisting of bile acid sequestrant, niacin, statins, fibrates, probucol, an s-RNY inhibitor, and combinations thereof.

2. The method of claim 1, wherein step a) comprises:
   a) determining the level of expression of at least one biomarker consisting of a small Y RNA (s-RNY) in a biological sample of said individual;
   b) comparing the level of expression of said at least one biomarker with a reference value, wherein a level of expression of said biomarker higher than the reference value is indicative that the individual has developed or is at risk of developing an atherosclerosis-related disorder, and
   c) deducing for said comparison if the individual has developed or is at risk of developing an atherosclerosis-related disorder.

3. The method of claim 1, wherein in step a) said at least one biomarker is selected from the group consisting of s-RNY1-5p (SEQ ID NO: 7), s-RNY1-3p (SEQ ID NO: 8), s-RNY3-5p (SEQ ID NO: 9), s-RNY3-3p (SEQ ID NO: 10), s-RNY4-5p (SEQ ID NO: 11), s-RNY4-3p (SEQ ID NO: 12), and s-RNY5-3p (SEQ ID NO: 13) or variants thereof.

4. The method of claim 1, wherein said atherosclerosis-related disorder is coronary artery disease.

5. The method of claim 1, wherein said anti-atherosclerosis drug is an inhibitor of a s-RNY selected from the group consisting of s-RNY1-5p (SEQ ID NO: 7), s-RNY1-3p (SEQ ID NO: 8), s-RNY3-5p (SEQ ID NO: 9) and S-RNY4-5p (SEQ ID NO: 11).

6. The method according to claim 5 wherein said inhibitor of a s-RNY is a nucleic acid which specifically hybridizes to at least one sequence selected from the group consisting of SEQ ID NO: 7 (s-RNY1-5p), SEQ ID NO: 9 (s-RNY3-5p), SEQ ID NO: 8 (s-RNY1-3p) and SEQ ID NO: 11 (s-RNY4-5p).

* * * * *